US006670124B1

(12) United States Patent
Chow et al.

(10) Patent No.: US 6,670,124 B1
(45) Date of Patent: Dec. 30, 2003

(54) HIGH THROUGHPUT METHODS OF HLA TYPING

(75) Inventors: Robert Chow, Arcadia, CA (US); Richard Tonai, Valencia, CA (US)

(73) Assignee: StemCyte, Inc., Arcadia, CA (US)

( * ) Notice: Subject to any disclaimer, the term of this patent is extended or adjusted under 35 U.S.C. 154(b) by 0 days.

(21) Appl. No.: 09/747,391

(22) Filed: Dec. 20, 2000

Related U.S. Application Data

(60) Provisional application No. 60/172,768, filed on Dec. 20, 1999.

(51) Int. Cl.$^7$ .......................... C12Q 1/68; C07H 21/04

(52) U.S. Cl. ........................ 435/6; 435/91.2; 536/24.3; 536/23.1; 536/24.31

(58) Field of Search .................. 435/6, 91.2; 536/24.3, 536/23.1, 24.31

(56) References Cited

U.S. PATENT DOCUMENTS 5,143,854 A 9/1992 Pirrung et al. .............. 436/518
6,017,738 A * 1/2000 Morris et al.

OTHER PUBLICATIONS

Allele–Specific HLA–DRB1 Amplificationof Forensic Evidence Samples with Mixed Genotypes—Marie Allen, Tom Saldeen and Ulf Gyllensten—1995.*

HLA class II genotyping by reverse dot blot method—Toshihiko Kaneshige and Kiyoshisa Uchida—1994.*

HLA class II typing in a microtitre plate formate using digoxigenin labelled amplified dna and biotin–Labelled oligonucleotide probes—LMU Munchen– Jun. 16, 1993.*

Bunce and Welsh: "Rapid DNA typing for HLA–C using sequence–specific primers (PRC–SSP): Identification of serological and non–serologically defined HLA–C alleles including several new alleles" *Tissue Antigens* 43:7–17 (1994).

Bunce et al.: "Phototyping: comprehensive DNA typing for HLA–A, B, C, DRB1, DRB3, DRB4, DRB5 and DQB1 by PCR with 144 primer mixes utilizing sequence–specific primers (PCR–SSP)" *Tissue Antigens* 46:355–367 (1995).

Cereb et al.: "Locus–specific amplification of HLA class I genes from genomic DNA: locus–specific sequences in the first and third introns of HLA–A, –B, and –C alleles" *Tissue Antigens* 45:1–11 (1995).

Erlich et al.: "HLA–DR, DQ and DP typing using PCR amplification and immobilized probes" *Eur. J. Immunogenet*. 18: 33–55 (1991).

Gilchrist et al.: "Comprehensive HLA–DP typing using polymerase chain reaction with sequence–specific primers and 95 sequence–specific primer mixes" *Tissue Antigens* 51:51–61 (1998).

Kawasaki et al.: "Genetic Analysis Using Polymerase Chain Reaction–Amplified DNA and Immobilized Oligonucleotide Probes: Reverse Dot–Blot Typing" *Methods in Enzymology* 218:369–381 (1993).

Krausa and Browning: "Detection of HLA gene polymorphism" in *HLA and MHC:genes molecules and function*. Oxford: BIOS Scientific Publishers Ltd., 113–138 (1996).

Olerup and Zetterquist: "HLA–DR typing by PCR amplification with sequence–specific primers (PCR–SSP) in 2 hours: An alternative to serological DR typing in clinical practice including donor–recipient matching in cadaveric transplantation" *Tissue Antigens* 39: 225–235 (1992).

Mason and Parham: "HLA class I region sequences, 1998" *Tissue Antigens* 51: 417–466 (1998).

Marsh and Bodmer: "HLA Class II Nucleotide Sequences, 1992" *Hum. Immunol.* 35: 1–17 (1992).

Nevinny–Stickel and Albert: "HLA Class II Typing in a Microtitre Plate Formate Using Digoxigenis–Labelled Amplified DNA and Biotin–Labeled Oligonucleotide Probes" *Eur. J. Immunogenet*. 20: 419–427 (1993).

Paitek et al.: "Molecular beacon sequence analysis for detecting drug resistence in *Mycobacterium tuberculosis*" *Nature Biotechnology* 16:359–363 (1998).

Kostrikis et al.: "Spectral Genotyping of Human Alleses" *Science* 279: 1228–1229 (1998).

Saiki et al.: "Genetic analysis of amplified DNA with immobilized sequence–specific oligonucleotide probes" *Proc. Natl. Acad Sci. USA* 86: 6230–6234 (1989).

Sasazuki et al.: "Effect of Matching of Class I HLA Alleles on Clinical Outcome after Transplantation of Hematopoietic Stem Cells from an Unrelated Donor" *New England J. of Medicine* 339: 1177–1185 (1998).

Tyagi and Kramer: "Molecular Beacons: Probes that Fluoresce upon Hybridization" *Nature Biotechnology* 14: 303–308 (1996).

Tyagi et al.: "Multicolor molecular beacons for allele discrimination" *Nature Biotechnology* 16: 49–53 (1998).

(List continued on next page.)

*Primary Examiner*—Jeffrey Fredman
*Assistant Examiner*—Juliet Switzer
(74) *Attorney, Agent, or Firm*—Townsend and Townsend and Crew LLP

(57) ABSTRACT

A method for determining an HLA genotype of a subject is disclosed. The method comprises (a) isolating template nucleic acid from the subject; (b) amplifying the template nucleic acid to generate sufficient product for each allele of at least one gene locus to be determined; (c) hybridizing the template nucleic acid with an immobilized array of capture oligonucleotides, each having a known nucleic acid sequence of an HLA allele; and (d) determining the particular capture oligonucleotide to which the template nucleic acid hybridizes, thereby determining the genotype of the subject. A number of additional methods that can eliminate or abbreviate additional steps are also described. Moreover, the present invention provides a method for determining tissue compatibility using the determined HLA genotype.

8 Claims, No Drawings

OTHER PUBLICATIONS

Angelini et al.: "High–resolution analysis of the human HLA–DR polymorphism by hybridization with sequence–specific oligonucleotide probes" *Proc. Natl. Acad. Sci. USA* 83: 4489–4493 (1986).
Crouse et al.: "Analysis and Interpretation of the HLA DQα '1.1 Weak Signal' Observed During the PCR–Based Typing Method" *J. of Forensic Sci.* 39:41–51 (1994).
Hansen, J.,: "Development of registries of HLA–typed volunteer marrow donors" *Tissue Antigens* 47: 460–463 (1996).
Ng et al.: "Large–scale DRB and DQB1 oligonucleotide typing for the NMDP registry: progress report from year 2" *Tissue Antigens* 47:21–26 (1996).
Park and Tonai: "Phenotype Frequencies of the Class II (DR, DQ) DNA Alleles by the Patterns of Sequence–Specific Primer Mixtures (SSPM) in Four Different Populations and the Probable Haplotypes Between DRB1 Allele and DQB1 Allele" *Clinical Transplants* 39:475–500 (1992).
Rubinstein et al.: "Outcomes Among 562 Recipients of Placental–Blood Transplants from Unrelated Donors" *New England Journal of Medicine* 339(22):1565–1577 (1998).
Saiki et al.: "Analysis of enzymatically amplified β–globin and HLA–DQα DNA with allele–specific oligonucleotide probes" *Nature* 324:163–166 (1986).
Saiki et al.: "Primer–Directed Enzymatic Amplification of DNA with a Thermostable DNA Polymerase" *Science* 239: 487–491 (1988).
Abstract, Tonai et al.: "Oligonucleotide Typing of HLA DR by Allele–Specific PCR Amplification," UCLA Tissue Typing Laboratory, UCLA School of Medicine, Los Angeles, CA, Basic Research (1990).
Yoshida et al.: "Polymerase–Chain–Reaction–Based Analysis of Polymorphism in the HLA–B Gene" *Hum. Immunol.* 34: 257–266 (1992).
Anasetti and Hansen: "Effect of HLA Incompatibility in Marrow Transplantation from Unrelated and HLA–mismatched Related Donors" *Transfus. Sci.* 15: 221–230 (1994).
Sasazuki and Kimura, Eds: "Introduction to the DNA component ;" HLA 1991, vol. 1 *Oxford University Press* (1992).
Bunce et al.: Comprehensive, serologically equivalent DNA typing for HLA–B by PCR using sequence–specific primers (PCR–SSP) *Tissue Antigens* 45:81–89.
Tiercy et al.: "A Comprehensive HLA–DRB, –DQB, and –DPB Oligotyping Procedure by Hybridization with Sequence–Specific Oligonucleotide Probes," Handbook of HLA Typing Techniques, 117–147, *CRC Press, Inc.* (1993).
User's Manual, Quick–Type™ HLA–A Class I, "Sequence Specific Oligonucleotide typing (SSO)", *Lifecodes Corporation*, 9 pages (1995).
Bidwell et al.: "Rapid HLA–DR–Dw and DP Matching by PCR Fingerprinting and Related DNA Heteroduplex Technologies," Handbook of HLA Typing Techniques, 99–115, *CRC Press, Inc.* (1993).
Abe et al.: "Rapid DNA typing utilizing immobilized oligonucleotide probe and a nonradioactive detection system" *J. Immunol. Meth.* 154: 205–210 (1992).
Allen et al.: "High resolution genetic typing of the lcass II HLA–DRB1 locus using group–specific amplification and SSO–hybridisation in microplates" *Hereditas* 129: 161–167 (1998).
Bugawan et al.: "Rapid HLA typing using enzymatically amplified DNA and nonradioactive sequence–specific oligonucleotide probes" *Immunogenetics* 32: 231–241 (1990); *Erratum, Immunogenetics* 34:: 413 (1991).
Bugawan et al.: "A method for typing polymorphism at the HLA–A locus using PCR amplification and immobilized oligonucleotide probes" *Tissue Antigens* 44: 137–147 (1994).
Buyse et al.: "A three–step allele–level DRB–1–DRB3–DRB4–DRB5 genotyping assay using polymerase chain reaction with immobilized sequence–specific oligoprobes" *Tissue Antigens* 50: 291–302 (1997).
Kawai et al.: "A Simple Method of HLA–DRB Typing Using Enzymatically Amplified DNA and Immobilized Probes on Microtiter Plate" *Hum. Immunol.* 41: 121–126 (1994).
Kostyu et al.: "Rapid HLA–DR Oligotyping by an Enzyme–Linked Immunosorbent Assay Performed in Microtiter Trays" *Hum. Immunol.* 38: 148–158 (1993).
Lazaro et al.: "Enzyme–Linked DNA Oligotyping; A Practical Method for Clinical HLA–DNA Typing" *Hum. Immunol.* 36: 243–248 (1993).
Olerup and Zetterquist: "HLA–DR Typing by Polymerase Chain Reaction Amplification with Sequence–Specific Primers (PCR–SSP)" Handbook of HLA Typing Techniques, pp. 149–173, *CRC Press, Inc.* (1993).
Terasaki and McClelland: "Microdroplet Assay of Human Serum Cytotoxins" *Nature* 204: 998–1000 (1964).
Levenson and Chang, "Nonisotopically Labeled Probes and Primers," *PCR Protocols: A Guide to Methods and Applications*, 99–112 (1990).
Innis and Gelfand, "Optimization of PCRs," PCR Protocols: A Guide to Methods and Applications, 3–12 (1990).
Fodor et al.: "Light–Directed, Spatially Addressable Parallel Chemical Synthesis" *Science* 251: 767–773 (1991).
Tiercy et al.: "A New Approach for the Analysis of HLA Class II Polymorphisms: 'HLA Oligotyping'" *Blood Review* 4: 9–15.

* cited by examiner

HIGH THROUGHPUT METHODS OF HLA TYPING

CROSS-REFERENCES TO RELATED APPLICATIONS

This application claims the benefit of U.S. Provisional Patent application Serial No. 60/172,768, filed on Dec. 20, 1999, the teachings of which are herein incorporated by reference.

FIELD OF THE INVENTION

In general, this invention relates to typing and matching human leukocyte antigens or alleles of human leukocyte antigens and in particular, to high throughput screening methods of human leukocyte antigen matching or alleles of human leukocyte antigens.

BACKGROUND OF THE INVENTION

The human leukocyte antigen complex (also known as the major histocompatibility complex) spans approximately 3.5 million base pairs on the short arm of chromosome 6. It is divisible into 3 separate regions which contain the class I, the class II and the class III genes. In humans, the class I HLA complex is about 2000 kb long and contains about 20 genes. Within the class I region exist genes encoding the well characterized class I MHC molecules designated HLA-A, HLA-B and HLA-C. In addition, there are nonclassical class I genes that include HLA-E, HLA-F, HLA-G, HLA-H, HLA-J and HLA-X as well as a new family known as MIC. The class II region contains three genes known as the HLA-DP, HLA-DQ and HLA-DR loci. These genes encode the α and β chains of the classical class II MHC molecules designated HLA-DR, DP and DQ. In humans, nonclassical genes designated DM, DN and DO have also been identified within class II. The class III region contains a heterogeneous collection of more than 36 genes. Several complete components are encoded by three genes including TNF-α and TNF-β.

Any given copy of chromosome 6 can contain many different alternative versions of each of the preceding genes and thus can yield proteins with distinctly different sequences. The loci constituting the MHC are highly polymorphic, that is, many forms of the gene or alleles exist at each locus. Several hundred different allelic variants of class I and class II MHC molecules have been identified in humans. However, any one individual only expresses up to 6 different class I molecules and up to 12 different class II molecules.

The foregoing regions play a major role in determining whether transplanted tissue will be accepted as self (histocompatible) or rejected as foreign (histoincompatible). For instance, within the class II region, three loci i.e., HLA-DR, DQ and DP are known to express functional products. Pairs of A and B genes within these three loci encode heterodimeric protein products which are multi-allelic and alloreactive. In addition, combinations of epitopes on DR and/or DQ molecules are recognized by alloreactive T cells. This reactivity has been used to define "Dw" types by cellular assays based upon the mixed lymphocyte reaction (MLR). It has been demonstrated that matching of donor and recipient HLA-DR and DQ alleles prior to allogeneic transplantation has an important influence on allograft survival. Therefore, HLA-DR and DQ matching is now generally undertaken as a clinical prerequisite for renal and bone marrow transplantation as well as cord blood applications.

Until recently, matching has been confined to serological and cellular typing. For instance, in the microcytotoxicity test, white blood cells from the potential donor and recipient are distributed in a microtiter plate and monoclonal antibodies specific for class I and class II MHC alleles are added to different wells. Thereafter, complement is added to the wells and cytotoxicity is assessed by uptake or exclusion to various dyes by the cells. If the white blood cells express the MHC allele for a particular monoclonal antibody, then the cells will be lysed on addition of complement and these dead cells will take up the dye. (see, Terasaki and McClelland, (1964) *Nature,* 204:998). However, serological typing is frequently problematic, due to the availability and crossreactivity of alloantisera and because live cells are required. A high degree of error and variability is also inherent in serological typing, which ultimately affects transplant outcome and survival (Sasazuki et al., (1998) *New England J. of Medicine* 339: 1177–1185). Therefore, DNA typing is becoming more widely used as an adjunct, or alternative, to serological tests.

Initially, the most extensively employed DNA typing method for the identification of these alleles has been restriction fragment length polymorphism (RFLP) analysis. This well established method for HLA class II DNA typing suffers from a number of inherent drawbacks. RFLP typing is too time-consuming for clinical use prior to cadaveric renal transplantation for example, and for this reason it is best suited to live donor transplantation or retrospective studies. Furthermore, RFLP does not generally detect polymorphism within the exons which encode functionally significant HLA class II epitopes, but relies upon the strong linkage between alleles-specific nucleotide sequences within these exons and restriction endonuclease recognition site distribution within surrounding, generally noncoding, DNA.

In addition to restriction fragment length polymorphism (PCR-RFLP), an even more popular approach has been the hybridization of PCR amplified products with sequence-specific oligonucleotide probes (PCR-SSO) to distinguish between HLA alleles (see, Tiercy et al., (1990) *Blood Review* 4: 9–15). This method requires a PCR product of the HLA locus of interest be produced and then dotted onto nitrocellulose membranes or strips. Then each membrane is hybridized with a sequence specific probe, washed, and then analyzed by exposure to x-ray film or by colorimetric assay depending on the method of detection. Similar to the PCR-SSP methodology, probes are made to the allelic polymorphic area responsible for the different HLA alleles. Each sample must be hybridized and probed at least 100–200 different times for a complete Class I and II typing. Hybridization and detection methods for PCR-SSO typing include the use of non-radioactive labeled probes, microplate formats, etc. (see e.g., Saiki et al. (1989) *Proc. Natl. Acad. Sci., U.S.A.* 86: 6230–6234; Erlich et al. (1991) *Eur. J. Immunogenet.* 18(1–2): 33–55; Kawasaki et al. (1993) *Methods Enzymol.* 218:369–381), and automated large scale HLA class II typing. A common drawback to these methods, however, is the relatively long assay times needed—generally one to two days—and their relatively high complexity and resulting high cost. In addition, the necessity for sample transfers and washing steps increases the chances that small amounts of amplified DNA might be carried over between samples, creating the risk of false positives.

More recently, a molecular typing method using sequence specific primer amplification (PCR-SSP) has been described (see, Olerup and Zetterquist (1992) *Tissue Antigens* 39: 225–235). This PCR-SSP method is simple, useful and fast relative to PCR-SSO, since the detection step is much simpler. In PCR-SSP, allelic sequence specific primers amplify only the complementary template allele, allowing genetic variability to be detected with a high degree of resolution. This method allows determination of HLA type simply by whether or not amplification products (collectively called an "amplicon") are present or absent following PCR. In PCR-SSP, detection of the amplification products is usually done by agarose gel electrophoresis followed by ethidium bromide (EtBr) staining of the gel. Unfortunately, the electrophoresis process takes a long time and is not very suitable for large number of samples, which is a problem since each clinical sample requires testing for many potential alleles. Gel electrophoresis also is not easily adapted for automatic HLA-DNA typing.

Another HLA typing method is SSCP—Single-Stranded Conformational Polymorphism. Briefly, single stranded PCR products of the different HLA loci are run on non-denaturing Polyacrylamide Gel Electrophoresis (PAGE). The single strands will migrate to a unique location based on their base pair composition. By comparison with known standards, a typing can be deduced. It is the only method that can determine true homozygosity. However, many PAGE have to be run and many controls have to be run to make it a viable typing method. This method is very time consuming, labor intensive, and not really suited for large volume analysis.

In view of the foregoing, what is needed in the art is a method of determining genomic information from a highly polymorphic system such as the HLA class I and class II regions. The present invention provides a highly accurate and efficient HLA class I and class II sequence-based typing method that is rapid, reliable and completely automatable.

SUMMARY OF THE INVENTION

The present invention provides new and improved methods for HLA typing. In addition, the methods eliminate the reliance on agarose gel electrophoresis usage for the sequence specific primer (SSP) method for performing HLA DNA typing and obviates the reliance on using cumbersome blot membranes for sequence-specific oligonucleotide probe hybridization (SSO) as well as many of the human errors associated with manual interpretation of bands and assignment of alleles. Thus, the methods of the present invention decrease significantly the number of human errors and the amount of time and effort it takes to perform DNA HLA typing.

In certain aspects, the present invention provides a method of detecting amplified DNA in which the risks of sample cross-contamination and resulting false positive results are reduced. In addition, the present invention provides methods that can allow for reliable, rapid analysis of multiple samples. Moreover, the present invention provides a method of detecting amplified DNA that is relatively simple, and results in a relatively low cost per analysis and is amenable to automation and high throughput matching.

In one aspect, the present invention provides methods for identifying an HLA genotype of a subject. The method involves (a) obtaining a sample containing a template nucleic acid from said subject; (b) amplifying the template nucleic acid with a plurality of HLA allele-specific forward primers and HLA allele-specific reverse primers to form amplification products, wherein the forward primers or reverse primers comprise a detectable label; (c) hybridizing the amplification products with a plurality of HLA locus-specific capture oligonucleotides immobilized on a solid phase to form a plurality of detectable complexes; and (d) detecting the detectable complexes to identify the HLA genotype of the subject.

Another aspect of the present invention provides methods for identifying an HLA genotype of a subject that involves (a) obtaining a sample containing a template nucleic acid from the subject; (b) amplifying the template nucleic acid with a plurality of HLA allele-specific forward primers and HLA allele-specific reverse primers to form amplification products, wherein the forward primers or reverse primers contain a detectable label; (c) hybridizing the amplification products with a plurality of HLA locus-specific capture oligonucleotides to form a plurality of detectable complexes; (d) immobilizing the detectable complexes on a solid phase; and (e) detecting the detectable complexes to identify the HLA genotype of the subject.

In yet another aspect of the invention, methods for identifying an HLA genotype of a subject is provided that involves: immobilizing a plurality of HLA allele-specific reverse primers on a solid phase; amplifying the template nucleic acid with a plurality of HLA allele-specific forward primers and the immobilized reverse HLA allele-specific reverse primers to form amplification products; and detecting the amplification products to identify the HLA genotype of the subject.

In certain embodiments of the present invention, template nucleic acid that is isolated from blood or cord blood is amplified. The template nucleic acid can be any gene derived sequences, including, but not limited to cDNA and genomic DNA.

In certain embodiments, oligonucleotides are immobilized on a solid phase. Examples of solid phase include, but are not limited to: a bead, a chip, a microtiter plate, a polycarbonate microtiter plate, polystyrene microtiter plate, and a slide. The methods of the present invention can be also used to determine class I and class II HLA genotypes. In certain embodiments, HLA allele-specific forward primers and HLA allele-specific reverse primers are used to amplify the template nucleic acid to generate amplification products. In some embodiments, the HLA allele-specific primers are selected from primers denoted as SEQ ID NOS:1–160 and SEQ ID NOS: 169–269.

In some embodiments of the invention, capture oligonucleotides are employed. In certain preferred embodiments, locus-specific capture oligonucleotides are used in the HLA genotyping methods and can be selected from the primers such as SEQ ID NOS: 272–277 and SEQ ID NOS:165–168. The capture oligonucleotides can be modified with a moiety that aids in immobilizing the capture oligonucleotide to a solid phase. In certain embodiments, moieties such as a 5' amine group or a $5'(T)_{5-20}$ oligonucleotide sequence are utilized.

Detectable labels can be used with certain embodiments of the present invention. Examples of a detectable label, include, but are not limited to a radioactive moiety, a fluorescent moiety, a chemiluminescent moiety, an antigen, or a binding protein. In certain embodiments, fluorescent moieties such as fluorescein or 5-(2'-aminoethyl) aminonaphtalene-1-sulfonic acid (EDANS) are attached to oligonucleotides to facilitate detection.

These embodiments as well as additional objects and advantages will become more readily apparent when read with the accompanying FIGURE and detailed description which follows.

DEFINITIONS

An "allele" is one of the different nucleic acid sequences of a gene at a particular locus on a chromosome. One or more genetic differences can constitute an allele. Examples of HLA allele sequences are set out in Mason and Parham (1998) *Tissue Antigens* 51: 417–66, which list HLA-A, HLA-B, and HLA-C alleles and Marsh et al. (1992) *Hum. Immunol.* 35:1, which list HLA Class II alleles for DRA, DRB, DQA1, DQB1, DPA1, and DPB1.

A "locus" is a discrete location on a chromosome that constitutes a gene. Exemplary loci are the class I MHC genes designated HLA-A, HLA-B and HLA-C; nonclassical class I genes including HLA-E, HLA-F, HLA-G, HLA-H, HLA-J and HLA-X, MIC; and class II genes such as HLA-DP, HLA-DQ and HLA-DR.

A method of "identifying an HLA genotype" is a method that permits the determination or assignment of one or more genetically distinct HLA genetic polymorphisms.

The term "amplifying" refers to a reaction wherein the template nucleic acid, or portions thereof, are duplicated at least once. Unless specifically stated "amplifying" may refer to arithmetic, logarithmic, or exponential amplification. The amplification of a nucleic acid can take place using any nucleic acid amplification system, both isothermal and thermal gradient based, including but not limited to, polymerase chain reaction (PCR), reverse-transcription-polymerase chain reaction (RT-PCR), ligase chain reaction (LCR), self-sustained sequence reaction (3SR), and transcription mediated amplifications (TMA). Typical nucleic acid amplification mixtures (e.g., PCR reaction mixture) include a nucleic acid template that is to be amplified, a nucleic acid polymerase, nucleic acid primer sequence(s), and nucleotide triphosphates, and a buffer containing all of the ion species required for the amplification reaction.

An "amplification product" is a single stranded or double stranded DNA or RNA or any other nucleic acid products of isothermal and thermal gradient amplification reactions that include PCR, TMA, 3SR, LCR, etc.

The phrase "template nucleic acid" refers to a nucleic acid polymer that is sought to be copied or amplified. The "template nucleic acid(s)" can be isolated or purified from a cell, tissue, animal, etc. Alternatively, the "template nucleic acid(s)" can be contained in a lysate of a cell, tissue, animal, etc. The template nucleic acid can contain genomic DNA, cDNA, plasmid DNA, etc.

An "HLA allele-specific" primer is an oligonucleotide that hybridizes to nucleic acid sequence variations that define or partially define that particular HLA allele.

An "HLA locus-specific" primer is an oligonucleotide that permits the amplification of a HLA locus sequence or that can hybridize specifically to an HLA locus.

A "forward primer" and a "reverse primer" constitute a pair of primers that can bind to a template nucleic acid and under proper amplification conditions produce an amplification product. If the forward primer is binding to the sense strand then the reverse primer is binding to antisense strand. Alternatively, if the forward primer is binding to the antisense strand then the reverse primer is binding to sense strand. In essence, the forward or reverse primer can bind to either strand as long as the other reverse or forward primer binds to the opposite strand.

The term "detectable label" refers to a moiety that is attached through covalent or non-covalent means to an oligonucleotide. A "detectable label" can be a radioactive moiety, a fluorescent moiety, a chemiluminescent moiety, etc.

The term "fluorescent label" refers to label that accepts radiant energy of one wavelength and emits radiant energy of a second wavelength.

The phrase "hybridizing" refers to the binding, duplexing, or hybridizing of a molecule only to a particular nucleotide sequence or subsequence through specific binding of two nucleic acids through complementary base pairing. Hybridization typically involves the formation of hydrogen bonds between nucleotides in one nucleic acid and complementary sequences in the second nucleic acid.

The phrase "hybridizing specifically" refers to hybridizing that is carried out under stringent conditions.

The term "stringent conditions" refers to conditions under which a capture oligonucleotide, oligonucleotide or amplification product will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the capture oligonucleotides are occupied at equilibrium). Typically, stringent conditions will be those in which the salt concentration is at most about 0.01 to 1.0 M $Na^+$ ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide. An extensive guide to the hybridization and washing of nucleic acids is found in Tijssen (1993) *Laboratory Techniques in biochemistry and molecular biology—hybridization with nucleic acid probes parts I and II,* Elsevier, N.Y., and, Choo (ed) (1994) *Methods In Molecular Biology Volume* 33—*In Situ Hybridization Protocols Humana* Press Inc., New Jersey; Sambrook et al., *Molecular Cloning, A Laboratory Manual* ($2^{nd}$ ed. 1989); *Current Protocols in Molecular Biology* (Ausubel et al., eds., (1994)).

The term "complementary base pair" refers to a pair of bases (nucleotides) each in a separate nucleic acid in which each base of the pair is hydrogen bonded to the other. A "classical" (Watson-Crick) base pair always contains one purine and one pyrimidine; adenine pairs specifically with thymine (A-T), guanine with cytosine (G-C), uracil with adenine (U-A). The two bases in a classical base pair are said to be complementary to each other.

"Bind(s) substantially" refers to complementary hybridization between a capture nucleic acid and a target nucleic acid and embraces minor mismatches that can be accommodated by reducing the stringency of the hybridization media to achieve the desired detection of the target polynucleotide sequence.

The term "capture oligonucleotide" refers to a nucleic acid sequence or nucleic acid subsequence that can hybridize to another oligonucleotide, amplification product, etc. and has the ability to be immobilized to a solid phase. A capture oligonucleotide typically hybridizes to at least a portion of an amplification product containing complementary sequences under stringent conditions.

A "HLA locus-specific capture oligonucleotide" is a capture oligonucleotide that is complementary to and hybridizes to a conserved region of an HLA locus. For example a "HLA locus-specific capture oligonucleotide" that is specific for the HLA-A locus will hybridize to one or more conserved regions or subsequences of the HLA-A locus.

A compound is "immobilized on a solid phase" when it is directly or indirectly attached to the solid phase. Such immobilization may be through covalent and/or non-covalent bonds.

The term "corresponding nucleotide," is used to refer to the position of a nucleotide in a first nucleic acid by reference to a second nucleic acid. Thus, a corresponding nucleotide refers to a nucleotide that it is positionally located opposite to a base where neighboring bases are all hybridized pairs.

"Subsequence" refers to a sequence of nucleic acids that comprise a part of a longer sequence of nucleic acids.

The term "portions" should similarly be viewed broadly, and would include the case where a "portion" of a DNA strand is in fact the entire strand.

The term "specificity" refers to the proportion of negative test results that are true negative test result. Negative test results include false positives and true negative test results.

The term "sensitivity" is meant to refer to the ability of an analytical method to detect small amounts of analyte. Thus, as used here, a more sensitive method for the detection of amplified DNA, for example, would be better able to detect small amounts of such DNA than would a less sensitive method. "Sensitivity" refers to the proportion of expected results that have a positive test result.

The term "reproducibility" as used herein refers to the general ability of an analytical procedure to give the same result when carried out repeatedly on aliquots of the same sample.

The term "amplicon" is used herein to mean a population of DNA molecules that has been produced by amplification, e.g., by PCR.

The term "molecular beacon," as used herein refers to a molecule capable of participating in a specific binding reaction and whose fluorescence activity changes when the molecule participates in that binding reaction.

DETAILED DESCRIPTION

I. Introduction

The present invention provides methods for HLA genotyping of human leukocyte antigens, as well as other molecular diagnostic protocols relating to the detection of DNA sequences and sequence variations using nucleic acid amplification methods. Advantageously, the methods described herein can be used to detect genetic mutations, detect cancer gene mutations, microbial and cancer drug resistance mutations, detection of viruses, bacteria, fungi, parasites and any other microbes, forensics, parentage, etc.

In particular, the methods of the present invention are useful for determining HLA genotypes of samples from subjects. Such genotyping is important in the clinical arena for the diagnosis of disease, transplantation of organs, and bone marrow and cord blood applications.

In the present invention, allelic-specific HLA primers are used to amplify HLA sequences. In some embodiments, these amplification products can be immobilized to a solid phase using a locus-specific or an allele-specific capture oligonucleotide. In certain embodiments, the locus-specific capture oligonucleotides are preferred as fewer capture oligonucleotides need to be generated to carry out the HLA genotyping. In other embodiments, one HLA-specific primer is immobilized to a solid phase and the target is amplified using another HLA-specific primer that is free in solution. The advantages and details for carrying out the present invention will be discussed more fully below.

II. Materials Used in the Present Invention

Oligonucleotides

Oligonucleotides used in the present invention (e.g., allele and locus-specific oligonucleotides) can be chemically synthesized according to the solid phase phosphoramidite triester method first described by Beaucage & Caruthers, (1981) *Tetrahedron Letts.* 22:1859–1862, using an automated synthesizer, as described in Van Devanter et al., (1984) *Nucleic Acids Res.* 12: 6159–6168. Purification of oligonucleotides is typically by either native acrylamide gel electrophoresis or by anion-exchange HPLC as described in Pearson & Reanier, (1983) *J. Chrom.* 255:137–149.

HLA allele-specific Primers

The HLA allele-specific primers used in the present invention are designed to amplify HLA allele sequences. Since 1995, 213 class I (HLA-A, HLA-B, and HLA-C) and 256 class II (HLA-DR, HLA-DP, and HLA-DQ) alleles had been identified and sequenced (see e.g., Krausa and Browning (1996) *Detection of HLA gene polymorphism* in Browning M, McMichael A, ed. *HLA and MHC: genes, molecules and function.* Oxford: Bios Scientific Publishers Limited, pp. 113–138), with new alleles being discovered all the time. The sequences of many of these alleles are publicly available through GenBank and other gene databases and have been published (see e.g., Mason and Parham (1998) *Tissue Antigens* 51: 417–66, listing HLA-A, HLA-B, and HLA-C alleles; Marsh et al. (1992) *Hum. Immunol.* 35:1, listing HLA Class II alleles—DRA, DRB, DQA1, DQB1, DPA1, and DPB1). Also, the use of allele-specific primers (sequence-specific primers (SSP)) has permitted the specific amplification of HLA allele sequences (see e.g., Bunce and Welsh (1994) *Tissue Antigens* 43: 7–17, amplification of HLA-C alleles; Bunce et al. (1995) *Tissue Antigens* 46: 355–67, amplification of HLA-A.B.C. DRB1, DRB3, DRB4, DRB5 & DQB1 alleles with sequence-specific primers; Gilchrist et al. (1998) *Tissue Antigens* 51: 51–61, HLA-DP typing with sequence specific primers).

In the design of the HLA primer pairs for the primer mixes, primers were selected based on the published HLA sequences available in the literature. A chart of the HLA alleles and sequences was examined and the polymorphic sites were identified. Then pairs of primers were selected that would produce PCR products to a group of HLA alleles. The sequence specific nucleic acid amplification reaction typically uses at least a pair of PCR primers for each allele, both of which contain the discriminating sequences with at least one or more of the changed nucleotides at the 3' end of each PCR primer. Since the 3' end is the end where polymerization takes place, if a mismatch occurs due to sequence non-complementarily, nucleic acid amplification will take place and one would not expect a "false positive." However, if a match occurs, then the amplification can proceed. For example, HLA class I allele-specific primers and HLA class II allele-specific primers are listed in Table 1 (SEQ ID NOS: 1–160) and 2 (SEQ ID NOS: 169–269), respectively. Examples of control primers listed in Table 1 are CI53 (SEQ ID NO: 161), CI54 (SEQ ID NO: 162), CI148 (SEQ ID NO: 163), and CI149 (SEQ ID NO: 164). Examples of control primers listed in Table 2 are DPA-E(PC) (SEQ ID NO: 270), and DPA-F (PC) (SEQ ID NO: 271). The Class I primers are selected to amplify Class I exon 2 and exon 3 products. The Class II primers are selected to amplify Class II exon 2 products. In certain embodiments, the primers listed in Tables 3 and 4 are used as exemplary groups of primer pairs and the HLA specificities these pairs can identify after successful positive PCR amplifications with the appropriate DNA templates for HLA class I and II alleles respectively.

By utilizing a pair of primers, each PCR reaction identifies two sites of polymorphism and therefore increases the specificity of the reaction. Those of skill in the art will recognize a multitude of oligonucleotide compositions that can be used as HLA allele-specific primers to specifically amplify HLA allele sequences. In addition, customized sets of HLA-specific primers can be created to cater to detection of the allele distribution for various ethnicities or racial groups by simply changing the primer pair combinations. In this manner, detection of new alleles can be easily added to the methods of the present invention.

Capture Oligonucleotides

In certain embodiments, the invention involves locus-specific capture oligonucleotides or allele-specific capture oligonucleotides. Locus-specific oligonucleotide can hybridize to a conserved region in a HLA locus; a locus-specific capture oligonucleotide has the ability to hybridize to some or all of the sequences that can be generated by the amplification of HLA allele sequences using HLA-specific primers. Locus-specific sequences have been identified in HLA loci. For example, locus-specific sequences for HLA-class I genes have been delineated in the first and third introns flanking the polymorphic second and third exons (see e.g., Cereb et al. (1995) *Tissue Antigens* 45: 1–11). The capture oligonucleotides should be of such length and composition so as to be able to hybridize with the allele-specific PCR products. In certain embodiments, HLA locus-specific class I capture oligonucleotides contain the following sequences: for HLA-A (CICptA1, Class I Capture Oligo A1, 5'ACGCCTACGACGGCAAGGATTACATCGCCC3' (SEQ ID NO:165); and CICptA2, Class I Capture Oligo A2, 5'GATGGAGCCGCGGTGGATAGAGCAGGAGGG3' (SEQ ID NO:166), for HLA-B (CICptB1, Class I Capture Oligo B1, 5'CAGTTCGTGAGGTTCGACAGCGACGCC3' (SEQ ID NO:167), and CICptB2, Class I Capture Oligo B2, 5'CTGCGCGGCTACTACAACCAGAGCGAGGCC3' (SEQ ID NO:168). In other embodiments, HLA locus-specific class II capture oligonucleotides contain the following sequences: for HLA-DQ (DQCPT1, 5'CACGTCGCTGTCGAAGCGCACGTACTCCTC3' (SEQ ID NO:272); DQCPT2, 5'CACGTCGCTGTC-GAAGCGGACGATCTCCTT3' (SEQ ID NO:273); DQCPT3, 5'CACGTCGCTGTCGAAGCGTGCGTACTC-CTC3' (SEQ ID NO:274); DQCPT4, 5'CACGTCGCTGTC-GAAGCGCGCGTACTCCTC3' (SEQ ID NO:275); and DQCPT5, 5'CACGTCGCTGTCGAAGCGCACGTCC TCCTC3'(SEQ ID NO:276), for HLA-DR (DRCPT1, DRCP, 5'TGGCGTGGGCGAGGCAGGGTAACT-TCTTTA3' (SEQ ID NO:277)). In certain embodiments, it may require the use of more than one capture oligonucleotide to hybridize to all of the HLA allele amplification products.

Modification of Oligonucleotides

In certain embodiments of the present invention, oligonucleotides are modified or synthesized as modified oligonucleotides to facilitate immobilization or detection.

Immobilization Modifications

In certain embodiments, where capture oligonucleotides are used or where an immobilized amplification primer is used, it is desirable to modify the particular oligonucleotide to affix it to a solid phase or support. It is desired that the modification of the capture oligonucleotide does not interfere with its ability to bind to an HLA allele-specific amplification product. Those of skill in the art will recognize a variety of methods to immobilize oligonucleotides to a solid phase. For example, oligonucleotides can be directly or indirectly immobilized on a solid phase. The oligonucleotides can be immobilized directly to the solid phase through covalent and non-covalent bonds. For example, the 5' end of an oligonucleotide can be synthesized with an amine moiety (see Kawasaki et al. (1993)). In certain embodiments, an amine moiety with a C6 carbon spacer is conjugated to the 5' end of a capture oligo or amplification primer. The amine-modified primers are affixed to the surface of a substrate such a Biodyne C membrane (Pall Biosupport) (Kawasaki et al. (1993)) or through a commercially available microtiter plate (e.g., Xenobind™ (Covalent Binding Microwell Plates), Xenopore, Hawthorne, N.J.). Alternatively a polythymidine (polyT) stretch can be added to an oligonucleotide by terminal deoxyribonucletotidyltransferase (Saiki et al. (1989)). Such a polyT stretch can be fixed to many solid substrates (e.g., nylon) using UV light leaving the rest of the oligonucleotide free to hybridize to another nucleic acid. Preferably, the polyT stretch is from 5 to 20 T's.

Alternatively, the oligonucleotides can be indirectly bound to the solid phase by coating the solid phase with a substance or molecule that can bind to the oligonucleotides. Biotinylated oligonucleotides can also be used as capture oligonucleotides. Methods are known in the art for synthesizing biotinylated oligonucleotide (e.g., by synthesizing a primer with a biotinylated 5' end nucleotide as the terminal residue) (see e.g., Innis et al. (1990)). Biotinylated oligonucleotides can be affixed to a substrate that is coated with avidin.

A high density array of capture oligonucleotides or amplification primers can be also synthesized on a substrate by attaching photoremovable groups to the surface of a substrate, exposing selected regions of the substrate to light to activate those regions, attaching a nucleic acid monomer with a photoremovable group to the activated regions, and repeating the steps of activation and attachment until probes of the desired length and sequences are synthesized. (See, e.g., Fodor et al. (1991) *Science* 251: 767–773 and U.S. Pat. No. 5,143,854). The resulting array of oligonucleotides can then be used to in the methods of the present invention.

A variety of solid supports or phases can be used in the present invention. Examples of solid supports include, without limitation, bead, microtiter plates, and chips. Beads can be composed of materials such as Sepharose, agarose, polystyrene, etc. and can be paramagnetic. Microtiter plates are commercially available in a variety of formats (e.g., 96, 384 and 1536 well plates) and materials (e.g., polystyrene). The plates can be either polycarbonate plates in which case the thermal gradient nucleic acid amplification reaction (such as PCR) can happen directly in the well or polystyrene in which case the thermal gradient nucleic acid amplification reaction (such as PCR) has to take place in a separate polycarbonate plate and transferred to the surface modified and oligonucleotide attached plate. Isothermal nucleic acid amplification methods can be conducted in polystyrene plates. chips can be comprised of a variety of materials, layers and substrates. Polymers which may be used as solid supports or phases include, but are not limited to, the following: polystyrene; poly(tetra)fluoroethylene (PTFE); polyvinylidenedifluoride; polycarbonate; polymethylmethacrylate; polyvinylethylene; polyethyleneimine; poly (etherether)ketone; polyoxymethylene (POM); polyvinylphenol; polylactides; polymethacrylimide (PMI); polyatkenesulfone (PAS); polypropylene; polyethylene; polyhydroxyethylmethacrylate (HEMA); polydimethylsiloxane; polyacrylamide; polyimide; and block-copolymers. The solid support on which an oligonucleotide resides may also be a combination of any of the aforementioned solid support materials.

Oligonucleotides Containing Detectable Labels

Detectable labels can also be attached to oligonucleotides to facilitate detection of the oligonucleotide in an analyte. Detectable labels can be detected either directly or indirectly, by spectroscopic, photochemical, biochemical, immunochemical, or chemical means. For example, useful labels include radiolabels (e.g., $^{3}H$, $^{13}C$, $^{14}C$, $^{32}P$, $^{35}S$, $^{125}I$, etc.), fluorescent dyes, fluorophores, fluorescent moieties, chemiluminescent moieties, electron-dense reagents, enzymes and their substrates (e.g., as commonly used in enzyme-linked immunoassays, e.g., alkaline phosphatase and horse radish peroxidase), biotin-streptavidin, digoxigenin, or haptens and proteins for which antisera or monoclonal antibodies are available. The label or detectable moiety is typically bound, either covalently, through a linker or chemical bound, or through ionic, van der Waals or hydrogen bonds to the molecule to be detected.

The detectable label should be stable to the amplifications conditions used and should permit direct or indirect detection. Indirect detection often involves the presence of one or more detection reagents. For example, one detectable label, biotin can be detected using an avidin conjugate such as avidin conjugated to an enzyme such as peroxidase (e.g., HRP), and a colorimetric substrate for peroxidase (e.g., TMB). The formation of colorimetric product can easily be detected using a spectrophotometer. For example, in certain embodiments, the primers listed in Tables 5 and 6 are biotinylated.

In certain embodiments, oligonucleotides comprising a quencher and a fluorophore moiety (molecular beacons) are contemplated. Molecular Beacons are single stranded oligonucleotide probes designed to have hairpin configuration by virtue of the presence of five to seven complementary nucleotides at their termini. The loop portion (10–40 nucleotides) is chosen so that the probe-amplification product hybrid is stable at the annealing temperature. The length of the arm sequences (5–7 nucleotides) is chosen so that a stem is formed at the annealing temperature of the polymerase chain reaction. Also the stem or arm sequence must be designed to ensure that the two arms hybridize to each other but not to the probe sequence. One end would carry a fluorophore (e.g. 5-(2'-aminoethyl)aminonaphtalene-1-sulfonic acid (EDANS) and the other a quencher (e.g. 4-(4'-dimethylaminophenylazo)benzoic acid (DABCYL). When a probe is not hybridized to its complementary target sequence, the hairpin folding reaction would take place and fluorescence does not occur due to quenching. Quenching occurs because the energy given off as light during fluorescence is transferred to the quencher and dissipated as heat. Since the energy is released as heat instead of light, the fluorescence is said to be quenched. However, if a complementary target sequence is present, hybridization to the target sequence would be favored over the internal hairpin due to the increased stability as a result of the longer stretches of complementary sequence. The hairpin would open up thus allowing for release of quenching and the probes to fluoresce. In the fluorophore-quencher pair example given above, when stimulated by UV light with a peak wavelength of 336 nm, EDANS emits a brilliant blue fluorescence with a peak wavelength of 490 nm. (Tyagi et al., (1996) *Nature Biotechnology* 14: 303–308; Tyagi et al. (1998) *Nature Biotechnology* 16:49–53; Paitek et al. (1998) *Nature Biotechnology* 16: 359–63; Kostrikis et al. (1998) *Science* 279:1228–1229).

III. Source of HLA Gene Sequences

The template HLA DNA sequences are contained in samples containing nucleic acid (e.g., DNA, RNA, etc.), which are obtained from a biological source. In certain embodiments, the nucleic acid is isolated from a biological source containing HLA gene sequences. The nucleic acid may be from any species having HLA gene sequences, which include but are not limited to, a human, a chimpanzee, a simian, a mouse, etc. Methods are known for lysing biological samples and preparing extracts or purifying DNA, RNA, etc. See, *Current Protocols in Molecular Biology* (Ausubel et al., eds., 1994)). In some embodiments, the biological source is blood, and is more preferably cord blood (e.g., blood from an umbilical cord). In methods involving cord blood or blood, two isolation procedures are preferred: Salt extraction with ethanol precipitation; and the Qiagen QIAamp® isolation method. For the salt extraction method, the cells are first lysed and centrifuged. Then water is added and the sample is centrifuged again. The pellet is digested with Proteinase K. The DNA is then extracted by the addition of 6M Guanidine HCl and incubation at 70° C. for several minutes. The sample is centrifuged again and the supernatant is precipitated with cold 95% Ethanol. The pellet is then dried and resuspended in the appropriate buffer.

RNA template sequences that are amplified using the methods and compositions of the present invention may be a single RNA template or different RNA templates. The RNA can be isolated as total RNA from a cell, bacterium, virus etc. See, Ausubel et al. The total RNA may be subsequently purified as poly A+RNA or purified in a different manner to isolate certain species of interest. See Ausubel et al. Alternatively, the template RNA can be transcribed in vitro and used in the present invention. The RNA template sequence could also be reverse transcribed into cDNA and used as a nucleic acid template in the methods of the present invention.

IV. Amplification of HLA Gene Sequences from Nucleic Acid

The methods of the present invention involve the direct or indirect detection of HLA gene sequences that have been amplified from DNA or reverse transcribed DNA. To amplify the desired nucleic acid for HLA gene sequences, the following are usually present in the reaction vessel: template nucleic acid, nucleic acid polymerase, a molar excess of dNTPs, an antisense primer(s), and a sense-primer(s), for copying a HLA gene sequence from a template nucleic acid. Preferably, the reaction can be carried out in a thermal cycler oven to facilitate incubation times at the desired temperatures.

Reaction Components

Oligonucleotide Primers

The oligonucleotides that are used in the present invention, as well as oligonucleotides designed to detect amplification products, can be chemically synthesized as described above. These oligonucleotides can be labeled with radioisotopes, chemiluminescent moieties, or fluorescent moieties, etc. in a covalent or non-covalent manner. Such labels are useful for the characterization and detection of amplification products using the methods and compositions of the present invention.

Buffer

Buffers that may be employed are borate, phosphate, carbonate, barbital, Tris, etc. based buffers. See Rose et al., U.S. Pat. No. 5,508,178. The pH of the reaction should be maintained in the range of about 4.5 to about 9.5. See U.S. Pat. No. 5,508,178. The standard buffer used in amplification reactions is a Tris based buffer between 10 and 50 mM with a pH of around 8.3 to 8.8. See Innis et al. (1990). In certain embodiments of the invention, a preferred buffer for the present invention is 150 mM Tris-HCl pH 8.8 for the amplification of class I HLA sequences and 20 mM Tris HCl pH 8.8 for class II HLA sequences.

Salt Concentration

The concentration of salt present in the reaction can affect the ability of primers to anneal to the template nucleic acid. See Innis et al. (1990). For example, potassium chloride can be added up to a concentration of about 50 mM to the reaction mixture to promote primer annealing. Sodium chloride can also be added to promote primer annealing. See Innis et al. (1990). In certain embodiments of the invention, the preferred salts are 30 mM Ammonium Chloride for class I HLA sequences and 100 mM KCl for class II sequences.

Magnesium Ion Concentration

The concentration of magnesium ion in the reaction can be critical to amplifying the desired sequence(s). See Innis et al. (1990). Primer annealing, strand denaturation, amplification specificity, primer-dimer formation, and enzyme activity are all examples of parameters that are affected by magnesium concentration. See Innis et al. (1990). Amplification reactions should contain about a 0.5 to about a 5 mM magnesium concentration excess over the concentration of dNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the template nucleic acid(s) and the primers being used, among other parameters. In certain embodiments of the invention, the preferred magnesium concentrations are 4 mM $MgCl_2$ and 3.4 mM $MgCl_2$, for class I HLA sequences and class II HLA sequences, respectively.

Deoxyribonucleotide Triphosphate Concentration

Deoxyribonucleotide triphosphates (dNTPs) are added to the reaction to a final concentration of about 20 $\mu$M to about 300 $\mu$M. Each of the four dNTPs (G, A, C, T) should be present at equivalent concentrations. See Innis et al. In certain embodiments, 166 $\mu$M dNTP is the preferred concentration of nucleotides.

Nucleic Acid Polymerase

A variety of DNA dependent polymerases are commercially available that will function using the methods and compositions of the present invention. For example, Taq DNA Polymerase may be used to amplify template DNA sequences. Also, a reverse transcriptase can be used in certain embodiments of the present invention. Reverse transcriptases, such as the thermostable C. therm polymerase from Roche, are also widely available on a commercial basis.

Other Agents

Assorted other agents or compounds are sometime added to the reaction to achieve the desired results. For example, DMSO can be added to the reaction, but is reported to inhibit the activity of Taq DNA Polymerase. However, DMSO has been recommended for the amplification of multiple template sequences in the same reaction. See Innis et al. Stabilizing agents such as gelatin, bovine serum albumin, and non-ionic detergents (e.g. Tween-20) are commonly added to amplification reactions. See Innis et al. For the amplification of class II sequences, the addition of 0.2% Triton X-100 has been found to be preferred. In addition, to enhance specificity by decreasing spurious priming, methods that incorporate "hot start" (e.g., AmpliWax® (Applied Biosystems, Inc.), or an monoclonal antibody to Taq polymerase (CLONTECH Laboratories, Inc.) can be used to increase the specificity of an amplification reaction.

Amplification Programs

To amplify the HLA gene sequences of interest, the amplification reaction mixture is subjected to a series of temperatures to repeatedly denature the nucleic acid, anneal the oligonucleotide primers, and extend the primers with the polymerase. The use of a thermal cycling device can greatly facilitate the temperature cycling required in certain embodiments of the present invention. The optimum denaturing, annealing and extending temperatures can be determined by one of skill in the art for a particular oligonucleotide primer pair(s) and HLA gene template(s). In general, the extension step is carried out at a temperature of about 72° C. and the denaturing step is carried out at about 96° C. In addition, it may be necessary to carry out different sets of amplification cycles in succession to achieve the desired results. In addition, the number of cycles is an important consideration. Typically, one of skill in the art can carry out experiments to determine what is the optimum number of cycles to amplify the desired template(s).

The annealing temperature is of critical importance in any amplification reaction. If the annealing temperature is too low, non-specific amplification of undesired templates can arise. If the annealing temperature is too high, the template may not be efficiently amplified if at all. Determining the optimum annealing temperature for in reactions that involve large numbers of different oligonucleotide sequences and HLA templates is particularly important. A preferred amplification program for amplifying template HLA gene sequences where both primers are in solution is the following 6-stage program:

| | | |
|---|---|---|
| 1.) | 1 Cycle | 97° C. for 20 seconds |
| 2.) | 5 Cycles | 97° C. for 35 seconds, 61° C. for 45 seconds, 72° C. for 40 seconds |
| 3.) | 25 Cycles | 97° C. for 20 seconds, 59° C. for 45 seconds, 72° C. for 40 seconds |
| 4.) | 4 Cycles | 97° C. for 20 seconds, 57° C. for 45 seconds, 72° C. for 90 seconds |
| 5.) | 1 Cycle | 72° C. for 4 minutes |
| 6.) | 1 Cycle | 30° C. for 1 second. |

A number of controls can be used in the amplification methods described herein. They include, but are not limited to: 1. Omission of Primers—Control of spurious priming; 2. Known negative control—Control of specificity; 3. Known positive control—Control of sensitivity; 4. Omission of DNA Polymerase—Detection of nonspecific probe and/or enzyme/antibody sticking; 5. Use of irrelevant probes for hybridization—Control for hybridization; 6. Amplification of endogenous control DNA sequence—Detection of false negatives, control of DNA/RNA quality.

V. Washing

After a hybridization step or after solid-phase PCR (e.g., amplification with an immobilized primer), a solid phase can be washed with a buffer to decrease non-specific binding, to wash away unbound primers, or to provide a solution that is more appropriate for subsequent detection of a detectable label, etc. Where an oligonucleotide has been immobilized or hybridized to an oligonucleotide on a solid support, the unbound oligonucleotides can be washed from a bound complex using variety of separation methods known in the art. There are many separation methods known in the art (e.g., filtering, sedimenting, centrifuging, decanting, precipitation, etc.) that can be used or adapted for use in the present invention. For example, where the amplification product is immobilized on a microtiter plate, the unbound oligonucleotides can be aspirated from the well, leaving behind those amplification products, HLA allele sequences, etc. that are bound to a solid phase. Another separation method is the immobilization of an amplification product, HLA allele sequence, etc. on a paramagnetic bead, and the decantation or aspiration of the unbound primers and oligonucleotides leaving behind the bound complex containing a detectable label remaining on the solid phase. Commercial kits, methods and systems are commercially available and can be adapted or used with the present invention (e.g., the KingFisher™ system from Thermo Labsystems, Inc.).

A wash buffer can contain a detergent, or other agents, and compositions that are compatible with retention of the bound complex on the solid phase. A blocking agent is generally present in the wash buffer. Blocking agents include, but are not limited to non-fat dry milk, herring sperm DNA, dextran sulfate, and BSA. For example, a wash buffer that can be used in the present invention is a solution of 0.1% BSA in PBS. The use of 0.1% BSA results in optimum results. One or more washes may be necessary to achieve optimum lowering of non-specific binding.

VI. Detection

A wide range of methods can be used to detect the presence of oligonucleotides that contain a detectable label. The method of detection depends on the nature of the detectable label that is present. If the label is directly or indirectly capable of generating a signal in the visible light range, then a spectrophotometer can be used. Similarly, a fluorescent detectable label or signal generated therefrom can be measured using a fluorescent spectrophotometer. Alternatively, luminometers can be used to measure chemiluminescent signals. Isotopic labels can be measured using a liquid scintillation counter or in some cases—x-ray film. In certain embodiments, it is preferred to use a spectrophotometric plate reader that can read microtiter plates in an automated system.

VII. Analysis of Results of Assays

Computer programs containing algorithm(s) can be used to score, interpret and assign HLA alleles in certain embodiments of the present invention. Briefly, the data from a detection instrument (e.g., a spectrophotometer, an ELISA reader, a scintillation counter, etc.) can be analyzed through the use of a computer program that compares the values of each sample against a reference value(s).

For example, computer programs for the ELISA format readers take readings below a designated threshold and label such as negative and values above the same thresholds as positives. A positive well or a combination of certain wells would then represent a specific gene sequence or allele and be scored as such with the automated program. The optical density (O.D.) values obtained from reading of the wells of the ELISA plate readers are given as numerical values ranging from 0.000–2.000. This information is automatically downloaded onto the attached computers via the vendor provided software. The O.D. values are saved in a spreadsheet format in the vendor provided program as raw data.

The first step in computer analysis of the data is to validate and assign the negative control reading from the negative control well, which always exists in the same well location on the plate. A properly performed negative control is assigned as the negative value. In some embodiments where peroxidase is used with TMB, negative controls are deemed properly performed when the O.D. values are below 0.2. The usual O.D. values of a negative control reaction yielding colorless products are usually between 0.05 and 0.1. Then the threshold level is determined for that particular reaction to be 3.5 times the value of the negative control. A well is considered weakly positive if the reaction yields an O.D. reading that exceeds 3.0-fold but is below 3.5-fold of the negative control reading. A weakly positive well is rejected if two other strongly positive alleles are present for that locus. In the absence of two other strongly positive alleles for each locus, the weakly positive well is accepted if it is confirmed with repeat testing or alternative methods. A truly positive well is assigned when the O.D. readings exceed 3.5-fold over the value of the negative control. The computer program analyzes the results of all the wells, determines the positive wells based on the established criteria, and assigns the alleles based on which primer pairs exist in the positive wells. If more than two alleles are identified per locus, then the results have to be analyzed using the following protocol and confirmed by repeat testing or alternative methods.

By storing numerical reading values for the various primer pairs, many different type of assessment are possible. For example, the effects of the changes in primer pairs and primer sequences on average O.D. readings can be assessed. Consistently weak reacting sets can be replaced with primer pairs giving more robust and consistent results. Alternatively, if a particular weak reacting set of primers have no substitute, then handicap scores can be given. A more consistent tray can be developed by using the reading values as a point of reference.

VIII. High Throughput Methods and Systems

In the present invention, high-throughput analysis of HLA genotypes can be performed using automated devices. For example, an automated workstation (see e.g., U.S. Pat. No. 5,139,744, "Automated laboratory workstation having module identification means") can be used to perform many of the steps involved in the present invention. An "automated workstation" is typically a computer-controlled apparatus which can, through robotic functions, transfer, mix, and remove liquids from microtiter plates. An automated workstation can also contain a built-in plate reader, which can read the absorbance of a liquid in a microtiter well. The automated workstation can be programmed to carry out a series of mixing, transfer, and/or removal steps. The automated workstation will typically have a multi-channel pipettor which can pipette small amounts of liquid (e.g., microliter amounts) from a vessel to the well.

For example, in some embodiments of the present invention, the automated workstation can be used to transfer DNA samples, oligonucleotides, amplification reagents. The automated work station can also be used to wash the samples using wash buffer. In addition, detection of oligonucleotides containing a detectable label can be carried out using an automated workstation. For example, the automated workstation can be used to add a detection reagent to the wells.

The automated workstation, when equipped with a plate reader, can monitor the absorbance of the reaction of the detection reagent in the wells.

A number of robotic fluid transfer systems/automated work stations are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous ligation reactions. Other automatic microplate dispensers include Lambda Jet and Lambda Dot (One Lambda, Inc. CA), and various other automatic plate washers and dispensers (e.g. from Thermo Labsystems, Inc. or Molecular Devices, Inc.). Moreover, it will be apparent to those of skill in the art that the PCR setup, reagent addition and washing steps can be automated with existing robotics outlined above.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip—compatible DOS OS2 WINDOWS, WINDOWS NT or WINDOWS 98 based machines), MACINTOSH, or UNIX based (e.g., SUN work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques. The use of such automated machines, can minimize the existence of false positives, labor requirements, variabilities, human errors, human subjectivity, and human expertise requirements, and maximizes throughput, accuracy, sensitivity and specificity.

IX. Hybridization of Capture Oligonucleotides to HLA Amplification Products

Hybridization of Immobilized Capture Oligonucleotides to HLA Amplification Products This method involves the use of immobilized oligonucleotides to capture HLA allele sequences contained in an amplification product. Briefly, HLA allele sequences are amplified from a template nucleic acid using HLA allele-specific forward and reverse primers. One or both of the amplification primers can contain a detectable label. Then the amplification products are denatured and hybridized to a locus-specific or allele-specific capture oligonucleotide that is already immobilized to a solid phase to form a detectable complex. The presence of the detectable label in the detectable complex is then measured using methods known to those of skill in the art (e.g., spectrophotometric means, a luminometer, etc.), which may require the addition of one or more detection reagents (e.g., an avidin-enzyme molecule with a colorimetric enzyme substrate).

The capture oligonucleotides possess sufficient nucleotide complementarity to the HLA allele sequences being amplified that they can hybridize to them under stringent conditions. Typically, the HLA allele-specific forward and/or reverse primer will contain a detectable label (e.g., biotin, digoxigenin, EDANS, or a fluorescent moiety, etc.) so as to facilitate detection. Thus, this method allows for the amplification of many different HLA alleles which can be detected with, in the case of some HLA loci, as little as one capture oligonucleotide that is locus-specific. This is an advantage over previous methods, in which allele-specific capture oligonucleotides were used, as the detection of hundreds of alleles would require hundreds of allele-specific capture oligonucleotides (see e.g., Erlich et al. (1991) *Eur. J. Immunogenet.* 18(1–2): 33–55; Kawasaki et al. (1993) *Methods Enzymol.* 218:369–381). Thus, the present invention permits a great simplification and reduction in the number of oligonucleotides required to detect hundreds of HLA-alleles.

Hybridization of Free Capture Oligonucleotides to HLA Amplification Products and Subsequent Immobilization of the Detectable Complex In another embodiment of the present invention, the hybridization takes place in solution with capture oligonucleotide(s) and then the capture oligonucleotide is immobilized. This method involves the use of capture oligonucleotides that are hybridized in solution to HLA allele sequences contained in an amplification product and subsequent immobilization of the capture oligonucleotide to a solid phase. First, HLA allele sequences are amplified from a nucleic acid using HLA allele-specific forward and reverse primers. Then the amplification product are denatured and hybridized to a locus-specific or allele-specific capture oligonucleotide that is already immobilized to a solid phase. The capture oligonucleotides then hybridize and bind to the denatured single stranded PCR products at a suitable hybridization temperature and "capture" complementary sequences in the products onto the plate. If none or very little complementary sequences for the capture oligonucleotide are present after the nucleic acid amplification reaction (for example, if the allele sequence represented by the allele-specific PCR primers are not present in the sample DNA template, then no PCR product would be formed), then it is unlikely a detectable complex will form. The capture oligonucleotides possess sufficient nucleotide complementarity to the HLA allele sequences being amplified that they can hybridize to them under stringent conditions. Typically, the HLA allele-specific forward and/or reverse primer will contain a detectable label (e.g., biotin, digoxigenin, EDANS, or a fluorescent moiety, etc.) so as to facilitate detection.

In this method, capture oligonucleotides with either conserved sequences (e.g., locus-specific oligonucleotides) or allele specific sequences can be used. The later offering an additional level of specificity whereas the former offers convenience and ease of setup as well as lower cost in having fewer sets of oligonucleotides. Thus, this method allows for the amplification of many different HLA alleles which can be detected with, in the case of some HLA loci, as little as one capture oligonucleotide that is locus-specific. This is an advantage over previous methods, in which allele-specific capture oligonucleotides were hybridized in solution to a locus-specific HLA amplification product, as the detection of hundreds of alleles would require hundreds of allele-specific capture oligonucleotides (see e.g., Nevinny-Stickel and Albert (1993) *Eur. J. of Immunogenet.,* 20: 419–427). Thus, the present invention permits a great simplification and reduction in the number of oligonucleotides required to detect hundreds of HLA-alleles.

X. Amplification of HLA Sequences with Immobilized Primers

This method involves the amplification of HLA sequences using allele-specific primers, where one of the pair of amplification primers is immobilized to a solid phase. The other primer constituting the primer pair contains a detectable label and is initially free in solution. This technique is not limited to the detection of HLA alleles. Essentially, any set of amplification primers and any gene can be amplified. With this method, the immobilized amplification primer serves to immobilize the amplification product directly to a solid phase. The amplification should only take place if allele that can be amplified with a particular pair of allele-specific primers is present in solution. The nucleic acid amplification and capture of PCR product take place on the same polycarbonate plate and the capture oligonucleotide/PCR primer is an allele specific sequence that identifies the sequence of interest (e.g. the particular HLA allele) and serves three purposes. First, it serves as the capture oligonucleotide and immobilizes the PCR products onto the plates. Second, it serves as one of the PCR primers that facilitate the nucleic acid amplification reaction. Third, it serves as the discriminating sequence that allows identification of the correct allele. This means that the PCR amplification reaction would only take place if the correct sequences that is perfectly complementary to the template (which is the particular allele of the person whose HLA sequence or other sequence is being typed) is present on both PCR primers. An advantage of this method is the elimination of transfer, reduction of an additional set of oligonucleotides to the assay vessel (compared with two previous methods described under Section X).

If a sequence specific nucleic acid amplification reaction occurred due to perfect matching between the PCR primers and the template sequences, then the product would be immobilized on the solid phase. Following capture, the unbound non-specific labeled PCR primers can be washed off. With fluorescent probes, the plate can be read with an automated fluorescent ELISA format reader. With calorimetric reactions that are associated for example with avidin conjugated enzyme and substrate systems (e.g. avidin-conjugated horseradish peroxidase and TMB), a photometric ELISA format reader would be able to quantitate the result.

XI. Multiplexing of Positive Controls

In certain embodiments, one or more positive control can be added to each reaction vessel. For example, a positive control in every well can be used to distinguish from the allele specific reactions by virtue of having a different fluorophore or enzyme-substrate combinations. For example, if the allele specific reaction and the positive control use different fluorophores, then the excitation and emission wavelengths for both fluorophores can be used. The positive control amplified fragment would be longer than the allele specific reaction so that the allele specific reaction would be favored. The positive controls would be captured by the same capture probe as the allele specific if the capture probe is locus-specific. If allele-specific capture probes are used, then the positive controls may have complementary sequences to the allele specific capture probes at its 5' end of the primer that is labeled.

XII. Magnetic Bead Variation

This method takes advantage of a commercially available nucleic acid purification method that employs magnetic beads coated with avidin or other materials to facilitate the "fishing" of the appropriate nucleic acid product of interest (KINGFISHER™ available from Thermo Labsystems, Inc.). For example, if biotinylated oligonucleotide PCR primers are used, then a biotinylated PCR product will be captured with the avidin on the beads. The magnetic beads are then pulled out of the reaction well, washed and all non-biotinylated materials will be washed off. The biotinylated products and primers are then separated from avidin coated beads by further treatment, such as elution with excess free biotin. Thereafter, the biotinylated products are hybridized to the capture probe of interest and separated from the biotinylated primers. Alternatively, a labeled hybridization probe is allowed to bind to the PCR product, followed by washing using the KINGFISHERTM method to remove any unbound non-specific signals. Lastly, the signals would be measured. Instead of biotinylated beads, covalently modified beads that attach to PCR oligonucleotides can also be used.

XIII. SSOP with Molecular Beacon Detection

In the methods of the present invention, molecular beacon oligonucleotides can be used to hybridize with allele-specific amplification products. Once the modular beacons are hybridized to a complementary sequence in an amplified product, the quencher group is no longer close enough to quench the fluorophore. As a consequence the fluorophore can be detected and quantitated. These molecular beacon oligonucleotides are known in the art and can be readily designed (see Materials section on design and construction of molecular beacon oligonucleotides). These oligonucleotides have the advantage of being directly assayable with a device that can measure fluorescence. In addition, this method can exhibit lower background signal than other methods as only oligonucleotides that are incorporated into an allele-specific product will give off a signal. Thus, molecular beacon detection does not require the addition of a detection reagent to observe whether an HLA genotype is present in an analyte.

XIV. In Situ Amplification Variation

In certain embodiments, the in situ amplification method is chosen to eliminate the need for DNA extraction and preparation. In contrast to the usual limitations of in situ amplification where the number of cycles has to be curtailed to prevent the floating away of amplified products from the cell, it is irrelevant whether amplified product stays in the cell or out. As a result, the same number of cycles can be used to generate the same degree of amplification as traditional PCR. If molecular beacon method is not incorporated into the protocol, then the reaction products from the wells will be transferred to another microtiter plate that has surface attached capture oligonucleotide probes that are similar to the ones described earlier with either conserved sequences which can be used in all the wells or allele specific sequences. By using an in situ amplification method it is then possible to use molecular beacons to detect the amplified products. In situ amplification can be carried out on a microscopic slide, a tissue sample, a microtiter plate, etc.

The molecular beacon method can be incorporated to eliminate even the washing step as well as the need for specially modified plates that can be quite expensive. It also allows for real time measurement of PCR product formation. When PCR products are formed and denatured during the various cycling steps, molecular beacons would hybridize to some of the complementary single strands, thereby fluorescing and allowing real time measurement. If real time measurement is not desired, then the molecular beacon probe can be added at the end of the reaction and only wells with amplified products that are complementary to the molecular beacon would light up. Because the unbound molecular beacon does not fluoresce, washing steps may not be necessary if the signal to noise ratio is high enough.

XV. Tissue Block Section Variation

The methods of the present invention can be carried out on paraffin embedded formaldehyde fixed sections of buffy coats, umbilical cord blood clots or blood clots placed onto glass slides with grids. The same sample can be placed onto one slide and different probes are used in an in situ method or many samples can be placed onto the same slide and the same probe is used for all the samples. In the latter, as many sections and slides of the samples will be cut as the number of probes plus controls. This method appears to be easier for the amplification, since there is no need to separate the different probes or reactions from one another.

EXAMPLES

Example 1

Detection of HLA Alleles with Pre-immobilized HLA Locus-specific Capture Oligonucleotides As a first step, experiments were carried out to determine what are the optimum conditions for immobilizing a capture oligonucleotide to a plate. In this experiment, Capture Oligonucleotidel (5'ACCGCACCCGCTCCGTCCC ATTGAAGAAAT; SEQ ID NO:278) was modified with an amine at the 5' end with a C6 linker and a biotin group on the 3' end. For the purpose of actual HLA genotyping, the Capture Oligonucleotide will not have a biotinylated 3' end. The oligonucleotidel was incubated on a 96 well Covalent Binding Microwell plate (Xenobind™, Xenopore, Hawthorne, N.J.) according to the manufacturer's instructions. The plate was then washed three times with phosphate-buffered-saline (PBS). ExtrAvidin® Peroxidase (SIGMA) was added and allowed to incubate on the tray. The plate was washed three times with PBS. TMB substrate (3,3',5,5'-Tetramethylbenzidine) was added to the plate, 1N HCl added and tray was read at 450 nm. The current optimum conditions for oligonucleotide binding was Capture Oligonucleotide at 100 ng/ul in PBS at pH 8.8 incubated overnight at 4° C. Alternatively, binding can occur at 37° C. for 2 hours with Capture Oligonucleotide at 100 ng/ul in PBS at pH 8.8.

Amplification of HLA alleles was carried out on DNA extracted from cord 10 blood from three donors: Sample #8, Sample #12, and Sample #18. Purification of the DNA was carried out using either the Salt extraction with ethanol precipitation method or the Qiagen QIAamp® isolation method. The amplification was carried out using oligonucleotide primers designed to hybridize to alleles in the HLA A, B, C loci for Class I and HLA DR and DQ for Class II. The sequences and location of these primers are given in Tables 1 & 2. For Examples 1, 2, and 3, the primers listed in Tables 5 and 6 were biotinylated.

All primers are adjusted to their optimum concentration of 100 ng/ul. Primer pair mixes were set up to aliquot into PCR trays. Two different 96 well trays are set up see Tables 3 & 4. The mixes are aliquoted into labeled 1.2 ml according to the volumes given in Tables 3 & 4.

A 96 well tray dotting machine was utilized to dot the PCR Trays. The polypropylene trays are labeled with their tray identification, i.e., Class I tray and dotting number. 200 trays can be dotted with each 1.1 ml Primer Mix set. The 96 well dotting machine was adjusted to a draw volume of 250 ul and a dispense volume of 5 ul. Fifty 96 well trays at a time can be dotted. Once the primers are dotted 17.0 ul of mineral oil was added to each well. The PCR tray was then covered with adhesive tape. The trays are then boxed and stored at −20° C. until use.

HLA allele sequence amplification was accomplished by adding the DNA mixture to the PCR tray and placing the tray in a thermal cycling oven. The DNA mixture contains: 40.0 ul of DNA (50–100 ng/ul), 4.0 ul Taq polymerase (5 U/ul), and 600.0 ul PCR Mix into a labeled 1.5 ml tube. For Class I HLA trays, the PCR mix contains 30 mM Ammonium Chloride, 150 mM Tris-HCl pH 8.8, 4 mM $MgCl_2$, and 166 uM dNTP. For Class II HLA trays, the PCR mix contains 100 mM KCl, 20 mM Tris HCl pH 8.8, 0.2% Triton X-100, 3.4 mM $MgCl_2$, and 166 uM dNTP.

A liquid sample dispensing machine was used to add the DNA mixture to tray PCR tray. The 250 ul dispensing syringe was employed. The machine was set to add 5.0 ul to a 96 well microtiter tray. The appropriate PCR tray was placed in the machine. The DNA mixture was vortexed and then 5.0 ul of DNA mixture was dispensed into each of the 96 wells of the PCR tray. The tray was then placed in the thermal cycling oven (BioOVen, BioTherM™ Products, MD). The PCR was carried out in the cycling oven in the following 6 stage program:

| | | |
|---|---|---|
| 1.) | 1 Cycle | 97° C. for 20 seconds |
| 2.) | 5 Cycles | 97° C. for 35 seconds, 61° C. for 45 seconds, 72° C. for 40 seconds |
| 3.) | 25 Cycles | 97° C. for 20 seconds, 59° C. for 45 seconds, 72° C. for 40 seconds |
| 4.) | 4 Cycles | 97° C. for 20 seconds, 57° C. for 45 seconds, 72° C. for 90 seconds |
| 5.) | 1 Cycle | 72° C. for 4 minutes |
| 6.) | 1 Cycle | 30° C. for 1 second |

This 6-stage program generates the optimum PCR amplification profile for this example. After amplification, PCR product was diluted. A dilution of 1:10 with PBS pH 7.4 was optimum. Therefore, 90 ul of PBS pH 7.4 was added to the PCR product. 50.0 ul of diluted PCR product was transferred from the PCR tray to the Capture plate using the 96 well dotting machine. The machine was adjusted to draw and dispense 50.0 ul.

The capture tray was then placed in the thermal cycling oven and the one stage Capture Program was run. The Capture program for this example was as follows: 1 Cycle of 97° C. for 6 minutes, 57° C. for 12 minutes, and 30° C. for 1 second. 100 ul of hybridization solution (PBS at pH 7.4) was added to the capture tray. Also a hybridization solution of 0.9 M NaCl, 90 mM sodium citrate, 1 mM EDTA, 0.1% Ficoll, 0.3% BSA, 0.5% SDS can be used. The tray was incubated at 45° C. for 120 minutes. After the hybridization incubation the capture plate was washed. Using the plate washer, the capture plate was rinsed three times with 200 ul PBS pH 7.4 in each well.

For detection, ExtrAvidin® Peroxidase was diluted 1:2000 in 4% BSA in PBS pH 7.4, and 50.0 ul was added to each well. The Capture tray was incubated at 37° C. for 30 minutes. Then the Capture tray was washed four times with 200 ul PBS pH 7.4 in each well by the plate washer. 50.0 ul of liquid substrate (3,3',5,5'-Tetramethylbenzidine) was added to each well and incubated at 37° C. for 30 minutes. 50.0 ul of 1N HCl was added to each well to stop the reaction. The trays are read on the Plate reader by setting the filter to 450 nm. The plate configuration was set to default a 96 well Flat bottom microtiter plate.

Data readings are stored as a spreadsheet file. Positive reactions are identified by values over threshold. Threshold was determined by numerical values that are at least 3.5 times over the value of the negative control and the average of the negative reaction values. HLA typing results are determined by the specificity corresponding to the positive reactions. The genotypes were determined as follows: Sample #8 A*0201,A*2402, B*0701, B*3501 C*0401, DRB1*0101,DRB1*1501 DRB5*0101: Sample #12, A*0201, B*1301, B*4402, C*0601 DRB1*0403, DRB1*1401 DRB3*0101,DRB4*0101;and Sample#18 A*0101,A*1101 B*0801,B*1801, C*0701, DRB1*0901, DRB1*1403, DRB3*0301, DRB4*0101.

Example 2

Simultaneous Hybridization of Capture Oligonucleotide to Denatured PCR Product to Capture Plate For this example, a modification of the method carried out in Example 1 was performed. In this example, the amplification product is hybridized to a capture oligonucleotide(s) in solution. The capture oligonucleotide is then immobilized on a solid phase. The complexes are washed and a detection step is then performed.

The set-up of the PCR Tray was carried out as in Example 1. The PCR amplification was carried out as in Example 1 on DNA from donors #8, #12, and #18. The DNA was purified as in Example 1. After PCR amplification, diluted capture oligonucleotide was added to the wells: 5.0 ul of capture oligonucleotide at a concentration of 50 ng/ul was added to each well. The tray was placed in a thermal cycling oven and subjected to the following capture program: 1 Cycle of 97° C. for 20 seconds, 57° C. for 60 seconds, and 30° C. for 1 second. After the capture program is run, the PCR products are now hybridized with the capture oligonucleotide. The hybridized PCR products are diluted. A dilution of 1:10 with PBS at pH 7.4 was optimum. 90.0 ul of PBS at pH 7.4 was added to each well in the PCR tray. 15.0 ul of the diluted PCR product was transferred by the 96 well dotting machine into a new covalent binding plate (Xenobind™) containing 50.0 ul of PBS at pH 7.4 in each well. The plate was incubated overnight at room temperature so that the hybridized PCR product with the capture oligonucleotide with its amine linker at the 5' end can bind to the plate.

Using the plate washer, the plate was washed twice with 0.1% BSA in PBS at pH 7.4. ExtrAvidin® Peroxidase conjugate was diluted 1:2000 in 4% BSA in PBS at pH 7.4, and 50.0 ul was added to each well. The plate was incubated at 37° C. for 30 minutes and then washed six times with 200 ul of PBS pH 7.4 in each well by the plate washer. 50.0 ul of liquid substrate (3,3',5,5'-Tetramethylbenzidine) was added to each well and incubated at 37° C. for 30 minutes. 50.0 ul of 1N HCl was added to each well to stop the reaction. The Tray reading was carried out as in Example 1. The Analysis is carried out as in Example 1.

Four basic results were observed. A "Good" result was assigned if the value for the negative control was the same as the value of a negative allele specific primer pair. Also the value of the positive control had to be higher than the value of the negative control by a factor of at least 3.5. Furthermore, the value of all positive wells had to be 3.5 times greater than the negative wells. A "Weak" result was assigned if the signal to noise ratio is above three fold but less than the 3.5 fold necessary for comfortable discrimination between positive reactions and negative reactions. Results were identified as "Too Positive" or "Background" if the value of the negative control was within acceptable limits but some of the negative wells have values equal or above that of the positive control wells. Results of "Too Positive" were observed when the Avidin conjugate concentration was too high or if insufficient washing was performed or if there was PCR DNA contamination. An "All Negative" result would be assigned if the values of the all wells were similar to the value of the negative control well. Results of "All negative" were observed when hybridization temperatures were too stringent (above 45° C.) or if the hybridization incubation times were too short (less than one hour) or if the washing conditions were too vigorous. Dilution and washing conditions are important factors to obtain the best conditions. If the hybridization product was not diluted enough, non-specific binding would result in false positives. If the washes were not exhaustive enough, false positive results would be observed.

The use of the automatic plate washer eliminated the inconsistent results and false positives that results from accidental PCR product contamination that manual handling produces. Once the washer was employed, false positive reactions and false negative reactions were greatly reduced. This observation is most likely and logically attributed to the elimination of carryover and inconsistent washing that occurs with manual washing.

In parallel with the procedure just carried out, PCR-SSP was performed using the same primer pair sets and amplification conditions. Briefly, PCR-SSP was performed with the primers sets described and the amplification products were run on agarose gels. The bands on the gel identified the positive reactions and a typing was obtained based on the positive reactions.

The allele assignments of donors #8, #12, and #18 using the PCR-SSP method and the inventive method of this example are given below:

Summary of Typing Results

Sample #8:
PCR-SSP: A*0201,A*24XX B*07XX, B*3501 C*0401 DRB1*0101 DRB1*1501 DRB5*0101.
Inventive Method: A*0201,A*2402, B*0701, B*3501, C*0401, DRB1*0101, DRB1*1501, DRB5*0101.
Sample #12:
PCR-SSP: A*0201, B*1301, B*44XX, C*0601, DRB1*0403, DRB1*1401, DRB3*0101, DRB4*01XX.
Inventive Method: A*0201, B*1301, B*4402, C*0601, DRB1*0403, DRB1*1401, DRB3*0101, DRB4*0101.
Sample #18:
PCR-SSP: A*0101,A*1101, B*0801, B*1801, C*0701, DRB1*0901, DRB1*14XX, DRB3*03XX, DRB4*01XX.
Inventive method: A*0101, A*1101, B*0801, B*1801, C*0701, DRB1*0901, DRB1*1403, DRB3*0301, DRB4*0101.

The HLA typing from the two methods matched and was found to be in total correlation. With these samples there was 100% specificity, that is, all positive controls or expected positive samples were detected as positive reactions with readings that were at least 3.5 fold that of negative values, and all expected negative controls or samples produce negative results. 100% sensitivity was also observed with the appropriate positive readings for the positive controls or expected positive samples.

The HLA nomenclature at the allelic level is as follows. The first letter denotes the locus, i.e. HLA A and B for Class I, or DRB for Class II. The asterisk (*) denotes DNA typing. The first two numbers designates serological level or equivalent assignments. The third and fourth numbers are the allele level subtypes that are distinguished by DNA typings. The fifth and sixth numbers are usually not displayed because these designate silent mutations, i.e. DNA substitutions that do not produce changes in protein sequence coding of the final HLA protein antigen. The seventh number, which is usually not displayed as well, denotes a null mutation, which is a mutation that silences the expression of the allele at the protein or MRNA level. There are one to two potential alleles at each locus; however, in homozygous situations where both alleles are identical, only one allele can be identified and typed. Where there is an XX after the first two numbers, it means that only one allele can be identified. This usually means that there may be homozygosity, but in a small number of cases, there may mean that there is a allele that was not detected by the entire panel of primers either because the panel cannot be all inclusive or because the allele is new and previously undiscovered.

In all instances, positive reactions observed on the PCR-SSP agarose gels corresponded to positive OD values that are at least 3.5-fold that of negative controls or negative wells on the plate reader. In this respect, it is instructive to note that because the inventive method of this example is amenable to larger sets of primer pairs, it detects several of the alleles at a higher level of resolution than the PCR-SSP method. Hence, there were several XX assignments for the third and fourth numbers in some of the alleles tested by PCR-SSP. However, the PCR-SSP method is fully capable of typing every sample to the same degree of resolution as the inventive method of this example even though is far more laborious.

Example 3

Amplification of HLA Sequences with an Immobilized Allele-specific Primer

This method involves the amplification of HLA sequences using allele-specific primers, where one of the pair of amplification primers is immobilized to a solid phase. The other primer constituting a primer pair contains a detectable label and is initially free in solution. Reference DNAs were used as the template nucleic acid. The reference DNAs are from a panel of DNA that was used for the UCLA DNA Exchange Program. Primers directed to detecting class II HLA alleles were used in this example. In this example, the following immobilization primers contained an amine group followed by a C6 linker: SEQ ID NO: 189, DR06, CGTTTCTTGGAGCAGGCTAAGTG; SEQ ID NO: 190, DR07, CGTTTCTTGGAGTACTCTACGGG; SEQ ID NO: 191, DR08, ACGTTTCTTGGAGCAGGTTAAAC; SEQ ID NO: 192, DR09, CGTTTCCTGTGGCAGCCTAAGA; SEQ ID NO: 193, DR10, CGTTTCTTGGAGTACTCTACGTC; and SEQ ID NO: 277, DRCPT1, TGGCGTGGGCGAGGCAGGGTAACTTCTTTA. The primers were immobilized to a XenobindTm (Covalent Binding Microwell Plates), Xenopore, Hawthorne, N.J.) plate according to the manufacturer's instructions. The DNA samples were isolated from reference samples known HLA allele sequences. The amplification buffer and components are the same as in Example 1 for the class II amplification. The buffer containing Taq and the proper amplification reagents were added to the microtiter wells. The other member of the primer pairs were biotinylated at their 5' ends and were as follows: SEQ ID NO:222, DR39, TGCACTGTGAAGCTCTCAC, SEQ ID NO:223, DR40, CTGCACTGTGAAGCTCTCCA. The primers were paired in separate microtiter wells as follows for sample 219 and sample 223:

| Mix | Primer 1 | Primer 2 | Specificity |
|---|---|---|---|
| 1 | DR09 | DR39 | DR16 |
| 2 | DR09 | DR40 | DR15 |
| 3 | DR10 | DR39 | DR 3A, 11A, 13A, 14A |
| 4 | DR10 | DR40 | DR 3B, 11B, 13B, 14B |
| 5 | DR08 | DR39 | DR 4A |
| 6 | DR08 | DR40 | DR 4B |
| 7 | DR07 | DR39 | DR 8 |
| 8 | DR07 | DR40 | DR12 |
| 9 | DR06 | DR39 | DR53 |
| 10 | Drcapt1 | DR39, 40 | positive control |
| 11 | none | none | none |
| 12 | none | none | none |

The amplification program was carried out as in Example 1. After amplification, the plate was washed twice with 0.1% BSA in PBS at pH 7.4. ExtrAvidin® Peroxidase conjugate was diluted 1:2000 in 4% BSA in PBS at pH 7.4. 50.0 ul was added to each well. The plate is incubated at 37° C. for 30 minutes and then washed six times with 200 ul of PBS pH 7.4 in each well by the plate washer. 50.0 ul of liquid substrate (3,3',5,5'-Tetramethylbenzidine) is added to each well and incubated at 37° C. for 30 minutes. 50.0 ul of 1N HCl is added to each well to stop the reaction. In parallel with the immobilized PCR method just described, PCR-SSP using the above listed primers pairs was carried out and the samples were typed by running them on agarose gels. The results of the PCR-SSP typing method and the immobilized PCR primer method carried out in this example were in complete agreement. The expected typing of the reference DNA and the genotypes determined using PCR-SSP and immobilized PCR of this example were the same:

| DNA ID | HLA Genotype of the Reference DNA | Genotype determined by PCR-SSP and the Inventive Method |
|---|---|---|
| 219 | DR1501, DR0404 | DR15, DR04B |
| 223 | DR1101, DR0403 | DR3, 11, 13, 14A, DR04B |

Thus, this example shows that PCR can be carried out with an immobilized primer to successfully genotype samples for their HLA allele sequences.

Example 4

Multiplexing of Positive Controls into Every Well

A positive control in every well can be used to distinguish from the allele specific reactions by virtue of having a different fluorophore or enzyme-substrate. For example, if the allele specific reaction and the positive control use different fluorophores, then the excitation and emission wavelengths for both fluorophores will be used. The positive control amplified fragment will be longer than the allele specific reaction so that the allele specific reaction would be favored. The positive controls would be captured by the same capture probe as the allele specific if the capture probe is conserved. If the allele specific capture probes are used, then the positive controls may have complementary sequences to the allele specific capture probes at its 5' end of the primer that is labeled.

In this method, positive control primers would be used. For example, SEQ ID NO:270: 5' DPA-E (PC), 5'GATC-CCCCTGAGGTGACCGTG and SEQ ID NO:271: 3'DPA-F (PC), 5'CTGGGCCCGGGGGTCATGGCC are used. SEQ ID NO: 270 would be labeled with the amine linker at the 5' end and is designated 5'PC. SEQ ID NO: 271 is the 3' positive control primer and would be labeled with a fluorophore (e.g., fluorescein at the 5' end) and is designated 3'PC-(CTGGGCCCGGGGGTCATGGCC). These primers can be added to PCR mixes and used as internal controls in each well by detected their specific fluorescent signal.

Example 5

Detection of HLA Sequences Using Molecular Beacon Probes

Molecular beacon probes could be used to detect allele-specific amplification products. Briefly, amplification of HLA allele sequences using HLA-specific primers is first carried out. Then molecular beacon probes that hybridize with HLA alleles sequences are hybridized to denatured amplification products. If the molecular beacon probe hybridizes then the fluorophore is no longer quenched and fluorescence would be exhibited and detected.

Fluorophore—quencher probes would be constructed from the HLA sequences given in Table 1 and 2. The loop portion of the probe would be constructed so that the sequence matched the polymorphic sequences of the HLA sequences similar to the sequences given in Tables 1 & 2. At the 5' termini there a would be 5 nucleotides of T ending with the fluorophore (e.g. 5-(2'-aminoethyl) aminonapthtalene-1-sulfonic acid (EDANS) at the 5' end. At the 3' end there would be a poly-A tail of 5 nucleotides ending with the quencher (e.g. 4-(4'-dimethylaminophenylazo)-benzoic acid (DABCYL) at the 3' end.

Following PCR amplification, the products are denatured by incubating them at 100° C. for 10 minutes and then diluted in hybridization buffer. Diluted Class I products are added to the Molecular Beacon tray containing the Class I fluorophore and quencher probes. Similarly, the Class II diluted PCR product is added to the Class II Molecular Beacon tray.

To make up the tray containing the molecular beacon primers, 0.5–1.0 uM concentration of molecular beacon primers are made. The molecular beam primers would be added to wells containing allele-specific amplification products. The Molecular Beacon tray is allowed to incubate at 45–57° C. for a period of time to allow for hybridization.

When the complementary target is encountered the fluorophore is exposed and the probe can fluoresce. The tray is read by a fluorescent reader with the excitation set at 336 nm and the emission set at 490 nm. Positive reactions are identified by strong fluorescent reading and data readings are stored as a spreadsheet file. Positive reactions are identified by values over threshold. Threshold is determined by numerical values that are at least 3 times over the value of the negative control and the average of the negative reaction values.

Example 6

In Situ Amplification Variation

Oligonucleotide primers will be used that are designed to hybridized to the polymorphic regions of HLA A, B, C loci for Class I and HLA DR and DQ for Class II. The sequences and location of these primers are given in Tables 1 & 2. The primers listed in Tables 5 and 6 are biotinylated. All primers are adjusted to their optimum concentration of 100 ng/ul. Primer pair mixes will be set up to aliquot into PCR trays. Two different 96 well trays will be set up see Tables 3 & 4. The mixes will be aliquoted into labeled 1.2 ml tubes according to the volumes given in Tables 3 & 4. A 96 well tray dotting machine is utilized to dot the PCR Trays. The polypropylene trays are labeled with their tray identification, i.e., Class I tray and dotting number. 200 trays can be dotted with each 1.1 ml Primer Mix set. The 96 well dotting machine is adjusted to a draw volume of 250 ul and a dispense volume of 5.0 ul. Fifty 96 well trays at a time can be dotted. Once the primers are dotted 17.0 ul of mineral oil is added to each well. The PCR tray is then covered with adhesive tape. The trays are then boxed and stored at −20° C. until use.

The sample would be a cell prep containing nucleated cells, or a crude cell prep with inhibitory proteins (heme) removed. First, 50–100 mg of cell prep are diluted in 100–200 ul of dH2O. Then Proteinase K (20 mg/ml) (Fisher Scientific) would be added (100 ul is used for every 50 mg of cell prep) and the sample is incubated to digest proteins in the sample. The lysate sample is incubated at 100° C. for 1 minute to inactivate the Proteinase K.

PCR amplification would be accomplished by adding the DNA mixture to the PCR tray and placing the tray in a thermal cycling oven. For DNA mixture aliquot-lysate sample, 4.0 ul Taq polymerase (5 U/ul), and 600.0 ul PCR Mix into a labeled 1.5 ml tube and place on ice. The PCR buffers are the sample as in Example 1: For Class I trays, PCR Mix–30 mM Ammonium Chloride, 150 mM TRIS-HCl pH 8.8, 4 mM $MgCl_2$, and 166 uM dNTP; For Class II trays, PCR Mix–100 mM KCl, 20 mM TRIS HCl pH 8.8, 0.2% Triton X-100, 3.4 mM $MgCl_2$, and 166 uM dNTP.

A Liquid Sample Dispensing machine would be used to add the DNA mixture to tray PCR tray. The 250 ul dispensing syringe would be employed. The machine would be set to add 5.0 ul to a 96 well microtiter tray. The appropriate PCR tray would be placed in the machine. The DNA mixture would be vortexed and then 5.0 ul of DNA mixture would be dispensed into each of the 96 wells of the PCR tray. The tray would then be placed in the thermal cycling oven.

After PCR amplification, diluted capture oligonucleotide would be added to the wells. 5.0 ul of capture oligonucleotide at a concentration of 50 ng/ul would be added to each well. The tray would be placed in the thermal cycling oven and a capture thermal cycle program run. After the capture thermal cycling, the PCR products are now hybridized with the capture oligonucleotide. The hybridized PCR products are diluted. A dilution of 1:10 with PBS at pH 7.4 is optimum. 90.0 ul of PBS at pH 7.4 is added to each well in the PCR tray. 15.0 ul of the diluted PCR product is transferred by the 96 well dotting machine into a new covalent binding plate containing 50.0 ul of PBS at pH 7.4 in each well. The plate would be incubated overnight at room temperature so that the hybridized PCR product with the capture oligonucleotide with its amine linker at the 5' end can bind to the plate. The unbound products are removed by washing. Using the plate washer, the plate is washed twice with 0.1% Tween 20 in PBS at pH 7.4. Avidin peroxidase conjugate is diluted 1:2000 in 4% BSA in PBS at pH 7.4. 50.0 ul is added to each well. The plate is incubated at 37° C. for 30 minutes.

The plate is washed six times with 200 ul of PBS pH 7.4 in each well by the plate washer. 50.0 ul of liquid substrate (3,3',5,5'-Tetramethylbenzidine) is added to each well and incubated at 37° C. for 30 minutes. 50.0 ul of 1N HCl is added to each well to stop the reaction. Trays are read on a microtiter plate reader by setting the filter to 450 nm. The data readings would be stored as a spreadsheet file and analyzed. Positive reactions are identified by values over threshold. Threshold is determined by numerical values that are at least 3.5 times over the value of the negative control and the average of the negative reaction values.

Example 7

In Situ Amplification—Molecular Beacon Variation

HLA-specific Molecular beacon probes would be constructed as in Example 5. A tray of molecular beacon probes would be spotted into microtiter plates. The template nucleic acid is contained in a cell prep containing nucleated cells or a crude cell prep with inhibitory proteins (heme) removed. First, 50–100 mg of cell prep are diluted in 100–200 ul of dH2O. Then Proteinase K (20 mg/ml ) (Fisher Scientific) would be added (100 ul is used for every 50 mg of cell prep) and the sample is incubated to digest proteins in the sample. The lysate sample is incubated at 100° C. for 1 minute to inactivate the Proteinase K.

PCR amplification would be accomplished by adding the DNA mixture to the PCR tray and placing the tray in a thermal cycling oven. HLA locus-specific primers are utilized to amplify HLA Class I and Class II products. For Class I primers are selected to amplify Class I exon 2 and exon 3 products. For Class II, primers are selected to amplify Class II exon 2 products. For DNA mixture aliquot—lysate sample, 4.0 ul Taq polymerase (5 U/ul), and 600.0 ul PCR Mix into a labeled 1.5 ml tube and place on ice. The PCR buffers are the sample as in Example 1. Following PCR amplification, the PCR product is denatured by incubation at 100° C. for 10 minutes and then diluted in hybridization buffer.

Diluted Class I products would be added to the Molecular Beacon tray containing the Class I fluorophore and quencher probes. Similarly, the Class II diluted PCR product would be added to the Class II Molecular Beacon tray. The Molecular Beacon tray is allowed to incubate at 45–57° C. for a period of time to allow for hybridization. When the complementary target is encountered the fluorophore is exposed and the probe can fluoresce. The tray is read by a fluorescent reader with the excitation set at 336 nm and the emission set at 490 nm. Positive reactions are identified by strong fluorescent reading and data readings are stored as a spreadsheet file. Positive reactions are identified by values over threshold. Threshold is determined by numerical values that are at least 3.5 times over the value of the negative control and the average of the negative reaction values.

Example 8

Tissue Block Section Variation

The tissue block section method is a variation of the molecular beacon method with the use of a paraffin embedded tissue sample. The construction of the fluorophore-quencher probe is carried out as in Example 8 (Construction of the fluorophore-quencher probe). Molecular beacon tray set up would be carried out as in Example 8.

The amplification of sequences on a paraffin block sample would occur on a glass slide which will necessitate dotting the PCR mixes on a glass slide. Samples embedded in paraffin are sectioned and each slide would be added to a glass slide. The specific primer mix and DNA mixture would be added to an individual glass slide. HLA locus primers are utilized to amplify HLA Class I and Class II products. For Class I primers are selected to amplify Class I exon 2 and exon 3 products. For Class II, primers are selected to amplify Class II exon 2 products. There will be 96 individual slide made to complete the Class I or Class II sets. After adding the mix, the glass slide would be sealed with a cover slip. The slides are placed in the thermal cycling oven and the PCR program for slides would be run. 1 cycle of 96° C. for 30 seconds followed by 34 cycles of 96° C. for 30 seconds, 61° C. for 60 seconds, 72° C. for 60 seconds.

Following PCR amplification, the PCR product would be denatured by incubation at 100° C. for 10 minutes and then diluted in hybridization buffer (0.9 M NaCl, 90 mM sodium citrate, 1 mM EDTA, 0.1% Ficoll, 0.3% BSA, and 0.5% SDS). Diluted Class I products are added to the Molecular Beacon tray containing the Class I fluorophore and quencher probes. Similarly, the Class II diluted PCR product would be added to the Class II Molecular Beacon tray. The Molecular Beacon tray would be allowed to incubate at 45–57° C. for 1 hour to allow for hybridization.

When the complementary target is encountered the fluorophore is exposed and the probe can fluoresce. The tray would be read by a fluorescent reader with the excitation set at 336 nm and the emission set at 490 nm. Positive reactions are identified by a strong fluorescent reading; positive reactions are identified by values over threshold. Threshold is determined by numerical values that are at least 3 times over the value of the negative control and the average of the negative reaction values. The data readings are then stored as a spreadsheet file. In this manner, HLA genotyping could be achieved.

All publications, patents and patent applications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

TABLE 1

| Primer (SEQ ID NO:) | | SEQUENCE (5'–3') 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | MER |
|---|---|---|---|---|---|---|---|---|---|---|---|---|---|---|---|---|---|---|---|---|---|---|---|---|---|---|---|---|---|---|---|---|
| CI01(1) | 5' HLA-C ex2 221–239 | C | C | G | A | G | T | G | A | A | C | C | T | G | C | G | G | A | A | A | | | | | | | | | | | | 19 |
| CI02(2) | 6' HLA-C Ex2 249–268 | T | A | C | T | A | C | A | A | C | C | A | G | A | G | C | G | A | G | G | A | | | | | | | | | | | 20 |
| CI03(3) | 5' HLA B&C Ex2 210–228 | C | A | C | A | G | A | C | T | G | A | C | C | G | A | G | T | G | A | G | | | | | | | | | | | 19 | |
| CI04(4) | 5' HLA-C Ex2 123–140 | A | G | T | C | C | A | A | G | A | G | G | G | G | A | G | C | C | G | | | | | | | | | | | 18 | | |
| CI05(5) | 5' HLA-A&C Ex2 5–25 | C | C | A | C | T | C | C | A | T | G | A | G | G | T | A | T | T | T | C | T | | | | | | | | | | | 20 |
| CI06(6) | 3' HLA-C Ex3 243–263 | T | C | T | T | C | T | C | C | A | G | A | A | G | G | C | A | C | C | A | T | | | | | | | | | | | 20 |
| CI07(7) | 3' HLA-C Ex3 243–263 | C | A | G | G | T | C | A | G | T | G | T | G | A | T | C | T | C | C | A | | | | | | | | | | 19 | | |
| CI08(8) | 3' HLA-B&C Ex3 195–213 | C | C | T | C | C | A | G | G | T | A | G | G | C | T | C | T | C | C | A | | | | | | | | | | | 19 | |
| CI09(9) | 3' HLA-C Ex4 234–251 | C | A | G | C | C | C | C | T | C | G | T | G | C | T | G | C | A | T | | | | | | | | | | | | | 18 |
| CI10(10) | 3' HLA-C Ex3 258–275 | C | G | C | G | C | G | C | T | G | C | A | G | C | G | T | C | T | T | | | | | | | | | | | | | 18 |
| CI11(11) | 3' HLA-C Ex3 195–213 | C | C | T | C | C | A | G | G | T | A | G | G | C | T | C | T | C | A | G | | | | | | | | | | | | 19 |
| CI12(12) | 3' HLA-C Ex4 31–49 | C | T | C | A | G | G | G | T | G | A | G | G | G | G | C | T | C | T | | | | | | | | | | | | | 18 |
| CI13(13) | 3' HLA-C Ex3 134–151 | T | G | A | G | C | C | G | C | C | G | T | G | T | C | C | G | C | A | | | | | | | | | | | | | 18 |
| CI14(14) | 3' HLA-B & C Ex3 18–36 | G | G | T | C | G | C | A | G | C | C | A | T | A | C | A | T | C | C | A | | | | | | | | | | | | 19 |
| CI15(15) | 5' HLA-B & C Ex3 59–76 | C | C | G | C | G | G | G | T | A | T | G | A | C | C | A | G | T | C | | | | | | | | | | | | | 18 |
| CI16(16) | 3' HLA-C Ex4 4–23 | G | C | G | T | C | T | C | C | T | T | C | C | C | G | T | T | C | T | T | | | | | | | | | | | | 19 |
| CI17(17) | 3' HLA-C Ex4 4–23 | A | G | C | G | T | C | T | C | C | T | T | C | C | C | A | T | T | C | T | T | | | | | | | | | | | 20 |
| CI18(18) | 5' HLA-C Ex3 134–151 | T | C | C | G | C | G | G | G | T | A | T | G | A | C | C | A | G | T | A | | | | | | | | | | | | 19 |
| CI19(19) | 3' HLA-C Ex3 25–42 | G | C | C | C | C | A | G | G | T | C | G | C | A | G | C | C | A | A | | | | | | | | | | | | | 18 |
| CI20(20) | 5' HLA-C Ex2 195–213 | A | C | A | A | G | C | G | C | C | A | G | G | C | A | C | A | G | G | | | | | | | | | | | | | 18 |
| CI21(21) | 3' HLA-ABC Ex3 216–233 | G | A | G | C | C | A | C | T | C | C | A | C | G | C | A | C | T | C | | | | | | | | | | | | | 18 |
| CI22(22) | 3' HLA-A & C Ex3 196–214 | C | C | C | T | C | C | A | G | G | T | A | G | G | C | T | C | T | C | T | | | | | | | | | | | | 19 |
| CI23(23) | 3' HLA-B & C Ex3 65–84 | T | C | G | T | A | G | G | C | T | A | A | C | T | G | G | T | C | A | T | G | | | | | | | | | | | 20 |
| CI24(24) | 3' HLA-C Ex3 131–148 | C | C | G | C | C | G | T | G | T | C | C | G | C | G | G | C | A | | | | | | | | | | | | | | 17 |
| CI25(25) | 5' HLA-C Ex2 252–270 | T | A | C | A | A | C | C | A | G | A | G | C | G | A | G | G | C | C | A | | | | | | | | | | | | 19 |
| CI26(26) | 5' HLA-C Ex2 253–270 | A | C | A | A | C | C | A | G | A | G | C | G | A | G | G | C | C | G | | | | | | | | | | | | | 18 |
| CI27(27) | 5' HLA-C Ex2 85–103 | A | C | G | A | C | A | C | G | C | A | G | T | T | C | G | T | G | C | A | | | | | | | | | | | | 19 |
| CI28(28) | 3' HLA-C Ex2 229–246 | G | C | G | C | A | G | G | T | T | C | C | G | C | A | G | G | C | | | | | | | | | | | | | | 17 |
| CI29(29) | 3' HLA-A Ex3 216–233 | G | A | G | C | C | A | C | T | C | C | A | C | G | C | A | C | C | G | | | | | | | | | | | | 18 | |
| CI32(30) | 3' HLA-ABC Ex3 216–233 | G | A | G | C | C | A | C | T | C | C | A | C | G | C | A | C | G | T | | | | | | | | | | | | | 18 |
| CI31(31) | 3' HLA-A Ex3 195–213 | C | C | T | C | C | A | G | G | T | A | G | G | C | T | C | T | C | T | G | | | | | | | | | | | | 19 |
| CI32(32) | 3' HLA-A Ex3 48–64 | C | C | G | C | G | G | A | G | G | A | A | G | C | G | C | C | A | | | | | | | | | | | | | | 17 |
| CI33(33) | 5' HLA-A Ex2 5–25 | C | C | A | C | T | C | C | A | T | G | A | G | G | T | A | T | T | T | C | T | T | | | | | | | | | | 21 |
| CI34(34) | 5' HLA-A Ex2 168–186 | C | C | G | G | A | G | T | A | T | T | G | G | G | A | C | C | T | G | C | | | | | | | | | | | 19 | |
| CI35(35) | 3' HLA-C Ex3 25–41 | C | C | C | C | A | G | G | T | C | G | C | A | G | C | C | A | G | | | | | | | | | | | | | | 17 |
| CI36(36) | 3' HLA-B & C Ex3 169–185 | C | G | C | A | C | G | G | G | C | C | G | C | C | T | C | C | A | | | | | | | | | | | | | | 17 |
| CI37(37) | 5' HLA-B Ex2 144–161 | G | C | G | C | C | G | T | G | G | A | T | A | G | A | G | C | A | A | | | | | | | | | | | | | 18 |
| CI36(38) | 5' HLA-B Ex2 117–133 | G | C | C | G | C | G | A | G | T | C | C | G | A | G | G | A | C | | | | | | | | | | | | | | 17 |
| CI39(39) | 5' HLA-B Ex2 181–199 | A | C | C | G | G | A | A | C | A | C | A | C | A | G | A | T | C | T | G | | | | | | | | | | | | 19 |
| CI40(40) | 5' HLA-B Ex2 181–199 | A | C | C | G | G | G | A | G | A | C | A | C | A | G | A | T | C | T | C | | | | | | | | | | | | 19 |
| CI41(41) | 5' HLA-A & B Ex2 170–188 | G | G | A | G | T | A | T | T | G | G | G | A | C | C | G | G | A | A | C | | | | | | | | | | | | 19 |
| CI42(42) | 5' HLA-B Ex2 195–212 | A | A | C | A | T | G | A | A | G | G | C | C | T | C | C | G | C | G | | | | | | | | | | | | | 18 |
| CI43(43) | 5' HLA-B Ex2 180–199 | G | A | C | C | G | G | A | A | C | A | C | A | C | A | G | A | T | C | T | T | | | | | | | | | | | 20 |
| CI44(44) | 3' HLA-B Ex2 219–236 | T | A | C | C | G | A | G | A | G | A | A | C | C | T | G | C | G | C | | | | | | | | | | | | | 18 |
| CI45(45) | 5' HLA-B Ex2 157–173 | A | G | C | A | G | G | A | G | G | G | G | C | C | G | G | A | A | | | | | | | | | | | | | | 17 |

TABLE 1-continued

| Primer (SEQ ID NO:) | | SEQUENCE (5'–3') 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | MER |
|---|---|---|---|---|---|---|---|---|---|---|---|---|---|---|---|---|---|---|---|---|---|---|---|---|---|---|---|---|---|---|---|---|
| CI46(46) | 5' HLA-B Ex2 51–68 | G | G | G | G | A | G | C | C | C | C | G | C | T | T | C | A | T | T | | | | | | | | | | | | | 18 |
| CI47(47) | 5' HLA-B Ex2 192–210 | C | A | G | A | T | C | T | A | C | A | A | G | G | C | C | C | A | G | G | | | | | | | | | | | | 19 |
| CI48(48) | 5' HLA-B Ex2 5–30 | C | C | A | T | G | A | G | G | T | A | T | T | T | C | T | A | C | A | C | C | G | | | | | | | | | | 21 |
| CI49(49) | 5' HLA-B Ex2 180–199 | G | A | C | C | G | G | A | A | C | A | C | A | C | A | G | A | T | C | T | A | | | | | | | | | | | 20 |
| CI50(50) | 5' HLA-B & C Ex2 221–238 | C | C | G | A | G | A | G | A | G | C | C | T | G | C | G | G | A | A | | | | | | | | | | | | | 18 |
| CI51(51) | 5' HLA-A & B Ex2 220–238 | A | C | C | G | A | G | A | G | A | A | C | C | T | G | C | G | G | A | T | | | | | | | | | | | | 19 |
| CI52(52) | 5' HLA-B Ex2 116–133 | C | G | C | C | G | C | G | A | G | T | C | C | G | A | G | A | G | A | | | | | | | | | | | | | 18 |
| CI53(161) | 5' Control Primer PIC1 | A | T | G | A | T | G | T | T | G | A | C | C | T | T | T | C | C | A | G | G | G | | | | | | | | | | 21 |
| CI54(162) | 3' Control Primer PICA | T | T | C | T | G | T | A | A | C | T | T | T | T | C | A | T | C | A | G | T | T | G | C | | | | | | | | 23 |
| CI55(55) | 3' HLA-B Ex3 195–213 | C | C | T | C | C | A | G | G | T | A | G | G | C | T | C | T | G | T | C | | | | | | | | | | | | 19 |
| CI56(56) | 3' HLA-B & C Ex3 44–59 | G | A | G | G | A | G | G | C | G | C | C | C | G | T | C | G | | | | | | | | | | | | | | | 16 |
| CI57(57) | 3' HLA-ABC Ex3 76–92 | C | T | T | G | C | C | G | T | C | G | T | A | G | G | C | G | G | | | | | | | | | | | | | | 17 |
| CI58(58) | 3' HLA-B & C Ex3 77–95 | A | T | C | C | T | T | G | C | C | G | T | C | G | T | A | G | G | C | T | | | | | | | | | | | | 19 |
| CI59(59) | 3' HLA-B Ex3 92–111 | C | G | T | T | C | A | G | G | G | C | G | A | T | G | T | A | A | T | C | T | | | | | | | | | | | 20 |
| CI60(60) | 3' HLA-B Ex3 201–218 | C | G | T | G | C | C | C | T | C | C | A | G | G | T | A | G | G | T | | | | | | | | | | | | | 18 |
| CI61(61) | 3' HLA-ABC Ex3 216–233 | G | A | G | C | C | A | C | T | C | C | A | C | G | C | A | C | T | C | | | | | | | | | | | | | 18 |
| CI62(62) | 3' HLA-B Ex3 229–246 | C | C | A | G | G | T | A | T | C | T | G | C | G | G | A | G | C | G | | | | | | | | | | | | | 18 |
| CI63(63) | 3' HLA-B Ex3 260–276 | C | C | G | C | G | C | G | C | T | C | C | A | G | C | G | T | G | | | | | | | | | | | | | | 17 |
| CI64(64) | 3' HLA-B Ex3 262–279 | T | A | C | C | A | G | C | G | C | G | C | T | C | C | A | G | C | T | | | | | | | | | | | | | 18 |
| CI65(65) | 3' HLA-B & C Ex 3 10–29 | G | C | C | A | T | A | C | A | T | C | C | T | C | T | G | G | A | T | G | A | | | | | | | | | | | 20 |
| CI66(66) | 3' HLA-B Ex3 18–36 | C | G | T | C | G | C | A | G | C | C | A | T | A | C | A | T | C | A | C | | | | | | | | | | | | 19 |
| CI67(67) | 3' HLA-B Ex3 184–201 | C | T | C | T | C | A | G | C | T | G | C | T | C | C | G | C | C | T | | | | | | | | | | | | | 18 |
| CI68(68) | 3' HLA-B & C Ex3 69–87 | G | T | C | G | T | A | G | G | C | G | G | A | C | T | G | G | T | C | | | | | | | | | | | | | 18 |
| CI69(69) | 3' HLA-A & B Ex3 68–85 | T | C | G | T | A | G | G | C | G | T | C | C | T | G | G | T | G | G | | | | | | | | | | | | | 18 |
| CI70(70) | 3' HLA-B Ex3 156–173 | C | T | C | C | A | A | C | T | T | G | C | G | C | T | G | G | G | A | | | | | | | | | | | | | 18 |
| CI71(71) | 3' HLA-B Ex2 173–192 | G | T | G | T | G | T | T | C | C | G | G | T | C | C | C | A | A | T | A | T | | | | | | | | | | | 20 |
| CI72(72) | 3' HLA-A & B Ex2 246–264 | C | G | C | T | C | T | G | G | T | T | G | T | A | G | T | A | G | C | G | | | | | | | | | | | | 19 |
| CI73(73) | 3' HLA-B Ex4 168–187 | G | C | C | C | A | C | T | T | C | T | G | G | A | A | G | G | T | T | C | T | | | | | | | | | | | 20 |
| CI74(74) | 3' HLA-B Ex3 11–28 | C | C | A | T | A | C | A | T | C | G | T | C | T | G | C | C | A | A | | | | | | | | | | | | | 18 |
| CI75(75) | 3' HLA-B Ex2 229–245 | G | C | G | C | A | G | G | T | T | C | C | G | C | A | G | G | C | | | | | | | | | | | | | | 17 |
| CI76(76) | 3' HLA-ABC Ex3 216–233 | G | A | G | C | C | A | C | T | C | C | A | C | G | C | A | C | A | G | | | | | | | | | | | | | 18 |
| CI77(77) | 5' HLA-A Ex3 63–80 | G | G | G | T | A | C | C | A | G | C | A | G | G | A | C | G | C | T | | | | | | | | | | | | | 18 |
| CI78(78) | 5' HLA-B & C Ex2 187–205 | G | A | G | A | C | A | C | A | G | A | A | G | T | A | C | A | A | G | C | G | | | | | | | | | | | 20 |
| CI79(79) | 3' HLA-B Ex3 120–136 | G | C | C | G | C | G | G | T | C | C | A | G | G | A | G | C | T | | | | | | | | | | | | | | 17 |
| CI80(80) | 5' HLA-B Ex2 222–239 | C | G | A | G | A | G | A | G | C | C | T | G | C | G | G | A | A | C | | | | | | | | | | | | | 18 |
| CI81(81) | 5' HLA-B Ex2 119–136 | C | G | C | G | A | G | T | C | C | G | A | G | G | A | T | G | G | C | | | | | | | | | | | | | 18 |
| CI82(82) | 3' HLA-A & B Ex3 228–245 | C | A | G | G | T | A | T | C | T | G | C | G | G | A | G | C | C | C | | | | | | | | | | | | | 18 |
| CI83(83) | 5' HLA-B Ex2 5–24 | C | C | A | C | T | C | C | A | T | G | A | G | G | T | A | T | T | T | C | C | | | | | | | | | | | 20 |
| CI84(84) | 3' HLA-B Ex3 120–136 | G | C | G | G | C | G | G | T | C | C | A | G | G | A | G | C | G | | | | | | | | | | | | | | 17 |
| CI85(85) | 3' HLA-A & B Ex3 195–213 | C | C | T | C | C | A | G | G | T | A | G | G | C | T | C | T | C | A | A | | | | | | | | | | | | 19 |
| CI86(86) | 3' HLA-B Ex2 226–243 | G | C | A | G | G | T | T | C | C | G | C | A | G | G | C | T | C | T | | | | | | | | | | | | | 18 |
| CI87(87) | 5' HLA-B Ex2 244–227 | G | G | A | C | C | T | G | C | G | G | A | C | C | C | T | G | C | T | | | | | | | | | | | | | 18 |
| CI88(88) | 5' HLA-B & C Ex2 52–69 | G | G | G | A | G | C | C | C | C | G | C | T | T | C | A | T | C | T | | | | | | | | | | | | | 18 |
| CI89(89) | 5' HLA-B Ex2 116–133 | C | G | C | C | A | C | G | A | G | T | C | C | G | A | G | G | A | A | | | | | | | | | | | | | 18 |
| CI90(90) | 3' HLA-ABC Ex3 156–172 | T | C | C | C | A | C | T | T | G | C | G | C | T | G | G | G | T | | | | | | | | | | | | | | 17 |
| CI91(91) | 3' HLA-B Ex3 44–60 | G | G | A | G | G | A | A | G | C | G | C | C | C | G | T | C | G | | | | | | | | | | | | | | 17 |

TABLE 1-continued

| Primer (SEQ ID NO:) | | SEQUENCE (5'–3') | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | MER |
| CI92(92) | 5' HLA-B Ex2 227–244 | G | A | G | C | C | T | G | C | G | G | A | C | C | C | T | G | C | T | | | | | | | | | | | | | 18 |
| CI93(93) | 5' HLA-B Ex2 222–239 | C | G | A | G | T | G | G | G | C | C | T | G | C | G | G | A | A | C | | | | | | | | | | | | | 18 |
| CI94(94) | 5' HLA-B Ex2 76–94 | G | C | T | A | C | G | T | G | G | A | C | G | A | C | A | C | G | C | T | | | | | | | | | | | | 19 |
| CI95(95) | 3' HLA-B Ex2 207–225 | C | T | C | G | G | T | C | A | G | T | C | T | G | T | G | C | C | T | T | | | | | | | | | | | | 19 |
| CI96(96) | 3' HLA-B Ex2 207–226 | T | C | T | C | G | G | T | A | A | G | T | C | T | G | T | G | C | C | T | T | | | | | | | | | | | 20 |
| CI97(97) | 5' HLA-A Ex2 174–192 | T | A | T | T | G | G | G | A | C | G | A | G | G | A | G | A | C | A | G | | | | | | | | | | | | 19 |
| CI98(98) | 3' HLA-B & C Ex3 69–87 | C | G | T | C | G | T | A | G | G | C | G | T | A | C | T | G | G | T | C | | | | | | | | | | | | 19 |
| CI99(99) | 5' HLA-A Ex2 113–130 | C | G | A | C | G | C | C | G | C | G | A | G | C | C | A | G | A | A | | | | | | | | | | | | | 18 |
| CI100(100) | 3' HLA-ABC Ex3 216–233 | G | A | G | C | C | C | G | T | C | C | A | C | G | C | A | C | T | C | | | | | | | | | | | | | 18 |
| CI101(101) | 5' HLA-A Ex2 210–229 | T | C | A | C | A | G | A | C | T | G | A | C | C | G | A | G | C | G | A | A | | | | | | | | | | | 20 |
| CI102(102) | 5' HLA-A Ex2 191–209 | A | C | G | G | A | A | T | G | T | G | A | A | G | G | C | C | C | A | G | | | | | | | | | | | | 19 |
| CI103(103) | 5' HLA-A Ex2 111–127 | A | G | C | G | A | C | G | C | C | G | C | G | A | G | C | C | A | | | | | | | | | | | | | | 17 |
| CI104(104) | 5' HLA-A Ex2 166–184 | G | G | C | C | G | G | A | G | T | A | T | T | G | G | G | A | C | G | A | | | | | | | | | | | | 19 |
| CI105(105) | 5' HLA-A Ex2 152–170 | G | A | T | A | G | A | G | C | A | G | G | A | G | A | G | G | C | C | T | | | | | | | | | | | | 19 |
| CI106(106) | 5' HLA-A & B Ex2 210–229 | T | C | A | C | A | G | A | C | T | G | A | C | C | G | A | G | A | G | A | G | | | | | | | | | | | 20 |
| CI107(107) | 5' HLA-A Ex2 37–53 | C | C | C | G | G | C | C | C | G | G | C | A | G | T | G | G | A | | | | | | | | | | | | | | 17 |
| CI108(105) | 5' HLA-A Ex2 149–167 | G | T | G | G | A | T | A | G | A | G | C | A | G | G | A | G | G | G | T | | | | | | | | | | | | 19 |
| CI109(109) | 3' HLA-A Ex3 80–100 | A | T | G | T | A | A | T | C | C | T | T | G | C | C | G | T | C | G | T | A | A | | | | | | | | | | 21 |
| CI110(110) | 3' HLA-A Ex3 212–229 | C | A | C | T | C | C | A | C | G | C | A | C | G | T | G | C | C | A | | | | | | | | | | | | | 18 |
| CI111(111) | 3' HLA-A Ex3 105–123 | A | G | C | G | C | A | G | G | T | C | C | T | C | G | T | T | C | A | A | | | | | | | | | | | | 19 |
| CI112(112) | 3' HLA-A Ex3 71–88 | C | C | G | T | C | G | T | A | G | G | C | G | T | G | C | T | G | T | | | | | | | | | | | | | 18 |
| CI113(113) | 3' HLA-A Ex3 110–128 | C | C | A | A | G | A | G | C | G | C | A | G | G | T | C | C | T | C | T | | | | | | | | | | | | 19 |
| CI114(114) | 5' HLA-B Ex2 189–209 | A | C | A | C | A | G | A | T | C | T | A | C | A | A | G | A | C | C | A | A | C | | | | | | | | | | 21 |
| CI115(115) | 5' HLA-C Ex2 179–197 | G | G | A | C | C | G | G | G | A | G | A | C | A | C | A | G | A | A | C | | | | | | | | | | | | 19 |
| CI116(116) | 3' HLA-C Ex3 25–41 | C | C | C | C | A | G | G | T | C | G | C | A | G | C | C | A | C | | | | | | | | | | | | | | 17 |
| CI117(117) | 3' HLA-C Ex3 183–200 | T | C | T | C | A | G | C | T | G | C | T | C | C | G | C | C | G | T | | | | | | | | | | | | | 18 |
| CI118(118) | 3' HLA-C Ex3 169–186 | C | T | C | A | C | G | G | G | C | C | G | C | C | T | C | C | A | | | | | | | | | | | | | | 17 |
| CI119(119) | 5' HLA-C Ex2 221–239 | C | C | G | A | G | T | G | A | A | C | C | T | G | C | G | G | A | A | A | | | | | | | | | | | | 19 |
| CI120(120) | 5' HLA-C Ex2 249–268 | T | A | C | T | A | C | A | A | C | C | A | G | A | G | C | G | A | G | G | A | | | | | | | | | | | 20 |
| CI121(121) | 5' HLA-B & C Ex2 210–228 | C | A | C | A | G | A | C | T | G | A | C | C | G | A | G | T | G | A | G | | | | | | | | | | | | 19 |
| CI122(122) | 5' HLA-C Ex2 123–140 | A | G | T | C | C | A | A | G | A | G | G | G | G | A | G | C | C | G | | | | | | | | | | | | | 18 |
| CI123(123) | 5' HLA-A & C Ex2 5–25 | C | C | A | C | T | C | C | A | T | G | A | G | G | T | A | T | T | T | C | T | C | | | | | | | | | | 21 |
| CI124(124) | 3' HLA-B & C Ex3 195–213 | C | C | T | C | C | A | G | G | T | A | G | G | C | T | C | T | C | C | A | | | | | | | | | | | | 19 |
| CI125(125) | 3' HLA-C Ex4 234–251 | C | A | G | C | C | C | C | T | C | G | T | G | C | T | G | C | A | T | | | | | | | | | | | | 18 | |
| CI126(126) | 3' HLA-C Ex3 258–275 | C | G | C | G | C | G | C | T | G | C | A | G | C | G | T | C | T | T | | | | | | | | | | | | 18 | |
| CI127(127) | 3' HLA-C Ex3 195–213 | C | C | T | C | C | A | G | G | T | A | G | G | C | T | C | T | C | A | G | | | | | | | | | | | | 19 |
| CI128(128) | 3' HLA-C Ex3 18–36 | G | G | T | C | G | C | A | G | C | C | A | A | A | C | A | T | C | C | A | | | | | | | | | | | | 19 |
| CI129(129) | 3' HLA-C Ex3 246–265 | A | G | C | G | T | C | T | C | C | T | T | C | C | C | A | T | T | C | T | T | | | | | | | | | | | 20 |
| CI130(130) | 5' HLA-B Ex2 219–236 | T | A | C | C | G | A | G | A | G | A | A | C | C | T | G | C | G | C | A | | | | | | | | | | | | 19 |
| CI131(131) | 3' HLA-B & C Ex3 76–93 | C | C | T | T | G | C | C | G | T | C | G | T | A | G | G | C | G | A | | | | | | | | | | | | | 18 |
| CI132(132) | 3' HLA-B Ex3 69–86 | G | T | C | G | T | A | G | G | C | G | T | C | C | T | G | G | T | C | | | | | | | | | | | | | 18 |
| CI133(133) | 3' HLA-A Ex3 20–39 | C | C | A | C | G | T | C | G | C | A | G | C | C | A | T | A | C | A | T | T | | | | | | | | | | | 20 |
| CI134(134) | 5' HLA-B & C Ex2 117–133 MM | G | C | C | G | C | G | A | G | T | T | C | G | A | G | A | G | G | | | | | | | | | | | | | | 17 |
| CI135(135) | 5' HLA-B Ex2 220–238 | A | C | C | G | A | G | A | G | A | A | C | C | T | G | C | G | G | A | T | | | | | | | | | | | | 19 |
| CI136(136) | 3' HLA-A Ex2 186–205 | G | C | C | T | T | C | A | C | A | T | T | C | C | G | T | G | T | G | T | T | | | | | | | | | | | 20 |
| CI137(137) | 3' HLA-A Ex3 216–232 | A | G | C | C | C | G | T | C | C | A | C | G | C | A | C | C | G | | | | | | | | | | | | | | 17 |

TABLE 1-continued

| Primer (SEQ ID NO:) | | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | MER |
|---|---|---|---|---|---|---|---|---|---|---|---|---|---|---|---|---|---|---|---|---|---|---|---|---|---|---|---|---|---|---|---|---|---|
| | | | SEQUENCE (5'-3') | | | | | | | | | | | | | | | | | | | | | | | | | | | | | | |
| CI138(138) | 5' | HLA-A Ex2 5–25 | C | C | A | C | T | C | C | A | T | G | A | G | G | T | A | T | T | T | C | A | C | | | | | | | | | | 21 |
| CI139(139) | 5' | HLA-B Ex2 230–246 | C | C | T | G | C | G | C | A | C | C | G | C | G | C | T | C | C | | | | | | | | | | | | | | 17 |
| CI140(140) | 3' | HLA-A & B 224–262 | C | T | C | T | G | G | T | T | G | T | A | G | T | A | G | C | G | G | A | | | | | | | | | | | | 19 |
| CI141(141) | 5' | HLA-A Ex3 63–80 | G | G | G | T | A | C | C | G | G | C | A | G | G | A | C | G | C | T | | | | | | | | | | | | | 18 |
| CI142(142) | 5' | HLA-A Ex2 191–209 | A | C | G | G | A | A | A | G | T | G | A | A | G | G | C | C | C | A | G | | | | | | | | | | | | 19 |
| CI143(143) | ? | HLA-A Ex2 184–203 | C | T | T | C | A | C | A | T | T | C | C | G | T | G | T | C | T | C | C | T | | | | | | | | | | | 20 |
| CI144(144) | 5' | HLA-A Ex2 89–107 | C | A | C | G | C | A | G | T | T | C | G | T | G | C | G | G | T | T | T | | | | | | | | | | | | 19 |
| CI145(145) | 3' | HLA-A Ex2 226–43 | G | C | A | G | G | G | T | C | C | C | C | A | G | G | T | C | C | A | | | | | | | | | | | | | 18 |
| CI146(146) | 3' | HLA-B | G | C | T | C | T | G | G | T | T | G | T | A | G | T | A | G | C | G | G | A | | | | | | | | | | | 20 |
| CI147(147) | 5' | HLA-B | G | A | C | G | A | C | A | C | G | C | T | G | T | T | C | G | T | G | A | | | | | | | | | | | | 19 |
| CI148(163) | 5' | Internal Control | T | G | C | C | A | A | G | T | G | G | A | G | C | A | C | C | C | A | A | | | | | | | | | | | | 19 |
| CI149(164) | 3' | Internal Conrol | G | C | A | T | C | T | T | G | C | T | C | T | G | T | G | C | A | G | A | T | | | | | | | | | | | 20 |
| CI150(148) | 5' | HLA-C Ex2 5–23 | A | C | G | T | C | G | C | A | G | C | C | G | T | A | C | A | T | G | | | | | | | | | | | | | 18 |
| C2F30T(149) | 5' | HLA-C Ex2 12–30 | T | C | C | A | T | G | A | A | G | T | A | T | T | T | C | A | C | A | T | | | | | | | | | | | | 19 |
| C2F32T(150) | 5' | HLA-C Ex2 14–32 | C | A | T | G | A | G | G | T | A | T | T | T | C | T | A | C | A | C | C | G | C | T | | | | | | | | | 22 |
| C2F25A(151) | 5' | HLA-C Ex2 5–25 | C | A | C | T | C | C | A | T | G | A | G | G | T | A | T | T | T | C | G | A | | | | | | | | | | | 20 |
| C2F25C(152) | 5' | HLA-C Ex 5–25 | C | A | C | T | C | C | A | T | G | A | G | G | T | A | T | T | T | C | T | C | | | | | | | | | | | 20 |
| C2F32C(153) | 5' | HLA-C Ex2 14–32 | T | G | A | G | G | T | A | T | T | T | C | T | A | C | A | C | C | G | C | C | | | | | | | | | | | 20 |
| C3R195G(154) | 3' | HLAC Ex3 195–213 | C | C | T | C | C | A | G | G | T | A | G | G | C | T | C | T | G | T | C | | | | | | | | | | | | 19 |
| C3R195C(155) | 3' | HLA-C Ex3 195–213 | C | T | C | C | A | G | G | T | A | G | G | C | T | C | T | C | C | G | | | | | | | | | | | | | 18 |
| C3R076A(156) | 3' | HLA-C Ex3 76–93 | C | C | T | T | G | C | C | G | T | C | G | T | A | G | G | C | G | T | | | | | | | | | | | | | 18 |
| C3R076C(157) | 3' | HLA-C Ex3 76–93 | C | C | T | T | G | C | C | G | T | C | G | T | A | G | G | C | G | G | | | | | | | | | | | | | 18 |
| C3R076T(158) | 3' | HLA-C Ex3 76–93 | C | C | T | T | G | C | C | G | T | C | G | T | A | G | G | C | G | A | | | | | | | | | | | | | 18 |
| C3R075TA(159) | 3' | HLA-C Ex3 75–93 | C | C | T | T | G | C | C | G | T | C | G | T | A | G | G | C | T | A | | | | | | | | | | | | | 18 |
| C2F216A(160) | 5' | HLA-C Ex2 198–216 | T | A | C | A | A | G | C | G | C | C | A | G | G | C | A | C | A | G | A | | | | | | | | | | | | 19 |
| | | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | |
| CICptA1(163) | | Class I Capturn Oligo A1 | A | C | G | C | C | T | A | C | G | A | C | G | G | C | A | A | G | G | A | T | T | A | C | A | T | C | G | C | C | C | |
| CICptA2(164) | | Class I Capture Oligo A2 | G | A | T | G | G | A | G | C | C | G | C | G | G | T | G | G | A | T | A | G | A | G | C | A | G | G | A | G | G | G | |
| CICptB1(165) | | Class I Capture Oligo B1 | C | A | G | T | T | C | G | T | G | A | G | G | T | T | C | G | A | C | A | G | C | G | A | C | G | C | C | | | | |
| CICptB2(166) | | Class I Capture Oligo B2 | C | T | G | C | G | C | G | G | C | T | A | C | T | A | C | A | A | C | C | A | G | A | G | C | G | A | G | G | C | C | |
| | | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | |

TABLE 2

| PRIMER (SEQ ID NO.) | | PRIMER | | | | | | | | | | | | | | SEQUENCE (5'–3') | | | | | | | | | | | | | | | | | | MER | 3' seq |
|---|---|---|---|---|---|---|---|---|---|---|---|---|---|---|---|---|---|---|---|---|---|---|---|---|---|---|---|---|---|---|---|---|---|---|---|---|
| DQ01(169) | 5' | DQB 8V-1 | T | C | C | [CT] | C | G | C | A | G | A | G | G | A | T | T | T | C | G | T | G | | | | | | | | | | | | | | 20 | G |
| DQ02(170) | 5' | DQB 26G-1 | G | G | A | G | C | G | C | G | T | G | C | G | G | G | G | | | | | | | | | | | | | | | | | | | 15 | G |
| DQ03(171) | 5' | DQB 26La-1 | A | C | G | G | A | G | C | G | C | G | T | G | C | G | T | C | T | | | | | | | | | | | | | | | | | 17 | T |
| DQ04(172) | 5' | DQB 26Y-2 | G | G | A | C | G | G | A | G | C | G | C | G | T | G | C | G | T | T | A | | | | | | | | | | | | | | | 19 | A |
| DQ05(173) | 3' | DQB 30H-1R | G | T | A | C | T | C | C | T | C | T | C | G | G | T | T | A | T | A | G | A | T | G | T | G | | | | | | | | | | 24 | C |
| DQ06(174) | 3' | DQB 30S-1R | G | A | T | C | T | C | T | T | C | T | C | G | G | T | T | A | T | A | G | A | T | G | C | | | | | | | | | | | 23 | G |
| DQ07(175) | 3' | DQB 36V-2R | G | T | C | G | C | T | G | T | C | G | A | A | G | C | G | C | A | | | | | | | | | | | | | | | | | 17 | T |
| DQ08(176) | 5' | DQB 55P-1 | T | G | A | C | G | C | C | G | C | T | G | G | G | G | C | C | | | | | | | | | | | | | | | | | | 16 | G |
| DQ09(177) | 3' | DQB 57D-2R | G | C | T | G | T | T | C | C | A | G | T | A | C | T | C | G | G | C | G | T | | | | | | | | | | | | | | 20 | A |
| DQ10(178) | 3' | DQB 57S-2R | G | C | T | G | T | T | C | C | A | G | T | A | C | T | C | G | G | C | G | C | T | | | | | | | | | | | | | 21 | A |
| DQ11(179) | 3' | DQB 57V-1R | G | C | T | G | T | T | C | C | A | G | T | A | C | T | C | G | G | C | A | A | | | | | | | | | | | | | | 20 | T |
| DQ12(180) | 3' | DQB 70R-3R | C | A | A | C | T | C | C | G | C | C | C | G | G | G | T | C | C | T | | | | | | | | | | | | | | | | 18 | A |
| DQ13(181) | 5' | DQB 71K-1 | G | A | A | G | G | A | C | A | T | C | C | T | G | G | A | G | A | G | G | A | A | | | | | | | | | | | | | 21 | A |
| DQ14(182) | 3' | DQB84Q-2R | G | G | T | C | G | T | G | C | G | G | A | G | C | T | C | C | A | A | C | T | G | | | | | | | | | | | | | 21 | C |
| DQ15(183) | 3' | DQB 89G-2R | C | A | C | T | C | T | C | C | T | C | T | G | C | A | G | G | A | T | C | C | C | | | | | | | | | | | | | 21 | G |
| DQCPT1(272) | | | C | A | C | G | T | C | G | C | T | G | T | C | G | A | A | G | C | G | C | A | C | G | T | A | C | T | C | C | T | C | | | | 30 | C |
| DQCPT2(273) | | | C | A | C | G | T | C | G | C | T | G | T | C | G | A | A | G | C | G | G | A | C | G | A | T | C | T | C | C | T | T | | | | 30 | T |
| DQCPT3(274) | | | C | A | C | G | T | C | G | C | T | G | T | C | G | A | A | G | C | G | T | G | C | G | T | A | C | T | C | C | T | C | | | | 30 | C |
| DQCPT4(275) | | | C | A | C | G | T | C | G | C | T | G. | T | C | G | A | A | G | C | G | C | G | C | G | T | A | C | T | C | C | T | C | | | | 30 | C |
| DQCPT5(276) | | | C | A | C | G | T | C | G | C | T | G | T | C | G | A | A | G | C | G | C | A | C | G | T | C | C | T | C | C | T | C | | | | 30 | C |
| DR01(184) | 5' | DR2S9-4 | C | C | C | C | [AC] | C | A | G | C | A | C | G | T | T | T | C | T | T | G | A | | | | | | | | | | | | | | 20 | A |
| DR02(185) | 5' | DR2S10G | | | | | C | C | A | G | C | A | C | G | T | T | T | C | T | T | G | G | A | G | G | | | | | | | | | | | 19 | G |
| DR03(186) | 5' | DR2S10L-1 | | | | | [AC] | C | A | G | C | A | C | G | T | T | T | C | T | T | G | G | A | G | C | T | | | | | | | | | | 20 | T |
| DR04(187) | 5' | DR2S11D-2 | | | | | | | | | C | A | C | G | T | T | T | C | T | T | G | C | A | G | C | A | G | G | A | | | | | | | 19 | A |
| DR05(188) | 5' | DR2S11R-1 | | | | | | | | | C | A | C | G | T | T | T | C | T | T | G | G | A | G | C | T | G | C | G | | | | | | | 19 | G |
| DR06(189) | 5' | DR2S13C-2 | | C | G | T | T | T | C | T | T | G | G | A | G | C | A | G | G | C | T | A | A | G | T | G | | | | | | | | | | 23 | G |
| DR07(190) | 5' | DR2S13G-1 | | C | G | T | T | T | C | T | T | G | G | A | G | T | A | C | T | C | T | A | C | G | G | G | | | | | | | | | | 23 | G |
| DR08(191) | 5' | DR2S13H-2 | A | C | G | T | T | T | C | T | T | G | G | A | G | C | A | G | G | T | T | A | A | A | C | | | | | | | | | | | 23 | C |
| DR09(192) | 5' | DR2S13R-1 | | C | G | T | T | T | C | C | T | G | T | G | G | C | A | G | C | C | T | A | A | G | A | | | | | | | | | | | 22 | A |
| DR10(193) | 5' | DR2S13S-2 | | C | G | T | T | T | C | T | T | G | G | A | G | T | A | C | T | C | T | A | C | G | T | C | | | | | | | | | | 23 | C |
| DR11(194) | 5' | DR2S14K-2 | | C | G | T | T | T | C | C | T | G | T | G | G | C | A | G | G | G | T | A | A | G | T | A | T | A | | | | | | | | 25 | A |
| DR12(195) | 3' | DR2R17-1R | | | | | | | | | | | G | T | T | A | T | G | G | A | A | G | T | A | T | C | T | G | T | C | C | A | G | G | T | 23 | A |
| DR13(196) | 5' | DR2526L-3 | | C | G | G | A | G | C | G | G | G | T | G | C | G | G | T | T | G | | | | | | | | | | | | | | | | 17 | G |
| DR14(197) | 5' | DR2S26L-4 | A | C | G | G | A | G | C | G | G | G | T | G | C | G | G | T | T | G | | | | | | | | | | | | | | | | 18 | G |
| DR15(198) | 3' | DR2R30H-1R | A | C | T | C | C | T | C | C | T | G | G | T | T | A | T | A | G | A | A | G | T | G | | | | | | | | | | | | 22 | C |
| DR16(199) | 3' | DR2R37D-1R | | | | | | G | C | T | G | T | C | G | A | A | G | C | G | C | A | A | G | T | C | | | | | | | | | | | 18 | G |
| DR17(200) | 3' | DR2R37F-2R | | | | T | C | G | C | T | G | T | C | G | A | A | G | C | G | C | A | C | G | A | | | | | | | | | | | | 19 | T |
| DR18(201) | 3' | DR2R37L-1R | | | | | | G | C | T | G | T | C | G | A | A | G | C | G | C | A | G | G | A | G | | | | | | | | | | | 18 | C |
| DR19(202) | 3' | DR2R37N-2R | | | | | C | G | C | T | G | T | C | G | A | A | G | C | G | C | A | C | G | T | T | | | | | | | | | | | 19 | A |
| DR20(203) | 3' | DR2R37S-1R | | | | | | G | C | T | G | T | C | G | A | A | G | C | G | C | A | C | G | G | | | | | | | | | | | | 17 | C |
| DR21(204) | 3' | DR2R37Y-1R | | | | | | G | C | T | G | T | C | G | A | A | G | C | G | C | A | C | G | T | A | | | | | | | | | | | 18 | T |
| DR22(205) | 5' | DR2S37YA-1 | C | G | C | T | G | T | C | G | T | A | G | C | G | C | G | C | G | T | | | | | | | | | | | | | | | | 18 | A |
| DR23(206) | 3' | DR2R47F-2R | | T | C | C | G | T | C | A | C | C | G | C | C | C | G | G | A | | | | | | | | | | | | | | | 16 | T | | |
| DR24(207) | 5' | DR2S52B-3 | G | G | A | G | T | A | C | C | G | G | G | C | G | G | T | G | A | G | | | | | | | | | | | | | | | | 18 | G |
| DR25(208) | 3' | DR2R57D-1R | | | C | T | G | T | T | C | C | A | G | T | A | C | T | C | G | G | C | A | T | | | | | | | | | | | | | 19 | A |

TABLE 2-continued

| PRIMER (SEQ ID NO.) | | PRIMER | SEQUENCE (5'-3') | MER | 3' seq |
|---|---|---|---|---|---|
| DR26(209) | 3' | DR2R57S-1R | T G T T C C A G T A C T C G G C G C T | 19 | A |
| DR27(210) | 3' | DR2R57V-1R | C T G T T C C A G G A C T C G G C G A | 21 | T |
| DR28(211) | 3' | DR2R58E-1R | T C A G G C T G T T C C A G T A C T C C T | 21 | A |
| DR29(212) | 3' | DR2R67F-2R | C G C G C C T G T C T T C C A G G A A | 19 | T |
| DR30(213) | 3' | DR2R67I-2R | C C C G C T C G T C T T C C A G G A T | 19 | A |
| DR31(214) | 3' | DR2R70QR-3 | C A C C G C G G C C C G C C T C T G | 18 | C |
| DR32(215) | 3' | DR2R71A-2R | C A C C G C G G C C C G C G C | 15 | G |
| DR33(216) | 3' | DR2R74E-1R | T G C A A T A G G T G T C C A C C T C | 19 | G |
| DR34(217) | 3' | DR2R74L-1R | T G C A G T A G G T G T C C A C C A G | 19 | C |
| DR35(218) | 3' | DR2R74Q-2R | G T G T C T G C A G T A A T T G T C C A C C T G | 24 | C |
| DR36(219) | 3' | DR2R74R-1R | G T G T C T G C A G T A A T T G T C C A C C C | 23 | G |
| DR37(220) | 3' | DR2R76G-1R | A T G T C T G C A G T A G G T G C | 17 | G |
| DR38(221) | 3' | DR2R81Y-1R | C T C T C C A C C A A C C C G T A G T T G T A | 23 | T |
| DR39(222) | 3' | DR2R86G-1R | T G C A C T G T G A A G C T C T C A C | 19 | G |
| DR40(223) | 3' | DR2R86V-1R | C T G C A C T G T G A A G C T C T C C A | 20 | T |
| DR41(224) | 3' | DR2R78A-1R | C C C C G T A G T T G T G T C T G C A A | 20 | T |
| DR42(225) | 3' | DR2R74C-1R | G C A G T A G G T G T C C A C C G C | 18 | G |
| DR43(226) | 3' | DR2R74T-1R | G C A A T A G G T G T C C A C C T C | 18 | G |
| DR44(227) | 3' | DR2R60T-1R | C C T T C T G G C T G T T C C A G T G | 19 | C |
| DR45(228) | 3' | DR2R60G-1R | T C C T T C T G G C T G T T C C A G G | 19 | C |
| DR46(229) | 3' | DR2R85A-1R | A C A G T G A A G c T C T C C A C A G | 19 | C |
| DR47(230) | 3' | DR2R47F | C T C C G T C A C C G C C C G G A | 17 | T |
| DR48(231) | 3' | DR2R47?-1R | C T C C G T C A C C G C C C G G T A | 18 | T |
| DR49(232) | 3' | DR2R30a | C T C C T C C T G G T T A T G G A A G T G | 21 | C |
| DR50(233) | 3' | DR2R30b | C T C C T C C T G G T T A T G G A A G T A | 21 | T |
| DR51(234) | 3' | DR2R37a | T C G C T G T C G A A G C G C A C G T C | 20 | G |
| DR52(235) | 3' | DR2R37b | C G C T G T C G A A G C G C A C G G A | 19 | T |
| DR53(236) | 3' | DR2R37c | C G C T G T C G A A G C G C A C G T C | 19 | G |
| DR54(237) | 3' | DR2R37d | T C G C T G T C G A A G C G C A G G A | 19 | T |
| DR55(238) | 3' | DR2R37e | T C G C T G T C G A A G C G C A C G A | F9 | T |
| DR56(239) | 3' | DR2R38a | A C G T C G C T G T C G A A G C G C A G | 20 | C |
| DR57(240) | 3' | DR2R45a | T C A C C G C C C G G T A C T C C C T | 19 | A |
| DR58(241) | 3' | DR2R48a | C C A G C T C C G T C A C C G C C T | 18 | A |
| DR59(242) | 3' | DR2R50a | C C G C C C C A G C T C C G T C G | 17 | C |
| DR60(243) | 3' | DR2R57a | G C T G T T C C A G T G C T C C G C A G | 20 | C |
| DR61(244) | 3' | DR2R57b | G C T G T T C C A G T G C T C C G C A T | 20 | A |
| DR62(245) | 3' | DR2R57c | G G C T G T T C C A G T A C T C A G C G | 20 | C |
| DR63(246) | 3' | DR2R57c2 | G C T G T T C C A G T A C T C G G C G A T | 21 | A |
| DR64(247) | 3' | DR2R58a | T T C T G G C T G T T C C A G T A C T C A | 21 | T |
| DR65(248) | 3' | DR2R67a | C C G C C T C T G C T C C A G G A G | 19 | C |
| DR66(249) | 3' | DR2R67b | C C G C G C C T G C T C C A G G A T | 18 | A |
| DR67(250) | 3' | DR2R69a | A C C G C G G C G C G C C T G T C T | 18 | A |
| DR68(251) | 3' | DR2R69b | C C G C G G C C C G C G C C T G C | 17 | G |
| DR69(252) | 3' | DR2R70a | C A C C G C G G C G C G C C T G T T | 18 | A |

TABLE 2-continued

| PRIMER (SEQ ID NO.) | PRIMER | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | MER | 3' seq |
|---|---|---|---|---|---|---|---|---|---|---|---|---|---|---|---|---|---|---|---|---|---|---|---|---|---|---|---|---|---|---|---|---|---|
| | | | | | | | | | | | | | | | | SEQUENCE (5'–3') | | | | | | | | | | | | | | | | | |
| DR70(253) | 3' DR2R70b | C | A | C | C | T | C | G | G | C | C | C | G | C | C | T | C | C | | | | | | | | | | | | | | 17 | G |
| DR71(254) | 3' DR2R71a | | G | T | C | C | A | C | C | G | C | G | G | C | G | C | G | C | G | T | | | | | | | | | | | | 18 | A |
| DR72(255) | 3' DR2R71b | T | G | T | C | C | A | C | C | G | C | G | G | C | C | C | G | C | T | | | | | | | | | | | | | 18 | A |
| DR73(256) | 3' DR2R71c | | | T | C | C | A | C | C | G | C | G | G | C | C | C | G | C | G | C | | | | | | | | | | | | 17 | G |
| DR74(257) | 3' DR2R71c2 | | | T | C | c | A | C | C | G | C | G | G | C | C | C | G | C | T | C | | | | | | | | | | | | 17 | G |
| DR75(258) | 3' DR2R71d | T | G | T | C | C | A | C | C | G | C | G | G | C | C | C | G | C | T | | | | | | | | | | | | | 17 | A |
| DR76(259) | 3' DR2R72a | T | A | G | G | T | G | T | C | C | A | C | C | G | C | G | G | C | G | | | | | | | | | | | | | 18 | C |
| DR77(260) | 3' DR2R72b | G | C | G | C | C | A | C | C | T | G | T | G | G | A | T | G | A | C | G | | | | | | | | | | | | 19 | C |
| DR78(261) | 3' DR2R74b | | | | T | C | T | G | C | A | G | T | A | A | T | T | G | T | C | C | A | C | C | T | G | | | | | | | 21 | C |
| DR79(262) | 3' DR2R74a | | | G | T | C | T | G | C | A | A | T | A | G | G | T | G | T | C | C | A | C | C | T | | | | | | | | 21 | A |
| DR80(263) | 3' DR2R74c | | | | | C | T | G | C | A | G | T | A | G | T | T | G | T | C | C | A | C | C | C | G | | | | | | | 20 | C |
| DR81(264) | 3' DR2R77a | | | C | C | G | T | A | G | T | T | G | T | A | T | C | T | G | C | A | G | T | A | G | T | | | | | | | 22 | A |
| DR82(265) | 3' DR2R77b | | | C | C | G | T | A | G | T | T | G | T | G | T | C | T | G | C | A | G | T | A | G | T | | | | | | | 22 | A |
| DR83(266) | 3' DR2R77b | | C | C | C | G | T | A | G | T | T | G | T | G | T | C | T | G | C | A | G | T | A | A | T | | | | | | | 23 | A |
| DR84(267) | 3' DR2R78a | | C | C | C | G | T | A | G | T | T | G | T | G | T | C | T | G | C | A | C | A | C | | | | | | | | | 21G | |
| DR85(268) | 5' DR2S11A | | | | | | G | A | G | C | A | C | G | T | T | T | C | T | T | G | G | A | G | C | T | G | T | | | | | 21 | T |
| DR86(269) | 5' DR2S14b | | | | | T | T | C | T | T | G | T | G | G | C | A | G | C | T | T | A | A | G | T | T | T | G | A | A | | | 24 | A |
| DRGPT1(277) | DRCPTA | T | G | G | C | G | T | G | G | G | C | G | A | G | G | C | A | G | G | G | T | A | A | C | T | T | C | T | T | T | A | 1 | T |
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 26 | 29 | 30 | | |
| (270) | 5' DPA-E(PC) | G | A | T | C | G | C | C | C | T | G | A | G | G | T | G | A | C | C | G | T | G | | | | | | | | | | 21 | G |
| (271) | 3' DPA-F(PC) | G | T | G | G | G | C | C | C | G | G | G | G | G | T | C | A | T | G | G | C | C | | | | | | | | | | 21 | G |
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | MER | |

TABLE 3

| | | 5' Primer | 3' Primer | Specificity | Size (bp) |
|---|---|---|---|---|---|
| A01 | 1 | CI099 | CI137 | A*0101, 0102 | 629 |
| A02 | 4 | CI099 | CI030 | A*3601 | 630 |
| A03 | 2 | CI108 | CI113 | A*0201–17 | 489 |
| A04 | 3 | CI103 | CI110 | A*0301, 0302 | 628 |
| A05 | 15 | CI102 | CI029 | A*1101, 1102, 6601 | 552 |
| A06 | 6 | CI104 | CI085 | A*2301 | 557 |
| A07 | 5 | CI097 | CI113 | A*2301, A*2401–07 | 464 |
| A08 | 7 | CI104 | CI031 | A*2402–05, 2407 | 557 |
| A09 | 10 | CI106 | CI109 | A*2501 | 400 |
| A10 | 8 | CI077 | CI029, 021 | A*2501, 2601, 2603, 2605, 6601, 6602, 4301 | 170 |
| A11 | 9 | CI041 | CI109 | A*2501, 2601–05, 6601, 6602, 3401, 3402 | 440 |
| A12 | 11 | CI101 | CI109 | A*2601, 2602, 2604, 4301 | 400 |
| B01 | 12 | CI034 | CI109 | A*4301 | 442 |
| B02 | 13 | CI077, 141 | CI030 | A*3401, 3402 | 170 |
| B03 | 14 | CI102, 142 | CI109 | A*3401, 3402, 6601, 6602 | 419 |
| B04 | 16 | CI034 | CI111 | A*2901, 2902 | 465 |
| B05 | 17 | CI107 | CI112 | A*3001–05 | 561 |
| B06 | 18 | CI138 | CI143 | A*3101 | 198 |
| B07 | 19 | CI033 | CI072 | A*3201 | 259 |
| B08 | 21 | CI033 | CI111 | A*3201, 7401 | 628 |
| B09 | 20 | CI138 | CI136 | A*3301–03 | 200 |
| B10 | 22 | CI102 | CI113 | A*6801, 6802, 6901 | 447 |
| B11 | 23 | CI102 | CI032 | A*6901 | 383 |
| B12 | 24 | CI120 | CI100 | A*8001 | 494 |
| C01 | 25 | CI120 | CI133 | A*01, *11, *3601, *3401, *8001 | 300 |
| C02 | 79 | CI051 | CI059 | B*5101–05, 51v, 51GAC, 5201 | 401 |
| C03 | 80 | CI041 | CI059 | B*5101–05, 51v, 51GAC, 7801–02, 1509 | 451 |
| C04 | 81 | CI040 | CI059 | B*5201 | 440 |
| C05 | 77 | CI043 | CI056, 091 | B*3501–09, 3511, 5301 | 389/340 |
| C06 | 28 | CI041 | CI064 | B*0702–05, 8101 | 619 |
| C07 | 29 | CI114 | CI064 | B*0703 | 600 |
| C08 | 30 | CI043 | CI055 | B*0801, 0802, B51GAC, B*4406 | 543 |
| C09 | 31 | CI043 | CI063 | B*0801, 0802 | 606 |
| C10 | 36 | CI046, 089 | CI132, 098 | B*4402–06 | 546/481 |
| C11 | 34 | CI083 | CI058 | B*4501, 45v, 4901, 5001 | 600 |
| C12 | 35 | CI050 | CI062 | B*4501, 45V, 1514 | 536 |
| D01 | 42 | CI081 | CI058 | B*1301–03 | 486 |
| D02 | 43 | CI045 | CI014 | B*1401, 1402 | 389 |
| D03 | 44 | CI048 | CI071 | B*1402, 3904 | 187 |
| D04 | 67 | CI081 | CI086 | B*1501, 1502, 1504–08, 1511, 1512, 1514, 1515, 1519–21, 1525, 1526N, 1528 | 124 |
| D05 | 68 | CI040 | CI057 | B*1501, 1503–07, 1512, 1514, 1519, 1520, 1524, 1525, 4802, 4003, 13 × 15, 1526N | 421 |
| D06 | 70 | CI052 | CI057 | B*1503, 1518, 1523, 1529, 4802, 3907, 72v, Cw0703 | 486 |
| D07 | 72 | CI039 | CI076 | B*1509, 1510, 1518, 1521, 1523 | 562 |
| D08 | 73 | CI081 | CI062, 082 | B*1512, 1514, 1519 | 636/637 |
| D09 | 74 | CI041 | CI124 | B*1508, 1511, 1515, 1522, A*68, 2501, 2601–05, 3401, 6601–02 | 553 |
| D10 | 65 | CI042 | CI067 | B*1516, 1517 | 516 |
| D11 | 47 | CI051, 139 | CI060 | B*3801, 3802 | 498/508 |
| D12 | 48 | CI052 | CI060 | B*3801, 3802, 3901–08, 6701 | 612 |
| E01 | 45 | CI050 | CI060 | B*3901–08, 6701 | 507 |

TABLE 3-continued

| | | 5' Primer | 3' Primer | Specificity | Size (bp) |
|---|---|---|---|---|---|
| E02 | 46 | CI049 | CI060 | B*6701 | 548 |
| E03 | 51 | CI042 | CI066 | B*5701–03 | 351 |
| E04 | 52 | CI081 | CI140 | B*5701–03, 1513, 1516, 1517, 1524, 1301–03, 13 × 15 | 143 |
| E05 | 50 | CI042 | CI056 | B*5801–03 | 374 |
| E06 | 49 | CI051 | CI065 | B*5801, 5104, 5301, 1513 | 319 |
| E07 | 53 | CI037 | CI057 | B*1801, 1802 | 458 |
| E08 | 41 | CI094 | CI070 | B*4001, 4007 | 607 |
| E09 | 40 | CI089 | CI061 | B*4001–04, 4006–08, 4701 | 627 |
| E10 | 38 | CI089 | CI090 | B*4002–06, 4008, 4101, 4102, 4501, 45v, 4901, 5001, 4402–05, 4701 | 566 |
| E11 | 33 | CI051 | CI058 | B*4901, 5901 | 385 |
| E12 | 32 | CI094 | CI067 | B*4901, 5001, 4005, 2704, 2706, 45v | 635 |
| F01 | 57 | CI134 | CI074 | B*5401 | 421 |
| F02 | 55 | CI080 | CI058 | B*5401, 5501, 5502, 5601, 4501, 45v, 5001 | 383 |
| F03 | 54 | CI052 | CI074 | B*5501, 5502, 5601, 5602, 7301, 3906 | 422 |
| F04 | 56 | CI047 | CI076 | B*5601, 5602 | 551 |
| F05 | 58 | CI094 | CI095, 096 | B*2701–09 | 149/150 |
| F06 | 75 | CI041 | CI065 | B*3501–04, 3506–09, 3511, 5301, 1502, 1513, 5104, 1521, 4406 | 369 |
| F07 | 76 | CI038 | CI075 | B*3501–13, 18, 7801–02, 1522 | 128 |
| F08 | 59 | CI038 | CI055 | B*3701, B*4406, B51GAC | 606 |
| F09 | 60 | CI040 | CI131 | B*3701, 3902, 3908 | 422 |
| F10 | 37 | CI040 | CI063 | B*4101, 4102 | 605 |
| F11 | 63 | CI047 | CIC63 | B*4201, 42v | 594 |
| F12 | 66 | CI078 | CI079 | B*4601 | 459 |
| G01 | 61 | CI040 | CI069 | B*4701 | 414 |
| G02 | 64 | CI052 | CI070 | B*4801, 8101 | 567 |
| G03 | 39 | CI040 | CI084 | B*4801, 4001–06, weak B41 | 465 |
| G04 | 69 | CI088 | CI065 | B*4802 | 487 |
| G05 | 71 | CI088 | CI076 | B*4802, 1503, 1509, 1510, 1518, 1523, 1529, 72v | 691 |
| G06 | 62 | CI120 | CI074 | B*7301 | 289 |
| G07 | 78 | CI050 | CI059 | B*7801–02, 1509 | 400 |
| G08 | 26 | CI051, 087, 092, 139 | CI073 | Bw4 | 1330 |
| G09 | 27 | CI080 | CI073 | Bw6 not B73 | 1340 |
| G10 | 82 | CI121 | CI116 | Cw*0101, 0102 | 341 |
| G11 | 83 | CI119 | CI021 | Cw*0201, 0202, 1701 | 522 |
| G12 | 84 | CI121 | CI129 | Cw*0302, 0303, 0304 | 565 |
| H01 | 85 | CI119 | CI019 | Cw*0401, 0402 | 331 |
| H02 | 86 | CI119 | CI126 | Cw*0501 | 564 |
| H03 | 87 | CI120 | CI014 | Cw*0602 | 297 |
| H04 | 88 | CI015 | CI125 | Cw*0701, 0702, 0703 | 1062 |
| H05 | 89 | CI115 | CI036 | Cw*0701 | 516 |
| H06 | 90 | CI120 | CI035 | Cw*0702, 0703 | 302 |
| H07 | 91 | CI120 | CI076 | Cw*0703, A*2604 | 494 |
| H08 | 92 | CI120 | CI126 | Cw*0704 | 536 |
| H09 | 93 | CI027 | CI028, 117 | Cw*0802 Cw*0801/3 | 161/625 |
| H10 | 94 | CI025 | CI129 | Cw*0303 | 523 |
| H11 | 95 | CI026 | CI129 | Cw0302, C304 | 522 |
| H12 | 96 | Neg. Control | | | 0 |

TABLE 4

| Tray | Mix | Primer S | Primer AS | label | |
|---|---|---|---|---|---|
| A01 | DRM01 | DR13 | DR31 | DR2R70QR | DRB1*0102 |
| A02 | DRM02 | DR13 | DR20 | DR2R37S | DRB1*0101, 0102, 0103, 0104 |

TABLE 4-continued

| Tray | Mix | Primer S | Primer AS | label | |
|---|---|---|---|---|---|
| A03 | DRM03 | DR13 | DR30 | DR2R67I | DRB1*0103 |
| A04 | DRM04 | DR13 | DR39 | DR2R86G | DRB1*0101, 0103 |
| A05 | DRM05 | DR13 | DR40 | DR2R86V | DRB1*0102, 0104 |
| A06 | DRM06 | DR02 | DR39 | DR2R86G | DRB1*1001 |
| A07 | DRM07 | DR02 | DR25 | DR2R57D | DRB1*1001 |
| A08 | DRM08 | DR09 | DR15 | DR2R30H | DRB1*1503 |
| A09 | DRM09 | DR09 | DR17 | DR2R37F | DRB1*1608 |
| A10 | DRM10 | DR09 | DR23 | DR2R47F | DRB1*1501, 1502, 1503, 1504, 1505, 1506, 1508, 1510 |
| A11 | DRM11 | DR09 | DR48 | DR2R47? | DRB1*1507, 16XX |
| A12 | DRM12 | DR09 | DR25 | DR2R57D | DRB1*1502 |
| B01 | DRM13 | DR09 | DR30 | DR2R67I | DRB1*1510, 1605, 1607 |
| B02 | DRM14 | DR09 | DR29 | DR2R67F | DRB1*1601, 1603?, 1604 |
| B03 | DRM15 | DR09 | DR32 | DR2R71A | DRB1*15XX |
| B04 | DRM16 | DR09 | DR34 | DR2R74L | DRB1*1604 |
| B05 | DRM17 | DR09 | DR39 | DR2R86G | DRB1*1502, 16XX |
| B06 | DRM18 | DR09 | DR40 | DR2R86V | DRB1*1501, 1503, 1504, 1505, 1506, 1507, 1509, 1510 |
| B07 | DRM19 | DR10 | DR12 | DR17-1R | DRB1*0301, 0304, 5, 6, 8–16 |
| B08 | DRM20 | DR10 | DR21 | DR2R37Y | DRB1*11XX, 1303, 07, 11–14, 17, 21–25, 30, 33, 37, 38, 44, 45, 1425 |
| B09 | DRM21 | DR10 | DR19 | DR2R37N | DRB1*0301, 02, 05–15, 1109, 16, 20, 28, 1301, 02, 05, 06, 09, 10, 15, 16, 18, 20, 26–29, 31, 32, 34–36, 39–43, 1402, 03, 06, 09, 12, 13, 17–19, 21, 24, 27, 29, 30, 33 |
| B10 | DRM22 | DR10 | DR17 | DR2R37F | DRB1*1110, 12, 13, 17, 1308, 19, 1401, 04, 05, 07, 08, 10, 11, 14–16, 20, 22, 23, 26, 28, 31, 32, 34–36 |
| B11 | DRM23 | DR10 | DR23 | DR2R47F | DRB1*0301, 04, 05, 07–14, 1101–16, 18–36, 38, 39, 1301, 02, 04–06, 14–18, 20–25, 27–31, 34, 35?, 39, 41–45, 1417, 21, 30, 33, 35, |
| B12 | DRM24 | DR10 | DR48 | DR2R47? | DRB1*0302, 03, 06, 1117, 37, 1303, 07, 08, 12, 13, 19, 26, 32, 33, 36–38, 40, 1401–16, 18–20, 22–29, 31, 32, 34, 36 |

TABLE 4-continued

| Tray | Mix | Primer S | Primer AS | label | |
|---|---|---|---|---|---|
| C01 | DRM25 | DR10 | DR25 | DR2R57D | DRB1*0301–07, 11, 13–16, 1301, 02, 05–11, 14–20, 22–25, 27–29, 34–37, 39–42, 44, 1402, 03, 06, 09, 12, 14, 15, 17–21, 23, 24, 27, 29, 30, 33, 36 |
| C02 | DRM26 | DR10 | DR26 | DR2R57S | DRB1*0312, 1303, 04, 12, 13, 21, 30, 32, 33, 38, 1413, |
| C03 | DRM27 | DR10 | DR27 | DR2R57V | DRB1*1331 |
| C04 | DRM28 | DR10 | DR28 | DR2R58E | DRB1*11XX, 1411, |
| C05 | DRM29 | DR10 | DR29 | DR2R67F | DRB1*1101, 03–06, 09–12, 15, 22–25, 27–30, 32, 33, 35, 37–39, 1305, 07, 11, 14, 18, 21, 24, 26, 42, 1415, 22, 25, 27 |
| C06 | DRM30 | DR10 | DR30 | DR2R67I | DRB1*1102, 14, 16, 20, 21, 1301–04, 08, 10, 15, 16, 1922, 23, 27, 28, 31–41, 45, 1416 |
| C07 | DRM31 | DR10 | DR31 | DR2R70QR | DRB1*1126, 34, 1344, 1402, 06, 09, 13, 17, 20, 29, 30, 33 |
| C08 | DRM32 | DR10 | DR34 | DR2R74L | DRB1*0820, 1123, 25, 1313, 18, 1403, 12, 27 |
| C09 | DRM33 | DR10 | DR46 | DR2R85? | DRB1*1106, 21, 1429 |
| C10 | DRM34 | DR10 | DR39 | DR2R86G | DRB1*0302, 05, 09, 14, 17, 1101, 08–12, 14, 15, 19, 20, 23, 24, 26–29, 31–33, 37, 39, 1302, 03, 05, 07, 12–14, 21, 23, 25, 26, 29–31, 33, 34, 36–39, 41, 45, 1402, 03, 07, 09, 13, 14, 19, 22, 24, 25, 27, 30, 36 |
| C11 | DRM35 | DR10 | DR40 | DR2R86V | DRB1*0301, 03, 04, 06–08, 10–13, 15, 16, 0820, 1102–04, 06, 07, 13, 16–18, 21, 25, 34–36, 38, 1301, 04, 06, 08–11, 15, 18–20, 22, 24, 27, 28, 32, 35, 40, 42–44, 1401, 05, 06, 08, 12, 16–18, 20, 21, 23, 26, 29, 32–35 |
| C12 | DRM36 | DR07 | DR21 | DR2R37Y | DRB1*0801–08, 10–15, 17–19, 1105, 1317 |
| D01 | DRM37 | DR07 | DR18 | DR2R37L | DRB1*1201–04, 1206 |

TABLE 4-continued

| Tray | Mix | Primer S | Primer AS | label | |
|---|---|---|---|---|---|
| D02 | DRM38 | DR07 | DR23 | DR2R47F | DRB1*0817, 1105, 1201–06, 1317 |
| D03 | DRM39 | DR07 | DR48 | DR2R47? | DRB1*0801–17, 18, 19, 21, 1404, 11, 15, 28, 31 |
| D04 | DRM40 | DR07 | DR26 | DR2R51S | DRB1*0801, 03, 05, 06, 10, 12, 14, 16–19w |
| D05 | DRM41 | DR07 | DR25 | DR2R57D | DRB1*0802, 04, 09, 13, 15, 21, 1105, 1204, 1317, 1411, 15 |
| D06 | DRM42 | DR07 | DR27 | DR2R57V | DRB1*1201–03, 05, 06 |
| D07 | DRM43 | DR07 | DR28 | DR2R58E | DRB1*1105, 1204, 1411 |
| D08 | DRM44 | DR07 | DR44 | DR2R60? | DRB1*0808, 15, 1404, 28, 31 |
| D09 | DRM45 | DR07 | DR45 | DR2R60? | DRB1*1201–03, 05, 06 |
| D10 | DRM46 | DR07 | DR29 | DR2R67F | DRB1*0801, 02, 04–09, 11, 16, 17, 21, 1105, 1202, 1415 |
| D11 | DRM47 | DR07 | DR34 | DR2R74L | DRB1*0801–04, 06–19,, 21, 1415 |
| D12 | DRM48 | DR07 | DR46 | DR2R85? | DRB1*0812, 1201, 02, 04–06, 1428 |
| E01 | DRM49 | DR07 | DR39 | DR2R86G | DRB1*0801–03, 05, 07–09, 11, 13–19, 21, 1105 |
| E02 | DRM50 | DR07 | DR40 | DR2R86V | DRB1*0804, 06, 10, 12, 1201–06, 1404, 11, 15, 28, 31 |
| E03 | DRM51 | DR08 | DR20 | DR2R37S | DRB1*0406, 19–21 |
| E04 | DRM52 | DR08 | DR21 | DR2R37Y | DRB1*0401–05, 07–18, 22–36, 1122, 1410 |
| E05 | DRM53 | DR08 | DR23 | DR2R47F | DRB1*0428, 35, 1122 |
| E06 | DRM54 | DR08 | DR26 | DR2R57S | DRB1*0405, 09–12, 17, 24, 28–30 |
| E07 | DRM55 | DR08 | DR25 | DR2R57D | DRB1*0401–04, 06–08, 13, 14, 16, 18–23, 25–27, 31–36 |
| E08 | DRM56 | DR08 | DR28 | DR2R58E | DRB1*0415, 1122 |
| E09 | DRM57 | DR08 | DR29 | DR2R67F | DRB1*0415, 25, 36, 1122 |
| E10 | DRM58 | DR08 | DR30 | DR2R67I | DRB1*0402, 12w, 14, 18 |
| E11 | DRM59 | DR08 | DR70 | DR2R70B | DRB1*0401, 09, 13, 16, 21, 22, 26, 33–35 |
| E12 | DRM60 | DR08 | DR33 | DR2R74E | DRB1*0403, 06, 07, 11, 17, 20, 22, 27, 1410 |
| F01 | DRM61 | DR08 | DR34 | DR2R74L | DRB1*0412, 18, 25, 31 |
| F02 | DRM62 | DR08 | DR39 | DR2R86G | DRB1*0401, 05, 07–09, 14, 16, 17, 19–21, 24, 26, 28–31, 33–35, 1122 |
| F03 | DRM63 | DR08 | DR40 | DR2R86V | DRB1*0402–04, 06, 10–13, 15, 18, 22, 23, 25, 27, 32, 36, 1410 |
| F04 | DRM64 | DR11 | DR17 | DR2R37F | DRB1*0701, 03, 04 |
| F05 | DRM65 | DR11 | DR39 | DR2R86G | DRB1*0701, 03, 04 |
| F06 | DRM66 | DR01 | DR27 | DR2R57V | DRB1*0901 |
| F07 | DRM67 | DR01 | DR39 | DR2R86G | DRB1*0901 |
| F08 | DRM68 | DR03 | DR20 | DR2R37S | DRB3*0203 |
| F09 | DRM69 | DR03 | DR21 | DR2R37Y | DRB1*1130 |
| F10 | DRM70 | DR03 | DR19 | DR2R37N | DRB3*0206? |
| F11 | DRM71 | DR03 | DR17 | DR2R37F | DRB3*0301–03 |
| F12 | DRM72 | DR03 | DR26 | DR2R57S | DRB3*0208 |
| G01 | DRM73 | DR03 | DR25 | DR2R57D | DRB3*0107, 0201–06, 10–13 |
| G02 | DRM74 | DR03 | DR35 | DR2R74Q | DRB3*0107, 0201–03, 05–13, 0301, 02 |
| G03 | DRM75 | DR03 | DR36 | DR2R74R | DRB3*0101–06 |
| G04 | DRM76 | DR03 | DR39 | DR2R86G | DRB3*0101–07, 0202, 03, 05–13, 0303 |
| G05 | DRM77 | DR03 | DR40 | DR2R86V | DRB3*0201, 04, 0301, 02 |
| G06 | DRM78 | DR05 | DR25 | DR2R57D | DRB3*0107 |
| G07 | DRM79 | DR05 | DR39 | DR2R86G | DRB3*0101–07 |
| G08 | DRM80 | DR06 | DR37 | DR2R76G | DRB4*0102 |
| G09 | DRM81 | DR06 | DR38 | DR2R81Y | DRB4*0101–04 |
| G10 | DRM82 | DR06 | DR40 | DR2R86V | DRB4*0101–05 |
| G11 | DRM83 | DR04 | DR20 | DR2R37S | NEG |
| G12 | DRM84 | DR04 | DR16 | DR2R37D | DRB5*0101, 04–07, 09 |
| H01 | DRM85 | DR04 | DR29 | DR2R67F | DRB5*0101–05, 08–10 |
| H02 | DRM86 | DR04 | DR32 | DR2R71A | DRB5*0106, 0202–04 |
| H03 | DRM87 | DR04 | DR34 | DR2R74L | DRB5*0104 |
| H04 | DRM88 | DR04 | DR39 | DR2R86G | DRB5*0101–05, 07–10, 0203 |
| H05 | DRM89 | DR04 | DR40 | DR2R86V | DRB5*0106, 0202, 04, 05 |
| | Mix | P1 15.0 ul | | P2 15.0 ul | |

TABLE 5

| ID | | Location | |
|---|---|---|---|
| CI06 | 3' | HLA-C Ex3 243–263 | Biotin |
| CI07 | 3' | HLA-C Ex3 243–263 | Biotin |
| CI08 | 3' | HLA-B&C Ex3 195–213 | Biotin |
| CI09 | 3' | HLA-C Ex4 234–251 | Biotin |
| CI10 | 3' | HLA-C Ex3 258–275 | Biotin |
| CI11 | 3' | HLA-C Ex3 195–213 | Biotin |
| CI12 | 3' | HLA-C Ex4 31–49 | Biotin |
| CI13 | 3' | HLA-C Ex3 134–151 | Biotin |
| CI14 | 3' | HLA-B & C Ex3 18–36 | Biotin |
| CI16 | 3' | HLA-C Ex4 4–23 | Biotin |
| CI17 | 3' | HLA-C Ex4 4–23 | Biotin |
| CI19 | 3' | HLA-C Ex3 25–42 | Biotin |
| CI21 | 3' | HLA-ABC Ex3 216–233 | Biotin |
| CI22 | 3' | HLA-A & C Ex 3 196–214 | Biotin |
| CI23 | 3' | HLA-B & C Ex3 65–84 | Biotin |
| CI24 | 3' | HLA-C Ex3 131–148 | Biotin |
| CI28 | 3' | HLA-C Ex2 229–246 | Biotin |
| CI29 | 3' | HLA-A Ex3 216–233 | Biotin |
| CI30 | 3' | HLA-ABC Ex3 216–233 | Biotin |
| CI31 | 3' | HLA-A Ex3 195–213 | Biotin |
| CI32 | 3' | HLA-A Ex3 48–64 | Biotin |
| CI35 | 3' | HLA-C Ex3 25–41 | Biotin |
| CI36 | 3' | HLA-B & C Ex3 169–185 | Biotin |
| CI44 | 3' | HLA-B Ex2 219–236 | Biotin |
| CI55 | 3' | HLA-B Ex3 195–213 | Biotin |
| CI56 | 3' | HLA-B & C Ex3 44–59 | Biotin |
| CI57 | 3' | HLA-ABC Ex3 76–92 | Biotin |
| CI58 | 3' | HLA-B & C Ex3 77–95 | Biotin |

TABLE 5-continued

| ID | | Location | |
|---|---|---|---|
| CI59 | 3' | HLA-B Ex3 92–111 | Biotin |
| CI60 | 3' | HLA-B Ex3 201–218 | Biotin |
| CI61 | 3' | HLA-ABC Ex3 216–233 | Biotin |
| CI62 | 3' | HLA-B Ex3 229–246 | Biotin |
| CI63 | 3' | HLA-B Ex3 260–276 | Biotin |
| CI64 | 3' | HLA-B Ex3 262–279 | Biotin |
| CI65 | 3' | HLA-B & C Ex3 10–29 | Biotin |
| CI66 | 3' | HLA-B Ex3 18–36 | Biotin |
| CI67 | 3' | HLA-B Ex3 184–201 | Biotin |
| CI68 | 3' | HLA-B & C Ex3 69–87 | Biotin |
| CI69 | 3' | HLA-A & B Ex3 68–85 | Biotin |
| CI70 | 3' | HLA-B Ex3 156–173 | Biotin |
| CI71 | 3' | HLA-B Ex2 173–192 | Biotin |
| CI72 | 3' | HLA-A & B Ex2 246–264 | Biotin |
| CI73 | 3' | HLA-B Ex4 168–187 | Biotin |
| CI74 | 3' | HLA-B Ex3 11–28 | Biotin |
| CI75 | 3' | HLA-B Ex2 229–245 | Biotin |
| CI76 | 3' | HLA-ABC Ex3 216–233 | Biotin |
| CI79 | 3' | HLA-B Ex3 120–136 | Biotin |
| CI82 | 3' | HLA-A &B Ex3 228–245 | Biotin |
| CI84 | 3' | HLA-B Ex3 120–136 | Biotin |
| CI86 | 3' | HLA-B Ex2 226–243 | Biotin |
| CI90 | 3' | HLA-ABC Ex3 156–172 | Biotin |
| CI91 | 3' | HLA-B Ex3 44–60 | Biotin |
| CI95 | 3' | HLA-B Ex2 207–225 | Biotin |
| CI96 | 3' | HLA-B Ex2 207–226 | Biotin |
| CI98 | 3' | HLA-B & C EX3 69–87 | Biotin |
| CI100 | 3' | HLA-ABC Ex3 216–233 | Biotin |
| CI109 | 3' | HLA-A Ex3 80–100 | Biotin |
| CI110 | 3' | HLA-A Ex3 212–229 | Biotin |
| CI111 | 3' | HLA-A Ex3 105–123 | Biotin |
| CI112 | 3' | HLA-A Ex3 71–88 | Biotin |
| CI113 | 3' | HLA-A Ex3 110–128 | Biotin |
| CI116 | 3' | HLA-C Ex3 25–41 | Biotin |
| CI117 | 3' | HLA-C EX3 183–200 | Biotin |
| CI118 | 3' | HLA-C Ex3 169–186 | Biotin |
| CI124 | 3' | HLA-B & C Ex3 195–213 | Biotin |
| CI125 | 3' | HLA-C Ex4 234–251 | Biotin |
| CI126 | 3' | HLA-C Ex3 258–275 | Biotin |
| CI127 | 3' | HLA-C Ex3 195–213 | Biotin |
| CI128 | 3' | HLA-C Ex3 18–36 | Biotin |
| CI129 | 3' | HLA-C Ex3 246–265 | Biotin |
| CI131 | 3' | HLA-B & C Ex3 76–93 | Biotin |
| CI132 | 3' | HLA-B Ex3 69–86 | Biotin |
| CI133 | 3' | HLA-A Ex3 20–39 | Biotin |

TABLE 5-continued

| ID | | Location | |
|---|---|---|---|
| CI136 | 3' | RLA-A Ex2 186–205 | Biotin |
| CI137 | 3' | HLA-A Ex3 216–232 | Biotin |
| CI140 | 3' | HLA-A & B 224–262 | Biotin |
| CI143 | 3' | HLA-A Ex2 184–203 | Biotin |
| CI145 | 3' | HLA-A Ex2 226–43 | Biotin |
| CI146 | 3' | HLA-B | Biotin |
| CI149 | 3' | Internal Control | Biotin |
| C3R195G | 3' | HLA-C Ex3 195–213 | Biotin |
| C3R195C | 3' | HLA-C Ex3 195–213 | Biotin |
| C3R076A | 3' | HLA-C Ex3 76–93 | Biotin |
| C3R076C | 3' | HLA-C Ex3 76–93 | Biotin |
| C3R076T | 3' | HLA-C Ex3 76–93 | Biotin |
| C3R075TA | 3' | HLA-C Ex3 75–93 | Biotin |

TABLE 6

| ID | | | PRIMER |
|---|---|---|---|
| DQ01 | 5' | Biotin | DQB 8V-1 |
| DQ02 | 5' | Biotin | DQB 26G-1 |
| DQ03 | 5' | Biotin | DQB 26La-1 |
| DQ04 | 5' | Biotin | DQB 26Y-2 |
| DQ08 | 5' | Biotin | DQB 55P-1 |
| DQ13 | 5' | Biotin | DQB 71K-1 |
| DR01 | 5' | Biotin | DR2S9-4 |
| DR02 | 5' | Biotin | DR2S10G |
| DR03 | 5' | Biotin | DR2S10L-1 |
| DR04 | 5' | Biotin | DR2S11D-2 |
| DR05 | 5' | Biotin | DR2S11R-1 |
| DR06 | 5' | Biotin | DR2S13C-2 |
| DR07 | 5' | Biotin | DR2S13G-1 |
| DR08 | 5' | Biotin | DR2S13H-2 |
| DR09 | 5' | Biotin | DR2S13R-1 |
| DR10 | 5' | Biotin | DR2S13S-2 |
| DR11 | 5' | Biotin | DR2S14K-2 |
| DR12 | 3' | | DR2R17-1R |
| DR13 | 5' | Biotin | DR2S26L-3 |
| DR14 | 5' | Biotin | DR2S26L-4 |
| DR22 | 5' | Biotin | DR2S37YA-1 |
| DR24 | 5' | Biotin | DR2S52B-3 |
| DR85 | 5' | Biotin | DR2S11A |
| DR86 | 5' | Biotin | DR2S14b |
| | 5' | Biotin | DPA - E (PC) |

| SEQUENCE LISTING | |
|---|---|
| 1. SEQ ID NO:1:C101 | CCGAGTGAACCTGCGGAAA |
| 2. SEQ ID NO:2:C102 | TACTACAACCAGAGCGAGGA |
| 3. SEQ ID NO:3:C103 | CACAGACTGACCGAGTGAG |
| 4. SEQ ID NO:4:C104 | AGTCCAAGAGGGGAGCCG |
| 5. SEQ ID NO:5:C105 | CCACTCCATGAGGTATTTCT |
| 6. SEQ ID NO:6:C106 | TCTTCTCCAGAAGGCACCAT |
| 7. SEQ ID NO:7:C107 | CAGGTCAGTGTGATCTCCA |
| 8. SEQ ID NO:8:C108 | CCTCCAGGTAGGCTCTCCA |
| 9. SEQ ID NO:9:C109 | CAGCCCCTCGTGCTGCAT |
| 10. SEQ ID NO:10:C110 | CGCGCGCTGCAGCGTCTT |
| 11. SEQ ID NO:11:C111 | CCTCCAGGTAGGCTCTCAG |
| 12. SEQ ID NO:12:C112 | CTCAGGGTGAGGGGCTCT |
| 13. SEQ ID NO:13:C113 | TGAGCCGCCGTGTCCGCA |
| 14. SEQ ID NO:14:C114 | GGTCGCAGCCATACATCCA |
| 15. SEQ ID NO:15:C115 | CCGCGGGTATGACCAGTC |
| 16. SEQ ID NO:16:C116 | GCGTCTCCTTCCCGTTCTT |
| 17. SEQ ID NO:17:C117 | AGCGTCTCCTTCCCATTCTT |

-continued

SEQUENCE LISTING

| | |
|---|---|
| 18. SEQ ID NO:18:C118 | TCCGCGGGTATGACCAGTA |
| 19. SEQ ID NO:19:C119 | GCCCCAGGTCGCAGCCAA |
| 20. SEQ ID NO:20:C120 | ACAAGCGCCAGGCACAGG |
| 21. SEQ ID NO:21:C121 | GAGCCACTCCACGCACTC |
| 22. SEQ ID NO:22:C122 | CCCTCCAGGTAGGCTCTCT |
| 23. SEQ ID NO:23:C123 | TCGTAGGCTAACTGGTCATG |
| 24. SEQ ID NO:24:C124 | CCGCCGTGTCCGCGGCA |
| 25. SEQ ID NO:25:C125 | TACAACCAGAGCGAGGCCA |
| 26. SEQ ID NO:26:C126 | ACAACCAGAGCGAGGCCG |
| 27. SEQ ID NO:27:C127 | ACGACACGCAGTTCGTGCA |
| 28. SEQ ID NO:28:C128 | GCGCAGGTTCCGCAGGC |
| 29. SEQ ID NO:29:C129 | GAGCCACTCCACGCACCG |
| 30. SEQ ID NO:30:C130 | GAGCCACTCCACGCACGT |
| 31. SEQ ID NO:31:C131 | CCTCCAGGTAGGCTCTCTG |
| 32. SEQ ID NO:32:C132 | CCGCGGAGGAAGCGCCA |
| 33. SEQ ID NO:33:C133 | CCACTCCATGAGGTATTTCTT |
| 34. SEQ ID NO:34:C134 | CCGGAGTATTGGGACCTGC |
| 35. SEQ ID NO:35:C135 | CCCCAGGTCGCAAGCCAG |
| 36. SEQ ID NO:26:C136 | CGCACGGGCCGCCTCCA |
| 37. SEQ ID NO:37:C137 | GCGCCGTGGATAGAGCAA |
| 38. SEQ ID NO:38:C138 | GCCGCGAGTCCGAGGAC |
| 39. SEQ ID NO:39:C139 | ACCGGAACACACAGATCTG |
| 40. SEQ ID NO:40:C140 | ACCGGGAGACACAGATCTC |
| 41. SEQ ID NO:41:C141 | GGAGTATTGGGACCGGAAC |
| 42. SEQ ID NO:42:C142 | AACATGAAGGCCTCCGCG |
| 43. SEQ ID NO:43:C143 | GACCGGAACACACAGATCTT |
| 44. SEQ ID NO:44:C144 | TACCGAGAGAACCTGCGC |
| 45. SEQ ID NO:45:C145 | AGCAGGAGGGGCCGGAA |
| 46. SEQ ID NO:46:C146 | GGGGAGCCCCGCTTCATT |
| 47. SEQ ID NO:47:C147 | CAGATCTACAAGGCCCAGG |
| 48. SEQ ID NO:48:C148 | CCATGAGGTATTTCTACACCG |
| 49. SEQ ID NO:49:C149 | GACCGGAACACACAGATCTA |
| 50. SEQ ID NO:50:C150 | CCGAGAGAGCCTGCGGGAA |
| 51. SEQ ID NO:51:C151 | ACCGAGAGAACCTGCGGAT |
| 52. SEQ ID NO:52:C152 | CGCCGCGAGTCCGAGAGA |
| 53. SEQ ID NO:55:C155 | CCTCCAGGTAGGCTCTGTC |
| 54. SEQ ID NO:56:C156 | GAGGAGGCGCCCGTCG |
| 55. SEQ ID NO:57:C157 | CTTGCCGTCGTAGGCGG |
| 56. SEQ ID NO:58:C158 | ATCCTTGCCGTCGTAGGCT |
| 57. SEQ ID NO:59:C159 | CGTTCAGGGCGATGTAATCT |
| 58. SEQ ID NO:60:C160 | CGTGCCCTCCAGGTAGGT |
| 59. SEQ ID NO:61:C161 | GAGCCACTCCACGCACTC |
| 60. SEQ ID NO:62:C162 | CCAGGTATCTGCGGAGCG |
| 61. SEQ ID NO:63:C163 | CCGCGCGCTCCAGCGTG |
| 62. SEQ ID NO:64:C164 | TACCAGCGCGCTCCAGCT |
| 63. SEQ ID NO:65:C165 | GCCATACATCCTCTGGATGA |
| 64. SEQ ID NO:66:C166 | CGTCGCAGCCATACATCAC |
| 65. SEQ ID NO:67:C167 | CTCTCAGCTGCTCCGCCT |
| 66. SEQ ID NO:68:C168 | GTCGTAGGCGGACTGGTC |
| 67. SEQ ID NO:69:C169 | TCGTAGGCGTCCTGGTGG |
| 68. SEQ ID NO:70:C170 | CTCCAACTTGCGCTGGGA |
| 69. SEQ ID NO:71:C171 | GTGTGTTCCGGTCCCAATAT |
| 70. SEQ ID NO:72:C172 | CGCTCTGGTTGTAGTAGCG |
| 71. SEQ ID NO:73:C173 | GCCCACTTCTGGAAGGTTCT |
| 72. SEQ ID NO:74:C174 | CCATACATCGTCTGCCAA |
| 73. SEQ ID NO:75:C175 | GCGCAGGTTCCGCAGGC |
| 74. SEQ ID NO:76:C176 | GAGCCACTCCACGCACAG |
| 75. SEQ ID NO:77:C177 | GGGTACCCAGCAGGACGCT |
| 76. SEQ ID NO:78:C178 | GAGACACAGAAGTACAAGCG |
| 77. SEQ ID NO:79:C179 | GCCGCGGTCCAGGAGCT |
| 78. SEQ ID NO:80:C180 | CGAGAGAGCCTGCGGAAC |
| 79. SEQ ID NO:81:C181 | CGCGAGTCCGAGGATGGC |
| 80. SEQ ID NO:82:C182 | CAGGTATCTGCGGAGCCC |
| 81. SEQ ID NO:83:C183 | CCACTCCCATGAGGTATTTCC |
| 82. SEQ ID NO:84:C184 | GCGGCGGTCCAGGAGCG |
| 83. SEQ ID NO:85:C185 | CCTCCAGGTAGGCTCTCAA |
| 84. SEQ ID NO:86:C186 | GCAGGTTCCGCAGGCTCT |
| 85. SEQ ID NO:87:C187 | GGACCTGCGGACCCTGCT |
| 86. SEQ ID NO:88:C188 | GGGAGCCCCGCTTCATCT |
| 87. SEQ ID NO:89:C189 | CGCCACGAGTCCGAGGAA |
| 88. SEQ ID NO:90:C190 | TCCCACTTGCGCTGGGT |
| 89. SEQ ID NO:91:C191 | GGAGGAAGCGCCCGTCG |
| 90. SEQ ID NO:92:C192 | GAGCCTGCGGACCCTGCT |
| 91. SEQ ID NO:93:C193 | CGAGTGGGCCTGCGGAAC |
| 92. SEQ ID NO:94:C194 | GCTACGTGGACGACACGGCT |
| 93. SEQ ID NO:95:C195 | CTCGGTCAGTCTGTGCCTT |
| 94. SEQ ID NO:96:C196 | TCTCGGTAAGTCTGTGCCTT |

-continued

| SEQUENCE LISTING | |
|---|---|
| 95. SEQ ID NO:97:C197 | TATTGGGACGAGGAGACAG |
| 96. SEQ ID NO:98:C198 | CGTCGTAGGCGTACTGGTC |
| 97. SEQ ID NO:99:C199 | CGACGCCGCGAGCCAGAA |
| 98. SEQ ID NO:100:CI100 | GAGCCCGTCCACGCACTC |
| 99. SEQ ID NO:101:CI101 | TCACAGACTGACCGAGCGAA |
| 100. SEQ ID NO:102:CI102 | ACGGAATGTGAAGGCCCAG |
| 101. SEQ ID NO:103:CI103 | AGCGACGCCGCGAGCCA |
| 102. SEQ ID NO:104:CI104 | GGCCGGAGTATTGGGACGA |
| 103. SEQ ID NO:105:CI105 | GATAGAGCAGGAGAGGCCT |
| 104. SEQ ID NO:106:CI106 | TCACAGACTGACCGAGAGAG |
| 105. SEQ ID NO:107:CI107 | CCCGGCCCGGCAGTGGA |
| 106. SEQ ID NO:108:CI108 | GTGGATAGAGCAGGAGGGT |
| 107. SEQ ID NO:109:CI109 | AGTTAATCCTTGCCGTCGTAA |
| 108. SEQ ID NO:110:CI110 | CACTCCACGCACGTGCCA |
| 109. SEQ ID NO:111:CI111 | AGCGCAGGTCCTCGTTCAA |
| 110. SEQ ID NO:112:CI112 | CCGTCGTAGGCGTGCTGT |
| 111. SEQ ID NO:113:CI113 | CCAAGAGCGCAGGTCCTCT |
| 112. SEQ ID NO:114:CI114 | ACACAGATCTACAAGACCAAC |
| 113. SEQ ID NO:115:CI115 | GGACCCGGGAGACACAGAAC |
| 114. SEQ ID NO:116:CI116 | CCCCAGGTCGCAGCCAC |
| 115. SEQ ID NO:117:CI117 | TCTCAGCTGCTCCGCCGT |
| 116. SEQ ID NO:118:CI118 | CTCACGGGCCGCCTCCA |
| 117. SEQ ID NO:119:CI119 | CCGAGTGAACCTGCGGAAA |
| 118. SEQ ID NO:120:CI120 | TACTACAACCAGAGCGAGGA |
| 119. SEQ ID NO:121:CI121 | CACGACTGACCGAGTGAG |
| 120. SEQ ID NO:122:CI122 | AGTCCAAGAGGGGAGCCG |
| 121. SEQ ID NO:123:CI123 | CCACTCCATGAGGTATTTCTC |
| 122. SEQ ID NO:124:CI124 | CCTCCAGGTAGGCTCTCCA |
| 123. SEQ ID NO:125:CI125 | CAGCCCCTCGTGCTGCAT |
| 124. SEQ ID NO:126:CI126 | CGCGCGCTGCAGCGTCTT |
| 125. SEQ ID NO:127:CI127 | CCTCCAGGTAGGCTTCAG |
| 126. SEQ ID NO:128:CI128 | GGTCGCAGCCAAACATCCA |
| 127. SEQ ID NO:129:CI129 | AGCGTCTCCTTCCCATTCTT |
| 128. SEQ ID NO:130:CI130 | TACCGAGAGAACCTGCGCA |
| 129. SEQ ID NO:131:CI131 | CCTTGCCGTCGTAGGCGA |
| 130. SEQ ID NO:132:CI132 | GTCGTAGGCGTCCTGGTC |
| 131. SEQ ID NO:133:CI133 | CCACGTCGCAGCCATACATT |
| 132. SEQ ID NO:134:CI134 | GCCGCGAGTTCGAGAGG |
| 133. SEQ ID NO:135:CI135 | ACCGAGAGAACCTGCGGAT |
| 134. SEQ ID NO:136:CI136 | GCCTTCACATTCCGTGTGTT |
| 135. SEQ ID NO:137:CI137 | AGCCCGTCCACGCACCG |
| 136. SEQ ID NO:138:CI138 | CCACTCCATGAGGTATTTCAC |
| 137. SEQ ID NO:139:CI139 | CCTGCGCACCGCGCTCC |
| 138. SEQ ID NO:140:CI140 | CTCTGGTTGTAGTAGCGGA |
| 139. SEQ ID NO:141:CI141 | GGGTACCGGCAGGACGCT |
| 140. SEQ ID NO:142:CI142 | ACGGAAAGTGAAGGCCCAG |
| 141. SEQ ID NO:143:CI143 | CTTCACATTCCGTGTCTCCT |
| 142. SEQ ID NO:144:CI144 | CACGCAGTTCGTGCGGTTT |
| 143. SEQ ID NO:145:CI145 | GCAGGGTCCCCAGGTCCA |
| 144. SEQ ID NO:146:CI146 | GCTCTGGTTGTAGTAGCGGA |
| 145. SEQ ID NO:147:CI147 | GACGACACGCTGTTCGTGA |
| 146. SEQ ID NO:148:CI148 | ACGTCGCAGCCGTACATG |
| 147. SEQ ID NO:149:C2F30T | TCCATGAAGTATTTCACAT |
| 148. SEQ ID NO:150:C2F32T | CATGAGGTATTTCTACACCGCT |
| 149. SEQ ID NO:151:C2F25A | CACTCCATGAGGTATTTCGA |
| 150. SEQ ID NO:152:C2F25C | CACTCCATGAGGTATTTCTC |
| 151. SEQ ID NO:153:C2F32C | TGAGGTATTTCTACACCGCC |
| 152. SEQ ID NO:154:C3R195G | CCTCCAGGTAGGCTCTGTC |
| 153. SEQ ID NO:155:C3R195C | CTCCAGGTAGGCTCTCCG |
| 154. SEQ ID NO:156:C34076A | CCTTGCCGTCGTAGGCGT |
| 155. SEQ ID NO:157:C34076C | CCTTGCCGTCGTAGGCGG |
| 156. SEQ ID NO:158:C3R076T | CCTTGCCGTCGTAGGCGA |
| 157. SEQ ID NO:159:C3R075TA | CCTTGCCGTCGTAGGCTA |
| 158. SEQ ID NO:160:C2F216A | TACAAGCGCCAGGCACAGA |
| 159. SEQ ID NO:161:CI53 | ATGATGTTGACCTTTCCAGGG |
| 160. SEQ ID NO:162:CI54 | TTCTGTAACTTTTCATCAGTTGC |
| 161. SEQ ID NO:163:CI148 | TGCCAAGTGGAGCACCCAA |
| 162. SEQ ID NO:164:CI149 | GCATCTTGCTCTGTGCAGA |
| 163. SEQ ID NO:165:CICptA1 | ACGCCTACGACGGCAAGGATTACATCGCCC |
| 164. SEQ ID NO:166:CICptA2 | GATGGAGCCGCGGTGGATAGAGCAAGGAGGG |
| 165. SEQ ID NO:167:CICptB1 | CAGTTCGTGAGGTTCGACAGCGACGCC |
| 166. SEQ ID NO:168:CICptB2 | CTGCGCGGCTACTACAACCAGAGCGAGGCC |
| 167. SEQ ID NO:169:DQ01 | TCC[CT]CGCAGAGGATTTCGTG |
| 168. SEQ ID NO:170:DQ02 | GGAGCGCGTGCGGGG |
| 169. SEQ ID NO:171:DQ03 | ACGGAGCGCGTGCGTCT |
| 170. SEQ ID NO:172:DQ04 | GGACGGAGCGCGTGCGTTA |
| 171. SEQ ID NO:173:DQ05 | GTACTCCTCTCGGTTATAGATGTG |

-continued

| SEQUENCE LISTING | |
|---|---|
| 172. SEQ ID NO:174:DQ06 | GATCTCTTCTCGGTTATAGATGC |
| 173. SEQ ID NO:175:DQ07 | GTCGCTGTCGAAGCGCA |
| 174. SEQ ID NO:176:DQ08 | TGACGCCGCTGGGGCC |
| 175. SEQ ID NO:177:DQ09 | GCTGTTCCAGTACTCGGCGT |
| 176. SEQ ID NO:178:DQ10 | GCTGTTCCAGTACTCGGCGCT |
| 177. SEQ ID NO:179:DQ11 | GCTGTTCCAGTACTCGGCAA |
| 178. SEQ ID NO:180:DQ12 | CAACTCCGCCCGGGTCCT |
| 179. SEQ ID NO:181:DQ13 | GAAGGACATCCTGGAGAGGAA |
| 180. SEQ ID NO:182:DQ14 | GGTCGTGCGGAGCTCCAACTG |
| 181. SEQ ID NO:183:DQ15 | CACTCTCCTCTGCAGGATCCC |
| 182. SEQ ID NO:184:DR01 | CCCC[AC]CAGCACGTTTCTTGA |
| 183. SEQ ID NO:185:DR02 | CCAGCACGTTTCTTGGAGG |
| 184. SEQ ID NO:186:DR03 | [AC]CAGCACGTTTCTTGGAGCT |
| 185. SEQ ID NO:187:DR04 | CACGTTTCTTGCAGCAGGA |
| 186. SEQ ID NO:188:DR05 | CACGTTTCTTGGAGCTGCG |
| 187. SEQ ID NO:189:DR06 | CGTTTCTTGGAGCAGGCTAAGTG |
| 188. SEQ ID NO:190:DR07 | CGTTTCTTGGAGTACTCTACGGG |
| 189. SEQ ID NO:191:DR08 | ACGTTTCTTGGAGCAGGTTAAAC |
| 190. SEQ ID NO:192:DR09 | CGTTTCCTGTGGCAGCCTAAGA |
| 191. SEQ ID NO:193:DR10 | CGTTTCTTGGAGTACTCTACGTC |
| 192. SEQ ID NO:194:DR11 | CGTTTCCTGTGGCAGGGTAAGTATA |
| 193. SEQ ID NO:195:DR12 | GTTATGGAAGTATCTGTCCAGGT |
| 194. SEQ ID NO:196:DR13 | CGGAGCGGGTGCGGTTG |
| 195. SEQ ID NO:197:DR14 | ACGGAGCGGGTGCGGTTG |
| 196. SEQ ID NO:198:DR15 | ACTCCTCCTGGTTATAGAAGTG |
| 197. SEQ ID NO:199:DR16 | GCTGTCGAAGCGCAAGTC |
| 198. SEQ ID NO:200:DR17 | TCGCTGTCGAAGCGCACGA |
| 199. SEQ ID NO:201:DR18 | GCTGTCGAAGCGCAGGAG |
| 200. SEQ ID NO:202:DR19 | CGCTGTCGAAGCGCACGTT |
| 201. SEQ ID NO:203:DR20 | GCTGTCGAAGCGCACGG |
| 202. SEQ ID NO:204:DR21 | GCTGTCGAAGCGCACGTA |
| 203. SEQ ID NO:205:DR22 | CGCTGTCGTAGCGCGCGT |
| 204. SEQ ID NO:206:DR23 | TCCGTCACCGCCCGGA |
| 205. SEQ ID NO:207:DR24 | GGAGTACCGGGCGGTGAG |
| 206. SEQ ID NO:208:DR25 | CTGTTCCAGTACTCGGCAT |
| 207. SEQ ID NO:209:DR26 | TGTTCCAGTACTCGGCGCT |
| 208. SEQ ID NO:210:DR27 | CTGTTCCAGGACTCGGCGA |
| 209. SEQ ID NO:211:DR28 | TCAGGCTGTTCCAGTACTCCT |
| 210. SEQ ID NO:212:DR29 | CGCGCCTGTCTTCCAGGAA |
| 211. SEQ ID NO:213:DR30 | CCCGCTCGTCTTCCAGGAT |
| 212. SEQ ID NO:214:DR31 | CACCGCGGCCCGCCTCTG5 |
| 213. SEQ ID NO:215:DR32 | CACCGCGGCCCGCGC |
| 214. SEQ ID NO:216:DR33 | TGCAATAGGTGTCCACCTC |
| 215. SEQ ID NO:217:DR34 | TGCAGTAGGTGTCCACCAG |
| 216. SEQ ID NO:218:DR35 | GTGTCTGCAGTAATTGTCCACCTG |
| 217. SEQ ID NO:219:DR36 | GTGTCTGCAGTAATTGTCCACCC |
| 218. SEQ ID NO:220:DR37 | ATGTCTGCAGTAGGTGC |
| 219. SEQ ID NO:221:DR38 | CTCTCCACCAACCCGTAGTTGTA |
| 220. SEQ ID NO:222:DR39 | TGCACTGTGAAGCTCTCAC |
| 221. SEQ ID NO:223:DR40 | CTGCACTGTGAAGCTCTCCA |
| 222. SEQ ID NO:224:DR41 | CCCCGTAGTTGTGTCTGCAA |
| 223. SEQ ID NO:225:DR42 | GCAGTAGGTGTCCACCGC |
| 224. SEQ ID NO:226:DR43 | GCAATAGGTGTCCACCTC |
| 225. SEQ ID NO:227:DR44 | CCTTCTGGCTGTTCCCAGTG |
| 226. SEQ ID NO:228:DR45 | TCCTTCTGGCTGTTCCAGG |
| 227. SEQ ID NO:229:DR46 | ACAGTGAAGCTCTCCACAG |
| 228. SEQ ID NO:230:DR47 | CTCCGTCACCGCCCGGA |
| 229. SEQ ID NO:231:DR48 | CTCCGTCACCGCCCGGTA |
| 230. SEQ ID NO:232:DR49 | CTCCTCCTGGTTATGGAACTG |
| 231. SEQ ID NO:233:DR50 | CTCCTCCTGGTTATGGAAGTA |
| 232. SEQ ID NO:234:DR51 | TCGCTGTCGAAGCGCACGTCG |
| 233. SEQ ID NO:235:DR52 | CGCTGTCGAAGCGCAACGGAT |
| 234. SEQ ID NO:236:DR53 | CGCTGTCGAAGCGCACGTCG |
| 235. SEQ ID NO:237:DR54 | TCGCTGTCGAAGCGCAGGA |
| 236. SEQ ID NO:238:DR55 | TCGCTGTCGAAGCGCACGA |
| 237. SEQ ID NO:239:DR56 | ACGTCGCTGTCGAAGCGCAG |
| 238. SEQ ID NO:240:DR57 | TCACCGCCCGGTACTCCCT |
| 239. SEQ ID NO:241:DR58 | CCAAGCTCCGTCACCGCCT |
| 240. SEQ ID NO:242:DR59 | CCGCCCCAGCTCCGTCG |
| 241. SEQ ID NO:243:DR60 | GCTGTTCCAGTGCTCCGCAG |
| 242. SEQ ID NO:244:DR61 | GCTGTTCCAGTGCTCCGCAT |
| 243. SEQ ID NO:245:DR62 | GGCTGTTCCAGTACTCAGCG |
| 244. SEQ ID NO:246:DR63 | GCTGTTCCAGTACTCGGCGA |
| 245. SEQ ID NO:247:DR64 | TTCTGGCTGTTCCAGTACTCA |
| 246. SEQ ID NO:248:DR65 | CCGCCTCTGCTCCAGGAG |
| 247. SEQ ID NO:249:DR66 | CCGCGCCTGCTCCAGGAT |
| 248. SEQ ID NO:250:DR67 | ACCGCGGCGCGCCTGTCT |

-continued

| SEQUENCE LISTING | |
|---|---|
| 249. SEQ ID NO:251:DR68 | CCGCGGCCCGCGCCTGC |
| 250. SEQ ID NO:252:DR69 | CACCGCGGCGCGCCTGTT |
| 251. SEQ ID NO:253:DR70 | CACCTCGGCCCGCCTCC |
| 252. SEQ ID NO:254:DR71 | GTCCACCGCGGCGCGCGT |
| 253. SEQ ID NO:255:DR72 | TGTCCACCGCGGCCCGCT |
| 254. SEQ ID NO:256:DR73 | TCCACCGCGGCCCGCGC |
| 255. SEQ ID NO:257:DR74 | TCCACCGCGGCCCGCTC |
| 256. SEQ ID NO:258:DR75 | TGTCCACCGCGGCCCGCT |
| 257. SEQ ID NO:259:DR76 | TAGGTGTCCACCGCGGCG |
| 258. SEQ ID NO:260:DR77 | GCGCCACCTGTGGATGACG |
| 259. SEQ ID NO:261:DR78 | TCTGCAGTAATTGTCCACCTG |
| 260. SEQ ID NO:262:DR79 | GTCTGCAATAGGTGTCCACCT |
| 261. SEQ ID NO:263:DR80 | CTGCAGTAGTTGTCCACCCG |
| 262. SEQ ID NO:264:DR81 | CCGTAGTTGTATCTGCAGTAGT |
| 263. SEQ ID NO:265:DR82 | CCGTAGTTGTGTCTGCAGTAGT |
| 264. SEQ ID NO:266:DR83 | CCCGTAGTTGTGTCTGCAGTAAT |
| 265. SEQ ID NO:267:DR84 | CCCGTAGTTGTGTCTGCACAC |
| 266. SEQ ID NO:268:DR85 | CAGCACGTTTCTTGGAGCTGT |
| 267. SEQ ID NO:269:DR86 | TTCTTGTGGCAGCTTAAGTTTGA |
| 268. SEQ ID NO:270:DPA-E(PC) | GATCCCCCTGAGGTGACCGTG |
| 269. SEQ ID NO:271:DPA-F(PC) | CTGGGCCCGGGGGTCATGGCC |
| 270. SEQ ID NO:272:DQCPT1 | CACGTCGCTGTCGAAGCGCACGTACTCCTC |
| 271. SEQ ID NO:273:DQCPT2 | CACGTCGCTGTCGAAGCGGACGATCTCCTT |
| 272. SEQ ID NO:274:DQCPT3 | CACGTCGCTGTCGAAGCGTGCGTACTCCTC |
| 273. SEQ ID NO:275:DQCPT4 | CACGTCGCTGTCGAAGCGCGCGTACTCCTC |
| 274. SEQ ID NO:276:DQCPT5 | CACGTCGCTGTCGAAGCGCACGTCCTCCTC |
| 275. SEQ ID NO:277:DRCPT1 | DRCP TGGCGTGGGCGAGGCAGGGTAACTTCTTTA |

What is claimed is:

1. A method for identifying an HLA genotype of a subject, the method comprising:

(a) obtaining a sample comprising a template nucleic acid from said subject;

(b) amplifying said template nucleic acid with a plurality of HLA allele-specific forward primers and HLA allele-specific reverse primers to form amplification products, wherein said forward primers or reverse primers comprise a detectable label;

(c) hybridizing said amplification products with an HLA locus-specific capture oligonucleotide immobilized on a solid phase to form a plurality of detectable complexes, wherein the HLA locus-specific capture oligonucleotide comprises SEQ ID NO:277; and (d) detecting said detectable complexes to identify said HLA genotype of said subject.

2. The method according to claim 1, wherein said capture oligonucleotides further comprise a 5' amine group or a 5'(T)5–20 oligonucleotide sequence.

3. The method of claim 1, wherein the HLA locus-specific capture oligonucleotide consists of SEQ ID NO:277.

4. The method according to claim 3, wherein said capture oligonucleotides further comprise a 5' amine group or a 5'(T)5–20 oligonucleotide sequence.

5. A method for identifying an HLA genotype of a subject, the method comprising:

(a) obtaining a sample comprising a template nucleic acid from said subject;

(b) amplifying said template nucleic acid with a plurality of HLA allele-specific forward primers and HLA allele-specific reverse primers to form amplification products, wherein said forward primers or reverse primers comprise a detectable label;

(c) hybridizing said amplification products with an HLA locus-specific capture oligonucleotide to form a plurality of detectable complexes, wherein the HLA locus-specific capture oligonucleotide comprises SEQ ID NO:277;

(d) immobilizing said detectable complexes on a solid phase; and (e) detecting said detectable complexes to identify said HLA genotype of said subject.

6. The method according to claim 5, wherein said capture oligonucleotides further comprise a 5' amine group or a 5'(T)5–20 oligonucleotide sequence.

7. The method of claim 5, wherein the HLA locus-specific capture oligonucleotide consists of SEQ ID NO:277.

8. The method according to claim 7, wherein said capture oligonucleotides further comprise a 5' amine group or a 5'(T)5–20 oligonucleotide sequence.

* * * * *

SEQUENCE LISTING

<160> NUMBER OF SEQ ID NOS: 278

<210> SEQ ID NO 1
<211> LENGTH: 19
<212> TYPE: DNA
<213> ORGANISM: Homo sapiens

<400> SEQUENCE: 1
ccgagtgaac ctgcggaaa 19

<210> SEQ ID NO 2
<211> LENGTH: 20
<212> TYPE: DNA
<213> ORGANISM: Homo sapiens

<400> SEQUENCE: 2
tactacaacc agagcgagga 20

<210> SEQ ID NO 3
<211> LENGTH: 19
<212> TYPE: DNA
<213> ORGANISM: Homo sapiens

<400> SEQUENCE: 3
cacagactga ccgagtgag 19

<210> SEQ ID NO 4
<211> LENGTH: 18
<212> TYPE: DNA
<213> ORGANISM: Homo sapiens

<400> SEQUENCE: 4
agtccaagag gggagccg 18

-continued

<210> SEQ ID NO 5
<211> LENGTH: 20
<212> TYPE: DNA
<213> ORGANISM: Homo sapiens

<400> SEQUENCE: 5
ccactccatg aggtatttct 20

<210> SEQ ID NO 6
<211> LENGTH: 20
<212> TYPE: DNA
<213> ORGANISM: Homo sapiens

<400> SEQUENCE: 6
tcttctccag aaggcaccat 20

<210> SEQ ID NO 7
<211> LENGTH: 19
<212> TYPE: DNA
<213> ORGANISM: Homo sapiens

<400> SEQUENCE: 7
caggtcagtg tgatctcca 19

<210> SEQ ID NO 8
<211> LENGTH: 19
<212> TYPE: DNA
<213> ORGANISM: Homo sapiens

<400> SEQUENCE: 8
cctccaggta ggctctcca 19

<210> SEQ ID NO 9
<211> LENGTH: 18
<212> TYPE: DNA
<213> ORGANISM: Homo sapiens

<400> SEQUENCE: 9
cagcccctcg tgctgcat 18

<210> SEQ ID NO 10
<211> LENGTH: 18
<212> TYPE: DNA
<213> ORGANISM: Homo sapiens

<400> SEQUENCE: 10
cgcgcgctgc agcgtctt 18

<210> SEQ ID NO 11
<211> LENGTH: 19
<212> TYPE: DNA
<213> ORGANISM: Homo sapiens

<400> SEQUENCE: 11
cctccaggta ggctctcag 19

<210> SEQ ID NO 12
<211> LENGTH: 18
<212> TYPE: DNA
<213> ORGANISM: Homo sapiens

<400> SEQUENCE: 12
ctcagggtga ggggctct 18

-continued

<210> SEQ ID NO 13
<211> LENGTH: 18
<212> TYPE: DNA
<213> ORGANISM: Homo sapiens

<400> SEQUENCE: 13
tgagccgccg tgtccgca 18

<210> SEQ ID NO 14
<211> LENGTH: 19
<212> TYPE: DNA
<213> ORGANISM: Homo sapiens

<400> SEQUENCE: 14
ggtcgcagcc atacatcca 19

<210> SEQ ID NO 15
<211> LENGTH: 18
<212> TYPE: DNA
<213> ORGANISM: Homo sapiens

<400> SEQUENCE: 15
ccgcgggtat gaccagtc 18

<210> SEQ ID NO 16
<211> LENGTH: 19
<212> TYPE: DNA
<213> ORGANISM: Homo sapiens

<400> SEQUENCE: 16
gcgtctcctt cccgttctt 19

<210> SEQ ID NO 17
<211> LENGTH: 20
<212> TYPE: DNA
<213> ORGANISM: Homo sapiens

<400> SEQUENCE: 17
agcgtctcct tcccattctt 20

<210> SEQ ID NO 18
<211> LENGTH: 19
<212> TYPE: DNA
<213> ORGANISM: Homo sapiens

<400> SEQUENCE: 18
tccgcgggta tgaccagta 19

<210> SEQ ID NO 19
<211> LENGTH: 18
<212> TYPE: DNA
<213> ORGANISM: Homo sapiens

<400> SEQUENCE: 19
gccccaggtc gcagccaa 18

<210> SEQ ID NO 20
<211> LENGTH: 18
<212> TYPE: DNA
<213> ORGANISM: Homo sapiens

<400> SEQUENCE: 20

-continued acaagcgcca ggcacagg 18

<210> SEQ ID NO 21
<211> LENGTH: 18
<212> TYPE: DNA
<213> ORGANISM: Homo sapiens

<400> SEQUENCE: 21
gagccactcc acgcactc 18

<210> SEQ ID NO 22
<211> LENGTH: 19
<212> TYPE: DNA
<213> ORGANISM: Homo sapiens

<400> SEQUENCE: 22
ccctccaggt aggctctct 19

<210> SEQ ID NO 23
<211> LENGTH: 20
<212> TYPE: DNA
<213> ORGANISM: Homo sapiens

<400> SEQUENCE: 23
tcgtaggcta actggtcatg 20

<210> SEQ ID NO 24
<211> LENGTH: 17
<212> TYPE: DNA
<213> ORGANISM: Homo sapiens

<400> SEQUENCE: 24
ccgccgtgtc cgcggca 17

<210> SEQ ID NO 25
<211> LENGTH: 19
<212> TYPE: DNA
<213> ORGANISM: Homo sapiens

<400> SEQUENCE: 25
tacaaccaga gcgaggcca 19

<210> SEQ ID NO 26
<211> LENGTH: 18
<212> TYPE: DNA
<213> ORGANISM: Homo sapiens

<400> SEQUENCE: 26
acaaccagag cgaggccg 18

<210> SEQ ID NO 27
<211> LENGTH: 19
<212> TYPE: DNA
<213> ORGANISM: Homo sapiens

<400> SEQUENCE: 27
acgacacgca gttcgtgca 19

<210> SEQ ID NO 28
<211> LENGTH: 17
<212> TYPE: DNA
<213> ORGANISM: Homo sapiens

<400> SEQUENCE: 28

-continued gcgcaggttc cgcaggc 17

<210> SEQ ID NO 29
<211> LENGTH: 18
<212> TYPE: DNA
<213> ORGANISM: Homo sapiens

<400> SEQUENCE: 29
gagccactcc acgcaccg 18

<210> SEQ ID NO 30
<211> LENGTH: 18
<212> TYPE: DNA
<213> ORGANISM: Homo sapiens

<400> SEQUENCE: 30
gagccactcc acgcacgt 18

<210> SEQ ID NO 31
<211> LENGTH: 19
<212> TYPE: DNA
<213> ORGANISM: Homo sapiens

<400> SEQUENCE: 31
cctccaggta ggctctctg 19

<210> SEQ ID NO 32
<211> LENGTH: 17
<212> TYPE: DNA
<213> ORGANISM: Homo sapiens

<400> SEQUENCE: 32
ccgcggagga agcgcca 17

<210> SEQ ID NO 33
<211> LENGTH: 21
<212> TYPE: DNA
<213> ORGANISM: Homo sapiens

<400> SEQUENCE: 33
ccactccatg aggtatttct t 21

<210> SEQ ID NO 34
<211> LENGTH: 19
<212> TYPE: DNA
<213> ORGANISM: Homo sapiens

<400> SEQUENCE: 34
ccggagtatt gggacctgc 19

<210> SEQ ID NO 35
<211> LENGTH: 18
<212> TYPE: DNA
<213> ORGANISM: Homo sapiens

<400> SEQUENCE: 35
ccccaggtcg caagccag 18

<210> SEQ ID NO 36
<211> LENGTH: 17
<212> TYPE: DNA
<213> ORGANISM: Homo sapiens -continued

<400> SEQUENCE: 36
cgcacgggcc gcctcca 17

<210> SEQ ID NO 37
<211> LENGTH: 18
<212> TYPE: DNA
<213> ORGANISM: Homo sapiens

<400> SEQUENCE: 37
gcgccgtgga tagagcaa 18

<210> SEQ ID NO 38
<211> LENGTH: 17
<212> TYPE: DNA
<213> ORGANISM: Homo sapiens

<400> SEQUENCE: 38
gccgcgagtc cgaggac 17

<210> SEQ ID NO 39
<211> LENGTH: 19
<212> TYPE: DNA
<213> ORGANISM: Homo sapiens

<400> SEQUENCE: 39
accggaacac acagatctg 19

<210> SEQ ID NO 40
<211> LENGTH: 19
<212> TYPE: DNA
<213> ORGANISM: Homo sapiens

<400> SEQUENCE: 40
accgggagac acagatctc 19

<210> SEQ ID NO 41
<211> LENGTH: 19
<212> TYPE: DNA
<213> ORGANISM: Homo sapiens

<400> SEQUENCE: 41
ggagtattgg gaccggaac 19

<210> SEQ ID NO 42
<211> LENGTH: 18
<212> TYPE: DNA
<213> ORGANISM: Homo sapiens

<400> SEQUENCE: 42
aacatgaagg cctccgcg 18

<210> SEQ ID NO 43
<211> LENGTH: 20
<212> TYPE: DNA
<213> ORGANISM: Homo sapiens

<400> SEQUENCE: 43
gaccggaaca cacagatctt 20

<210> SEQ ID NO 44
<211> LENGTH: 18
<212> TYPE: DNA
<213> ORGANISM: Homo sapiens -continued

<400> SEQUENCE: 44
taccgagaga acctgcgc 18

<210> SEQ ID NO 45
<211> LENGTH: 17
<212> TYPE: DNA
<213> ORGANISM: Homo sapiens

<400> SEQUENCE: 45
agcaggaggg gccggaa 17

<210> SEQ ID NO 46
<211> LENGTH: 18
<212> TYPE: DNA
<213> ORGANISM: Homo sapiens

<400> SEQUENCE: 46
ggggagcccc gcttcatt 18

<210> SEQ ID NO 47
<211> LENGTH: 19
<212> TYPE: DNA
<213> ORGANISM: Homo sapiens

<400> SEQUENCE: 47
cagatctaca aggcccagg 19

<210> SEQ ID NO 48
<211> LENGTH: 21
<212> TYPE: DNA
<213> ORGANISM: Homo sapiens

<400> SEQUENCE: 48
ccatgaggta tttctacacc g 21

<210> SEQ ID NO 49
<211> LENGTH: 20
<212> TYPE: DNA
<213> ORGANISM: Homo sapiens

<400> SEQUENCE: 49
gaccggaaca cacagatcta 20

<210> SEQ ID NO 50
<211> LENGTH: 19
<212> TYPE: DNA
<213> ORGANISM: Homo sapiens

<400> SEQUENCE: 50
ccgagagagc ctgcgggaa 19

<210> SEQ ID NO 51
<211> LENGTH: 19
<212> TYPE: DNA
<213> ORGANISM: Homo sapiens

<400> SEQUENCE: 51
accgagagaa cctgcggat 19

<210> SEQ ID NO 52
<211> LENGTH: 18
<212> TYPE: DNA

-continued

<213> ORGANISM: Homo sapiens

<400> SEQUENCE: 52
cgccgcgagt ccgagaga 18

<210> SEQ ID NO 53
<211> LENGTH:
<212> TYPE:
<213> ORGANISM:

<400> SEQUENCE: 53

00

<210> SEQ ID NO 54
<211> LENGTH:
<212> TYPE:
<213> ORGANISM:

<400> SEQUENCE: 54

00

<210> SEQ ID NO 55
<211> LENGTH: 19
<212> TYPE: DNA
<213> ORGANISM: Homo sapiens

<400> SEQUENCE: 55
cctccaggta ggctctgtc 19

<210> SEQ ID NO 56
<211> LENGTH: 16
<212> TYPE: DNA
<213> ORGANISM: Homo sapiens

<400> SEQUENCE: 56
gaggaggcgc ccgtcg 16

<210> SEQ ID NO 57
<211> LENGTH: 17
<212> TYPE: DNA
<213> ORGANISM: Homo sapiens

<400> SEQUENCE: 57
cttgccgtcg taggcgg 17

<210> SEQ ID NO 58
<211> LENGTH: 19
<212> TYPE: DNA
<213> ORGANISM: Homo sapiens

<400> SEQUENCE: 58
atccttgccg tcgtaggct 19

<210> SEQ ID NO 59
<211> LENGTH: 20
<212> TYPE: DNA
<213> ORGANISM: Homo sapiens

<400> SEQUENCE: 59
cgttcagggc gatgtaatct 20

<210> SEQ ID NO 60
<211> LENGTH: 18

-continued

<212> TYPE: DNA
<213> ORGANISM: Homo sapiens

<400> SEQUENCE: 60
cgtgccctcc aggtaggt 18

<210> SEQ ID NO 61
<211> LENGTH: 18
<212> TYPE: DNA
<213> ORGANISM: Homo sapiens

<400> SEQUENCE: 61
gagccactcc acgcactc 18

<210> SEQ ID NO 62
<211> LENGTH: 18
<212> TYPE: DNA
<213> ORGANISM: Homo sapiens

<400> SEQUENCE: 62
ccaggtatct gcggagcg 18

<210> SEQ ID NO 63
<211> LENGTH: 17
<212> TYPE: DNA
<213> ORGANISM: Homo sapiens

<400> SEQUENCE: 63
ccgcgcgctc cagcgtg 17

<210> SEQ ID NO 64
<211> LENGTH: 18
<212> TYPE: DNA
<213> ORGANISM: Homo sapiens

<400> SEQUENCE: 64
taccagcgcg ctccagct 18

<210> SEQ ID NO 65
<211> LENGTH: 20
<212> TYPE: DNA
<213> ORGANISM: Homo sapiens

<400> SEQUENCE: 65
gccatacatc ctctggatga 20

<210> SEQ ID NO 66
<211> LENGTH: 19
<212> TYPE: DNA
<213> ORGANISM: Homo sapiens

<400> SEQUENCE: 66
cgtcgcagcc atacatcac 19

<210> SEQ ID NO 67
<211> LENGTH: 18
<212> TYPE: DNA
<213> ORGANISM: Homo sapiens

<400> SEQUENCE: 67
ctctcagctg ctccgcct 18

<210> SEQ ID NO 68

-continued

<211> LENGTH: 18
<212> TYPE: DNA
<213> ORGANISM: Homo sapiens

<400> SEQUENCE: 68
gtcgtaggcg gactggtc 18

<210> SEQ ID NO 69
<211> LENGTH: 18
<212> TYPE: DNA
<213> ORGANISM: Homo sapiens

<400> SEQUENCE: 69
tcgtaggcgt cctggtgg 18

<210> SEQ ID NO 70
<211> LENGTH: 18
<212> TYPE: DNA
<213> ORGANISM: Homo sapiens

<400> SEQUENCE: 70
ctccaacttg cgctggga 18

<210> SEQ ID NO 71
<211> LENGTH: 20
<212> TYPE: DNA
<213> ORGANISM: Homo sapiens

<400> SEQUENCE: 71
gtgtgttccg gtcccaatat 20

<210> SEQ ID NO 72
<211> LENGTH: 19
<212> TYPE: DNA
<213> ORGANISM: Homo sapiens

<400> SEQUENCE: 72
cgctctggtt gtagtagcg 19

<210> SEQ ID NO 73
<211> LENGTH: 20
<212> TYPE: DNA
<213> ORGANISM: Homo sapiens

<400> SEQUENCE: 73
gcccacttct ggaaggttct 20

<210> SEQ ID NO 74
<211> LENGTH: 18
<212> TYPE: DNA
<213> ORGANISM: Homo sapiens

<400> SEQUENCE: 74
ccatacatcg tctgccaa 18

<210> SEQ ID NO 75
<211> LENGTH: 17
<212> TYPE: DNA
<213> ORGANISM: Homo sapiens

<400> SEQUENCE: 75
gcgcaggttc cgcaggc 17

-continued

```
<210> SEQ ID NO 76
<211> LENGTH: 18
<212> TYPE: DNA
<213> ORGANISM: Homo sapiens

<400> SEQUENCE: 76

gagccactcc acgcacag                                                  18


<210> SEQ ID NO 77
<211> LENGTH: 19
<212> TYPE: DNA
<213> ORGANISM: Homo sapiens

<400> SEQUENCE: 77

gggtacccag caggacgct                                                 19


<210> SEQ ID NO 78
<211> LENGTH: 20
<212> TYPE: DNA
<213> ORGANISM: Homo sapiens

<400> SEQUENCE: 78

gagacacaga agtacaagcg                                                20


<210> SEQ ID NO 79
<211> LENGTH: 17
<212> TYPE: DNA
<213> ORGANISM: Homo sapiens

<400> SEQUENCE: 79

gccgcggtcc aggagct                                                   17


<210> SEQ ID NO 80
<211> LENGTH: 18
<212> TYPE: DNA
<213> ORGANISM: Homo sapiens

<400> SEQUENCE: 80

cgagagagcc tgcggaac                                                  18


<210> SEQ ID NO 81
<211> LENGTH: 18
<212> TYPE: DNA
<213> ORGANISM: Homo sapiens

<400> SEQUENCE: 81

cgcgagtccg aggatggc                                                  18


<210> SEQ ID NO 82
<211> LENGTH: 18
<212> TYPE: DNA
<213> ORGANISM: Homo sapiens

<400> SEQUENCE: 82

caggtatctg cggagccc                                                  18


<210> SEQ ID NO 83
<211> LENGTH: 21
<212> TYPE: DNA
<213> ORGANISM: Homo sapiens

<400> SEQUENCE: 83

ccactcccat gaggtatttc c                                              21
```

-continued

<210> SEQ ID NO 84
<211> LENGTH: 17
<212> TYPE: DNA
<213> ORGANISM: Homo sapiens

<400> SEQUENCE: 84
gcggcggtcc aggagcg 17

<210> SEQ ID NO 85
<211> LENGTH: 19
<212> TYPE: DNA
<213> ORGANISM: Homo sapiens

<400> SEQUENCE: 85
cctccaggta ggctctcaa 19

<210> SEQ ID NO 86
<211> LENGTH: 18
<212> TYPE: DNA
<213> ORGANISM: Homo sapiens

<400> SEQUENCE: 86
gcaggttccg caggctct 18

<210> SEQ ID NO 87
<211> LENGTH: 18
<212> TYPE: DNA
<213> ORGANISM: Homo sapiens

<400> SEQUENCE: 87
ggacctgcgg accctgct 18

<210> SEQ ID NO 88
<211> LENGTH: 18
<212> TYPE: DNA
<213> ORGANISM: Homo sapiens

<400> SEQUENCE: 88
gggagccccg cttcatct 18

<210> SEQ ID NO 89
<211> LENGTH: 18
<212> TYPE: DNA
<213> ORGANISM: Homo sapiens

<400> SEQUENCE: 89
cgccacgagt ccgaggaa 18

<210> SEQ ID NO 90
<211> LENGTH: 17
<212> TYPE: DNA
<213> ORGANISM: Homo sapiens

<400> SEQUENCE: 90
tcccacttgc gctgggt 17

<210> SEQ ID NO 91
<211> LENGTH: 17
<212> TYPE: DNA
<213> ORGANISM: Homo sapiens

<400> SEQUENCE: 91
ggaggaagcg cccgtcg 17

-continued

<210> SEQ ID NO 92
<211> LENGTH: 18
<212> TYPE: DNA
<213> ORGANISM: Homo sapiens

<400> SEQUENCE: 92
gagcctgcgg accctgct 18

<210> SEQ ID NO 93
<211> LENGTH: 18
<212> TYPE: DNA
<213> ORGANISM: Homo sapiens

<400> SEQUENCE: 93
cgagtgggcc tgcggaac 18

<210> SEQ ID NO 94
<211> LENGTH: 20
<212> TYPE: DNA
<213> ORGANISM: Homo sapiens

<400> SEQUENCE: 94
gctacgtgga cgacacggct 20

<210> SEQ ID NO 95
<211> LENGTH: 19
<212> TYPE: DNA
<213> ORGANISM: Homo sapiens

<400> SEQUENCE: 95
ctcggtcagt ctgtgcctt 19

<210> SEQ ID NO 96
<211> LENGTH: 20
<212> TYPE: DNA
<213> ORGANISM: Homo sapiens

<400> SEQUENCE: 96
tctcggtaag tctgtgcctt 20

<210> SEQ ID NO 97
<211> LENGTH: 19
<212> TYPE: DNA
<213> ORGANISM: Homo sapiens

<400> SEQUENCE: 97
tattgggacg aggagacag 19

<210> SEQ ID NO 98
<211> LENGTH: 19
<212> TYPE: DNA
<213> ORGANISM: Homo sapiens

<400> SEQUENCE: 98
cgtcgtaggc gtactggtc 19

<210> SEQ ID NO 99
<211> LENGTH: 18
<212> TYPE: DNA
<213> ORGANISM: Homo sapiens

<400> SEQUENCE: 99

-continued cgacgccgcg agccagaa 18

<210> SEQ ID NO 100
<211> LENGTH: 18
<212> TYPE: DNA
<213> ORGANISM: Homo sapiens

<400> SEQUENCE: 100
gagcccgtcc acgcactc 18

<210> SEQ ID NO 101
<211> LENGTH: 20
<212> TYPE: DNA
<213> ORGANISM: Homo sapiens

<400> SEQUENCE: 101
tcacagactg accgagcgaa 20

<210> SEQ ID NO 102
<211> LENGTH: 19
<212> TYPE: DNA
<213> ORGANISM: Homo sapiens

<400> SEQUENCE: 102
acggaatgtg aaggcccag 19

<210> SEQ ID NO 103
<211> LENGTH: 17
<212> TYPE: DNA
<213> ORGANISM: Homo sapiens

<400> SEQUENCE: 103
agcgacgccg cgagcca 17

<210> SEQ ID NO 104
<211> LENGTH: 19
<212> TYPE: DNA
<213> ORGANISM: Homo sapiens

<400> SEQUENCE: 104
ggccggagta ttgggacga 19

<210> SEQ ID NO 105
<211> LENGTH: 19
<212> TYPE: DNA
<213> ORGANISM: Homo sapiens

<400> SEQUENCE: 105
gatagagcag gagaggcct 19

<210> SEQ ID NO 106
<211> LENGTH: 20
<212> TYPE: DNA
<213> ORGANISM: Homo sapiens

<400> SEQUENCE: 106
tcacagactg accgagagag 20

<210> SEQ ID NO 107
<211> LENGTH: 17
<212> TYPE: DNA
<213> ORGANISM: Homo sapiens

<400> SEQUENCE: 107

-continued cccggcccgg cagtgga 17

<210> SEQ ID NO 108
<211> LENGTH: 19
<212> TYPE: DNA
<213> ORGANISM: Homo sapiens

<400> SEQUENCE: 108
gtggatagag caggagggt 19

<210> SEQ ID NO 109
<211> LENGTH: 21
<212> TYPE: DNA
<213> ORGANISM: Homo sapiens

<400> SEQUENCE: 109
agttaatcct tgccgtcgta a 21

<210> SEQ ID NO 110
<211> LENGTH: 18
<212> TYPE: DNA
<213> ORGANISM: Homo sapiens

<400> SEQUENCE: 110
cactccacgc acgtgcca 18

<210> SEQ ID NO 111
<211> LENGTH: 19
<212> TYPE: DNA
<213> ORGANISM: Homo sapiens

<400> SEQUENCE: 111
agcgcaggtc ctcgttcaa 19

<210> SEQ ID NO 112
<211> LENGTH: 18
<212> TYPE: DNA
<213> ORGANISM: Homo sapiens

<400> SEQUENCE: 112
ccgtcgtagg cgtgctgt 18

<210> SEQ ID NO 113
<211> LENGTH: 19
<212> TYPE: DNA
<213> ORGANISM: Homo sapiens

<400> SEQUENCE: 113
ccaagagcgc aggtcctct 19

<210> SEQ ID NO 114
<211> LENGTH: 21
<212> TYPE: DNA
<213> ORGANISM: Homo sapiens

<400> SEQUENCE: 114
acacagatct acaagaccaa c 21

<210> SEQ ID NO 115
<211> LENGTH: 20
<212> TYPE: DNA
<213> ORGANISM: Homo sapiens -continued

<400> SEQUENCE: 115
ggacccggga gacacagaac 20

<210> SEQ ID NO 116
<211> LENGTH: 17
<212> TYPE: DNA
<213> ORGANISM: Homo sapiens

<400> SEQUENCE: 116
ccccaggtcg cagccac 17

<210> SEQ ID NO 117
<211> LENGTH: 18
<212> TYPE: DNA
<213> ORGANISM: Homo sapiens

<400> SEQUENCE: 117
tctcagctgc tccgccgt 18

<210> SEQ ID NO 118
<211> LENGTH: 17
<212> TYPE: DNA
<213> ORGANISM: Homo sapiens

<400> SEQUENCE: 118
ctcacgggcc gcctcca 17

<210> SEQ ID NO 119
<211> LENGTH: 19
<212> TYPE: DNA
<213> ORGANISM: Homo sapiens

<400> SEQUENCE: 119
ccgagtgaac ctgcggaaa 19

<210> SEQ ID NO 120
<211> LENGTH: 20
<212> TYPE: DNA
<213> ORGANISM: Homo sapiens

<400> SEQUENCE: 120
tactacaacc agagcgagga 20

<210> SEQ ID NO 121
<211> LENGTH: 18
<212> TYPE: DNA
<213> ORGANISM: Homo sapiens

<400> SEQUENCE: 121
cacgactgac cgagtgag 18

<210> SEQ ID NO 122
<211> LENGTH: 18
<212> TYPE: DNA
<213> ORGANISM: Homo sapiens

<400> SEQUENCE: 122
agtccaagag gggagccg 18

<210> SEQ ID NO 123
<211> LENGTH: 21
<212> TYPE: DNA
<213> ORGANISM: Homo sapiens

<400> SEQUENCE: 123
ccactccatg aggtatttct c 21

<210> SEQ ID NO 124
<211> LENGTH: 19
<212> TYPE: DNA
<213> ORGANISM: Homo sapiens

<400> SEQUENCE: 124
cctccaggta ggctctcca 19

<210> SEQ ID NO 125
<211> LENGTH: 18
<212> TYPE: DNA
<213> ORGANISM: Homo sapiens

<400> SEQUENCE: 125
cagcccctcg tgctgcat 18

<210> SEQ ID NO 126
<211> LENGTH: 18
<212> TYPE: DNA
<213> ORGANISM: Homo sapiens

<400> SEQUENCE: 126
cgcgcgctgc agcgtctt 18

<210> SEQ ID NO 127
<211> LENGTH: 18
<212> TYPE: DNA
<213> ORGANISM: Homo sapiens

<400> SEQUENCE: 127
cctccaggta ggcttcag 18

<210> SEQ ID NO 128
<211> LENGTH: 19
<212> TYPE: DNA
<213> ORGANISM: Homo sapiens

<400> SEQUENCE: 128
ggtcgcagcc aaacatcca 19

<210> SEQ ID NO 129
<211> LENGTH: 20
<212> TYPE: DNA
<213> ORGANISM: Homo sapiens

<400> SEQUENCE: 129
agcgtctcct tcccattctt 20

<210> SEQ ID NO 130
<211> LENGTH: 19
<212> TYPE: DNA
<213> ORGANISM: Homo sapiens

<400> SEQUENCE: 130
taccgagaga acctgcgca 19

<210> SEQ ID NO 131
<211> LENGTH: 18
<212> TYPE: DNA

-continued

<213> ORGANISM: Homo sapiens

<400> SEQUENCE: 131
ccttgccgtc gtaggcga                                            18

<210> SEQ ID NO 132
<211> LENGTH: 18
<212> TYPE: DNA
<213> ORGANISM: Homo sapiens

<400> SEQUENCE: 132
gtcgtaggcg tcctggtc                                            18

<210> SEQ ID NO 133
<211> LENGTH: 20
<212> TYPE: DNA
<213> ORGANISM: Homo sapiens

<400> SEQUENCE: 133
ccacgtcgca gccatacatt                                          20

<210> SEQ ID NO 134
<211> LENGTH: 17
<212> TYPE: DNA
<213> ORGANISM: Homo sapiens

<400> SEQUENCE: 134
gccgcgagtt cgagagg                                             17

<210> SEQ ID NO 135
<211> LENGTH: 19
<212> TYPE: DNA
<213> ORGANISM: Homo sapiens

<400> SEQUENCE: 135
accgagagaa cctgcggat                                           19

<210> SEQ ID NO 136
<211> LENGTH: 20
<212> TYPE: DNA
<213> ORGANISM: Homo sapiens

<400> SEQUENCE: 136
gccttcacat tccgtgtgtt                                          20

<210> SEQ ID NO 137
<211> LENGTH: 17
<212> TYPE: DNA
<213> ORGANISM: Homo sapiens

<400> SEQUENCE: 137
agcccgtcca cgcaccg                                             17

<210> SEQ ID NO 138
<211> LENGTH: 21
<212> TYPE: DNA
<213> ORGANISM: Homo sapiens

<400> SEQUENCE: 138
ccactccatg aggtatttca c                                        21

<210> SEQ ID NO 139
<211> LENGTH: 17

-continued

<212> TYPE: DNA
<213> ORGANISM: Homo sapiens

<400> SEQUENCE: 139
cctgcgcacc gcgctcc 17

<210> SEQ ID NO 140
<211> LENGTH: 19
<212> TYPE: DNA
<213> ORGANISM: Homo sapiens

<400> SEQUENCE: 140
ctctggttgt agtagcgga 19

<210> SEQ ID NO 141
<211> LENGTH: 18
<212> TYPE: DNA
<213> ORGANISM: Homo sapiens

<400> SEQUENCE: 141
gggtaccggc aggacgct 18

<210> SEQ ID NO 142
<211> LENGTH: 19
<212> TYPE: DNA
<213> ORGANISM: Homo sapiens

<400> SEQUENCE: 142
acggaaagtg aaggcccag 19

<210> SEQ ID NO 143
<211> LENGTH: 20
<212> TYPE: DNA
<213> ORGANISM: Homo sapiens

<400> SEQUENCE: 143
cttcacattc cgtgtctcct 20

<210> SEQ ID NO 144
<211> LENGTH: 19
<212> TYPE: DNA
<213> ORGANISM: Homo sapiens

<400> SEQUENCE: 144
cacgcagttc gtgcggttt 19

<210> SEQ ID NO 145
<211> LENGTH: 18
<212> TYPE: DNA
<213> ORGANISM: Homo sapiens

<400> SEQUENCE: 145
gcagggtccc caggtcca 18

<210> SEQ ID NO 146
<211> LENGTH: 20
<212> TYPE: DNA
<213> ORGANISM: Homo sapiens

<400> SEQUENCE: 146
gctctggttg tagtagcgga 20

-continued

<210> SEQ ID NO 147
<211> LENGTH: 19
<212> TYPE: DNA
<213> ORGANISM: Homo sapiens

<400> SEQUENCE: 147
gacgacacgc tgttcgtga 19

<210> SEQ ID NO 148
<211> LENGTH: 18
<212> TYPE: DNA
<213> ORGANISM: Homo sapiens

<400> SEQUENCE: 148
acgtcgcagc cgtacatg 18

<210> SEQ ID NO 149
<211> LENGTH: 19
<212> TYPE: DNA
<213> ORGANISM: Homo sapiens

<400> SEQUENCE: 149
tccatgaagt atttcacat 19

<210> SEQ ID NO 150
<211> LENGTH: 22
<212> TYPE: DNA
<213> ORGANISM: Homo sapiens

<400> SEQUENCE: 150
catgaggtat ttctacaccg ct 22

<210> SEQ ID NO 151
<211> LENGTH: 20
<212> TYPE: DNA
<213> ORGANISM: Homo sapiens

<400> SEQUENCE: 151
cactccatga ggtatttcga 20

<210> SEQ ID NO 152
<211> LENGTH: 20
<212> TYPE: DNA
<213> ORGANISM: Homo sapiens

<400> SEQUENCE: 152
cactccatga ggtatttctc 20

<210> SEQ ID NO 153
<211> LENGTH: 20
<212> TYPE: DNA
<213> ORGANISM: Homo sapiens

<400> SEQUENCE: 153
tgaggtattt ctacaccgcc 20

<210> SEQ ID NO 154
<211> LENGTH: 19
<212> TYPE: DNA
<213> ORGANISM: Homo sapiens

<400> SEQUENCE: 154
cctccaggta ggctctgtc 19

-continued

<210> SEQ ID NO 155
<211> LENGTH: 18
<212> TYPE: DNA
<213> ORGANISM: Homo sapiens

<400> SEQUENCE: 155
ctccaggtag gctctccg 18

<210> SEQ ID NO 156
<211> LENGTH: 18
<212> TYPE: DNA
<213> ORGANISM: Homo sapiens

<400> SEQUENCE: 156
ccttgccgtc gtaggcgt 18

<210> SEQ ID NO 157
<211> LENGTH: 18
<212> TYPE: DNA
<213> ORGANISM: Homo sapiens

<400> SEQUENCE: 157
ccttgccgtc gtaggcgg 18

<210> SEQ ID NO 158
<211> LENGTH: 18
<212> TYPE: DNA
<213> ORGANISM: Homo sapiens

<400> SEQUENCE: 158
ccttgccgtc gtaggcga 18

<210> SEQ ID NO 159
<211> LENGTH: 18
<212> TYPE: DNA
<213> ORGANISM: Homo sapiens

<400> SEQUENCE: 159
ccttgccgtc gtaggcta 18

<210> SEQ ID NO 160
<211> LENGTH: 19
<212> TYPE: DNA
<213> ORGANISM: Homo sapiens

<400> SEQUENCE: 160
tacaagcgcc aggcacaga 19

<210> SEQ ID NO 161
<211> LENGTH: 21
<212> TYPE: DNA
<213> ORGANISM: Homo sapiens

<400> SEQUENCE: 161
atgatgttga cctttccagg g 21

<210> SEQ ID NO 162
<211> LENGTH: 23
<212> TYPE: DNA
<213> ORGANISM: Homo sapiens

<400> SEQUENCE: 162
ttctgtaact tttcatcagt tgc 23

-continued

<210> SEQ ID NO 163
<211> LENGTH: 19
<212> TYPE: DNA
<213> ORGANISM: Homo sapiens

<400> SEQUENCE: 163
tgccaagtgg agcacccaa 19

<210> SEQ ID NO 164
<211> LENGTH: 19
<212> TYPE: DNA
<213> ORGANISM: Homo sapiens

<400> SEQUENCE: 164
gcatcttgct ctgtgcaga 19

<210> SEQ ID NO 165
<211> LENGTH: 30
<212> TYPE: DNA
<213> ORGANISM: Homo sapiens

<400> SEQUENCE: 165
acgcctacga cggcaaggat tacatcgccc 30

<210> SEQ ID NO 166
<211> LENGTH: 31
<212> TYPE: DNA
<213> ORGANISM: Homo sapiens

<400> SEQUENCE: 166
gatggagccg cggtggatag agcaaggagg g 31

<210> SEQ ID NO 167
<211> LENGTH: 27
<212> TYPE: DNA
<213> ORGANISM: Homo sapiens

<400> SEQUENCE: 167
cagttcgtga ggttcgacag cgacgcc 27

<210> SEQ ID NO 168
<211> LENGTH: 30
<212> TYPE: DNA
<213> ORGANISM: Homo sapiens

<400> SEQUENCE: 168
ctgcgcggct actacaacca gagcgaggcc 30

<210> SEQ ID NO 169
<211> LENGTH: 20
<212> TYPE: DNA
<213> ORGANISM: Homo sapiens

<400> SEQUENCE: 169
tccycgcaga ggatttcgtg 20

<210> SEQ ID NO 170
<211> LENGTH: 15
<212> TYPE: DNA
<213> ORGANISM: Homo sapiens

<400> SEQUENCE: 170

-continued ggagcgcgtg cgggg 15

<210> SEQ ID NO 171
<211> LENGTH: 17
<212> TYPE: DNA
<213> ORGANISM: Homo sapiens

<400> SEQUENCE: 171
acggagcgcg tgcgtct 17

<210> SEQ ID NO 172
<211> LENGTH: 19
<212> TYPE: DNA
<213> ORGANISM: Homo sapiens

<400> SEQUENCE: 172
ggacggagcg cgtgcgtta 19

<210> SEQ ID NO 173
<211> LENGTH: 24
<212> TYPE: DNA
<213> ORGANISM: Homo sapiens

<400> SEQUENCE: 173
gtactcctct cggttataga tgtg 24

<210> SEQ ID NO 174
<211> LENGTH: 23
<212> TYPE: DNA
<213> ORGANISM: Homo sapiens

<400> SEQUENCE: 174
gatctcttct cggttataga tgc 23

<210> SEQ ID NO 175
<211> LENGTH: 17
<212> TYPE: DNA
<213> ORGANISM: Homo sapiens

<400> SEQUENCE: 175
gtcgctgtcg aagcgca 17

<210> SEQ ID NO 176
<211> LENGTH: 16
<212> TYPE: DNA
<213> ORGANISM: Homo sapiens

<400> SEQUENCE: 176
tgacgccgct ggggcc 16

<210> SEQ ID NO 177
<211> LENGTH: 20
<212> TYPE: DNA
<213> ORGANISM: Homo sapiens

<400> SEQUENCE: 177
gctgttccag tactcggcgt 20

<210> SEQ ID NO 178
<211> LENGTH: 21
<212> TYPE: DNA
<213> ORGANISM: Homo sapiens

<400> SEQUENCE: 178

-continued gctgttccag tactcggcgc t 21

<210> SEQ ID NO 179
<211> LENGTH: 20
<212> TYPE: DNA
<213> ORGANISM: Homo sapiens

<400> SEQUENCE: 179
gctgttccag tactcggcaa 20

<210> SEQ ID NO 180
<211> LENGTH: 18
<212> TYPE: DNA
<213> ORGANISM: Homo sapiens

<400> SEQUENCE: 180
caactccgcc cgggtcct 18

<210> SEQ ID NO 181
<211> LENGTH: 21
<212> TYPE: DNA
<213> ORGANISM: Homo sapiens

<400> SEQUENCE: 181
gaaggacatc ctggagagga a 21

<210> SEQ ID NO 182
<211> LENGTH: 21
<212> TYPE: DNA
<213> ORGANISM: Homo sapiens

<400> SEQUENCE: 182
ggtcgtgcgg agctccaact g 21

<210> SEQ ID NO 183
<211> LENGTH: 21
<212> TYPE: DNA
<213> ORGANISM: Homo sapiens

<400> SEQUENCE: 183
cactctcctc tgcaggatcc c 21

<210> SEQ ID NO 184
<211> LENGTH: 20
<212> TYPE: DNA
<213> ORGANISM: Homo sapiens

<400> SEQUENCE: 184
ccccmcagca cgtttcttga 20

<210> SEQ ID NO 185
<211> LENGTH: 19
<212> TYPE: DNA
<213> ORGANISM: Homo sapiens

<400> SEQUENCE: 185
ccagcacgtt tcttggagg 19

<210> SEQ ID NO 186
<211> LENGTH: 20
<212> TYPE: DNA
<213> ORGANISM: Homo sapiens -continued

<400> SEQUENCE: 186
mcagcacgtt tcttggagct 20

<210> SEQ ID NO 187
<211> LENGTH: 19
<212> TYPE: DNA
<213> ORGANISM: Homo sapiens

<400> SEQUENCE: 187
cacgtttctt gcagcagga 19

<210> SEQ ID NO 188
<211> LENGTH: 19
<212> TYPE: DNA
<213> ORGANISM: Homo sapiens

<400> SEQUENCE: 188
cacgtttctt ggagctgcg 19

<210> SEQ ID NO 189
<211> LENGTH: 23
<212> TYPE: DNA
<213> ORGANISM: Homo sapiens

<400> SEQUENCE: 189
cgtttcttgg agcaggctaa gtg 23

<210> SEQ ID NO 190
<211> LENGTH: 23
<212> TYPE: DNA
<213> ORGANISM: Homo sapiens

<400> SEQUENCE: 190
cgtttcttgg agtactctac ggg 23

<210> SEQ ID NO 191
<211> LENGTH: 23
<212> TYPE: DNA
<213> ORGANISM: Homo sapiens

<400> SEQUENCE: 191
acgtttcttg gagcaggtta aac 23

<210> SEQ ID NO 192
<211> LENGTH: 22
<212> TYPE: DNA
<213> ORGANISM: Homo sapiens

<400> SEQUENCE: 192
cgtttcctgt ggcagcctaa ga 22

<210> SEQ ID NO 193
<211> LENGTH: 23
<212> TYPE: DNA
<213> ORGANISM: Homo sapiens

<400> SEQUENCE: 193
cgtttcttgg agtactctac gtc 23

<210> SEQ ID NO 194
<211> LENGTH: 25
<212> TYPE: DNA
<213> ORGANISM: Homo sapiens -continued

<400> SEQUENCE: 194
cgtttcctgt ggcagggtaa gtata 25

<210> SEQ ID NO 195
<211> LENGTH: 23
<212> TYPE: DNA
<213> ORGANISM: Homo sapiens

<400> SEQUENCE: 195
gttatggaag tatctgtcca ggt 23

<210> SEQ ID NO 196
<211> LENGTH: 17
<212> TYPE: DNA
<213> ORGANISM: Homo sapiens

<400> SEQUENCE: 196
cggagcgggt gcggttg 17

<210> SEQ ID NO 197
<211> LENGTH: 18
<212> TYPE: DNA
<213> ORGANISM: Homo sapiens

<400> SEQUENCE: 197
acggagcggg tgcggttg 18

<210> SEQ ID NO 198
<211> LENGTH: 22
<212> TYPE: DNA
<213> ORGANISM: Homo sapiens

<400> SEQUENCE: 198
actcctcctg gttatagaag tg 22

<210> SEQ ID NO 199
<211> LENGTH: 18
<212> TYPE: DNA
<213> ORGANISM: Homo sapiens

<400> SEQUENCE: 199
gctgtcgaag cgcaagtc 18

<210> SEQ ID NO 200
<211> LENGTH: 19
<212> TYPE: DNA
<213> ORGANISM: Homo sapiens

<400> SEQUENCE: 200
tcgctgtcga agcgcacga 19

<210> SEQ ID NO 201
<211> LENGTH: 18
<212> TYPE: DNA
<213> ORGANISM: Homo sapiens

<400> SEQUENCE: 201
gctgtcgaag cgcaggag 18

<210> SEQ ID NO 202
<211> LENGTH: 19
<212> TYPE: DNA

-continued

<213> ORGANISM: Homo sapiens

<400> SEQUENCE: 202
cgctgtcgaa gcgcacgtt 19

<210> SEQ ID NO 203
<211> LENGTH: 17
<212> TYPE: DNA
<213> ORGANISM: Homo sapiens

<400> SEQUENCE: 203
gctgtcgaag cgcacgg 17

<210> SEQ ID NO 204
<211> LENGTH: 18
<212> TYPE: DNA
<213> ORGANISM: Homo sapiens

<400> SEQUENCE: 204
gctgtcgaag cgcacgta 18

<210> SEQ ID NO 205
<211> LENGTH: 18
<212> TYPE: DNA
<213> ORGANISM: Homo sapiens

<400> SEQUENCE: 205
cgctgtcgta gcgcgcgt 18

<210> SEQ ID NO 206
<211> LENGTH: 16
<212> TYPE: DNA
<213> ORGANISM: Homo sapiens

<400> SEQUENCE: 206
tccgtcaccg cccgga 16

<210> SEQ ID NO 207
<211> LENGTH: 18
<212> TYPE: DNA
<213> ORGANISM: Homo sapiens

<400> SEQUENCE: 207
ggagtaccgg gcggtgag 18

<210> SEQ ID NO 208
<211> LENGTH: 19
<212> TYPE: DNA
<213> ORGANISM: Homo sapiens

<400> SEQUENCE: 208
ctgttccagt actcggcat 19

<210> SEQ ID NO 209
<211> LENGTH: 19
<212> TYPE: DNA
<213> ORGANISM: Homo sapiens

<400> SEQUENCE: 209
tgttccagta ctcggcgct 19

<210> SEQ ID NO 210
<211> LENGTH: 19

-continued

<212> TYPE: DNA
<213> ORGANISM: Homo sapiens

<400> SEQUENCE: 210
ctgttccagg actcggcga 19

<210> SEQ ID NO 211
<211> LENGTH: 21
<212> TYPE: DNA
<213> ORGANISM: Homo sapiens

<400> SEQUENCE: 211
tcaggctgtt ccagtactcc t 21

<210> SEQ ID NO 212
<211> LENGTH: 19
<212> TYPE: DNA
<213> ORGANISM: Homo sapiens

<400> SEQUENCE: 212
cgcgcctgtc ttccaggaa 19

<210> SEQ ID NO 213
<211> LENGTH: 19
<212> TYPE: DNA
<213> ORGANISM: Homo sapiens

<400> SEQUENCE: 213
cccgctcgtc ttccaggat 19

<210> SEQ ID NO 214
<211> LENGTH: 18
<212> TYPE: DNA
<213> ORGANISM: Homo sapiens

<400> SEQUENCE: 214
caccgcggcc cgcctctg 18

<210> SEQ ID NO 215
<211> LENGTH: 15
<212> TYPE: DNA
<213> ORGANISM: Homo sapiens

<400> SEQUENCE: 215
caccgcggcc cgcgc 15

<210> SEQ ID NO 216
<211> LENGTH: 19
<212> TYPE: DNA
<213> ORGANISM: Homo sapiens

<400> SEQUENCE: 216
tgcaataggt gtccacctc 19

<210> SEQ ID NO 217
<211> LENGTH: 19
<212> TYPE: DNA
<213> ORGANISM: Homo sapiens

<400> SEQUENCE: 217
tgcagtaggt gtccaccag 19

<210> SEQ ID NO 218

-continued

<211> LENGTH: 24
<212> TYPE: DNA
<213> ORGANISM: Homo sapiens

<400> SEQUENCE: 218
gtgtctgcag taattgtcca cctg 24

<210> SEQ ID NO 219
<211> LENGTH: 23
<212> TYPE: DNA
<213> ORGANISM: Homo sapiens

<400> SEQUENCE: 219
gtgtctgcag taattgtcca ccc 23

<210> SEQ ID NO 220
<211> LENGTH: 17
<212> TYPE: DNA
<213> ORGANISM: Homo sapiens

<400> SEQUENCE: 220
atgtctgcag taggtgc 17

<210> SEQ ID NO 221
<211> LENGTH: 23
<212> TYPE: DNA
<213> ORGANISM: Homo sapiens

<400> SEQUENCE: 221
ctctccacca acccgtagtt gta 23

<210> SEQ ID NO 222
<211> LENGTH: 19
<212> TYPE: DNA
<213> ORGANISM: Homo sapiens

<400> SEQUENCE: 222
tgcactgtga agctctcac 19

<210> SEQ ID NO 223
<211> LENGTH: 20
<212> TYPE: DNA
<213> ORGANISM: Homo sapiens

<400> SEQUENCE: 223
ctgcactgtg aagctctcca 20

<210> SEQ ID NO 224
<211> LENGTH: 20
<212> TYPE: DNA
<213> ORGANISM: Homo sapiens

<400> SEQUENCE: 224
ccccgtagtt gtgtctgcaa 20

<210> SEQ ID NO 225
<211> LENGTH: 18
<212> TYPE: DNA
<213> ORGANISM: Homo sapiens

<400> SEQUENCE: 225
gcagtaggtg tccaccgc 18

-continued

<210> SEQ ID NO 226
<211> LENGTH: 18
<212> TYPE: DNA
<213> ORGANISM: Homo sapiens

<400> SEQUENCE: 226
gcaataggtg tccacctc 18

<210> SEQ ID NO 227
<211> LENGTH: 20
<212> TYPE: DNA
<213> ORGANISM: Homo sapiens

<400> SEQUENCE: 227
ccttctggct gttcccagtg 20

<210> SEQ ID NO 228
<211> LENGTH: 19
<212> TYPE: DNA
<213> ORGANISM: Homo sapiens

<400> SEQUENCE: 228
tccttctggc tgttccagg 19

<210> SEQ ID NO 229
<211> LENGTH: 19
<212> TYPE: DNA
<213> ORGANISM: Homo sapiens

<400> SEQUENCE: 229
acagtgaagc tctccacag 19

<210> SEQ ID NO 230
<211> LENGTH: 17
<212> TYPE: DNA
<213> ORGANISM: Homo sapiens

<400> SEQUENCE: 230
ctccgtcacc gcccgga 17

<210> SEQ ID NO 231
<211> LENGTH: 18
<212> TYPE: DNA
<213> ORGANISM: Homo sapiens

<400> SEQUENCE: 231
ctccgtcacc gcccggta 18

<210> SEQ ID NO 232
<211> LENGTH: 21
<212> TYPE: DNA
<213> ORGANISM: Homo sapiens

<400> SEQUENCE: 232
ctcctcctgg ttatggaact g 21

<210> SEQ ID NO 233
<211> LENGTH: 21
<212> TYPE: DNA
<213> ORGANISM: Homo sapiens

<400> SEQUENCE: 233
ctcctcctgg ttatggaagt a 21

<210> SEQ ID NO 234
<211> LENGTH: 21
<212> TYPE: DNA
<213> ORGANISM: Homo sapiens

<400> SEQUENCE: 234
tcgctgtcga agcgcacgtc g 21

<210> SEQ ID NO 235
<211> LENGTH: 21
<212> TYPE: DNA
<213> ORGANISM: Homo sapiens

<400> SEQUENCE: 235
cgctgtcgaa gcgcaacgga t 21

<210> SEQ ID NO 236
<211> LENGTH: 20
<212> TYPE: DNA
<213> ORGANISM: Homo sapiens

<400> SEQUENCE: 236
cgctgtcgaa gcgcacgtcg 20

<210> SEQ ID NO 237
<211> LENGTH: 19
<212> TYPE: DNA
<213> ORGANISM: Homo sapiens

<400> SEQUENCE: 237
tcgctgtcga agcgcagga 19

<210> SEQ ID NO 238
<211> LENGTH: 19
<212> TYPE: DNA
<213> ORGANISM: Homo sapiens

<400> SEQUENCE: 238
tcgctgtcga agcgcacga 19

<210> SEQ ID NO 239
<211> LENGTH: 20
<212> TYPE: DNA
<213> ORGANISM: Homo sapiens

<400> SEQUENCE: 239
acgtcgctgt cgaagcgcag 20

<210> SEQ ID NO 240
<211> LENGTH: 19
<212> TYPE: DNA
<213> ORGANISM: Homo sapiens

<400> SEQUENCE: 240
tcaccgcccg gtactccct 19

<210> SEQ ID NO 241
<211> LENGTH: 19
<212> TYPE: DNA
<213> ORGANISM: Homo sapiens

<400> SEQUENCE: 241
ccaagctccg tcaccgcct 19

-continued

<210> SEQ ID NO 242
<211> LENGTH: 17
<212> TYPE: DNA
<213> ORGANISM: Homo sapiens

<400> SEQUENCE: 242
ccgccccagc tccgtcg 17

<210> SEQ ID NO 243
<211> LENGTH: 20
<212> TYPE: DNA
<213> ORGANISM: Homo sapiens

<400> SEQUENCE: 243
gctgttccag tgctccgcag 20

<210> SEQ ID NO 244
<211> LENGTH: 20
<212> TYPE: DNA
<213> ORGANISM: Homo sapiens

<400> SEQUENCE: 244
gctgttccag tgctccgcat 20

<210> SEQ ID NO 245
<211> LENGTH: 20
<212> TYPE: DNA
<213> ORGANISM: Homo sapiens

<400> SEQUENCE: 245
ggctgttcca gtactcagcg 20

<210> SEQ ID NO 246
<211> LENGTH: 20
<212> TYPE: DNA
<213> ORGANISM: Homo sapiens

<400> SEQUENCE: 246
gctgttccag tactcggcga 20

<210> SEQ ID NO 247
<211> LENGTH: 21
<212> TYPE: DNA
<213> ORGANISM: Homo sapiens

<400> SEQUENCE: 247
ttctggctgt tccagtactc a 21

<210> SEQ ID NO 248
<211> LENGTH: 18
<212> TYPE: DNA
<213> ORGANISM: Homo sapiens

<400> SEQUENCE: 248
ccgcctctgc tccaggag 18

<210> SEQ ID NO 249
<211> LENGTH: 18
<212> TYPE: DNA
<213> ORGANISM: Homo sapiens

<400> SEQUENCE: 249

-continued ccgcgcctgc tccaggat 18

<210> SEQ ID NO 250
<211> LENGTH: 18
<212> TYPE: DNA
<213> ORGANISM: Homo sapiens

<400> SEQUENCE: 250
accgcggcgc gcctgtct 18

<210> SEQ ID NO 251
<211> LENGTH: 17
<212> TYPE: DNA
<213> ORGANISM: Homo sapiens

<400> SEQUENCE: 251
ccgcggcccg cgcctgc 17

<210> SEQ ID NO 252
<211> LENGTH: 18
<212> TYPE: DNA
<213> ORGANISM: Homo sapiens

<400> SEQUENCE: 252
caccgcggcg cgcctgtt 18

<210> SEQ ID NO 253
<211> LENGTH: 17
<212> TYPE: DNA
<213> ORGANISM: Homo sapiens

<400> SEQUENCE: 253
cacctcggcc cgcctcc 17

<210> SEQ ID NO 254
<211> LENGTH: 18
<212> TYPE: DNA
<213> ORGANISM: Homo sapiens

<400> SEQUENCE: 254
gtccaccgcg gcgcgcgt 18

<210> SEQ ID NO 255
<211> LENGTH: 18
<212> TYPE: DNA
<213> ORGANISM: Homo sapiens

<400> SEQUENCE: 255
tgtccaccgc ggcccgct 18

<210> SEQ ID NO 256
<211> LENGTH: 17
<212> TYPE: DNA
<213> ORGANISM: Homo sapiens

<400> SEQUENCE: 256
tccaccgcgg cccgcgc 17

<210> SEQ ID NO 257
<211> LENGTH: 17
<212> TYPE: DNA
<213> ORGANISM: Homo sapiens -continued

<400> SEQUENCE: 257
tccaccgcgg cccgctc 17

<210> SEQ ID NO 258
<211> LENGTH: 18
<212> TYPE: DNA
<213> ORGANISM: Homo sapiens

<400> SEQUENCE: 258
tgtccaccgc ggcccgct 18

<210> SEQ ID NO 259
<211> LENGTH: 18
<212> TYPE: DNA
<213> ORGANISM: Homo sapiens

<400> SEQUENCE: 259
taggtgtcca ccgcggcg 18

<210> SEQ ID NO 260
<211> LENGTH: 19
<212> TYPE: DNA
<213> ORGANISM: Homo sapiens

<400> SEQUENCE: 260
gcgccacctg tggatgacg 19

<210> SEQ ID NO 261
<211> LENGTH: 21
<212> TYPE: DNA
<213> ORGANISM: Homo sapiens

<400> SEQUENCE: 261
tctgcagtaa ttgtccacct g 21

<210> SEQ ID NO 262
<211> LENGTH: 21
<212> TYPE: DNA
<213> ORGANISM: Homo sapiens

<400> SEQUENCE: 262
gtctgcaata ggtgtccacc t 21

<210> SEQ ID NO 263
<211> LENGTH: 20
<212> TYPE: DNA
<213> ORGANISM: Homo sapiens

<400> SEQUENCE: 263
ctgcagtagt tgtccacccg 20

<210> SEQ ID NO 264
<211> LENGTH: 22
<212> TYPE: DNA
<213> ORGANISM: Homo sapiens

<400> SEQUENCE: 264
ccgtagttgt atctgcagta gt 22

<210> SEQ ID NO 265
<211> LENGTH: 22
<212> TYPE: DNA
<213> ORGANISM: Homo sapiens -continued

<400> SEQUENCE: 265
ccgtagttgt gtctgcagta gt 22

<210> SEQ ID NO 266
<211> LENGTH: 23
<212> TYPE: DNA
<213> ORGANISM: Homo sapiens

<400> SEQUENCE: 266
cccgtagttg tgtctgcagt aat 23

<210> SEQ ID NO 267
<211> LENGTH: 21
<212> TYPE: DNA
<213> ORGANISM: Homo sapiens

<400> SEQUENCE: 267
cccgtagttg tgtctgcaca c 21

<210> SEQ ID NO 268
<211> LENGTH: 21
<212> TYPE: DNA
<213> ORGANISM: Homo sapiens

<400> SEQUENCE: 268
cagcacgttt cttggagctg t 21

<210> SEQ ID NO 269
<211> LENGTH: 23
<212> TYPE: DNA
<213> ORGANISM: Homo sapiens

<400> SEQUENCE: 269
ttcttgtggc agcttaagtt tga 23

<210> SEQ ID NO 270
<211> LENGTH: 21
<212> TYPE: DNA
<213> ORGANISM: Homo sapiens

<400> SEQUENCE: 270 gatcccccctg aggtgaccgt g 21

<210> SEQ ID NO 271
<211> LENGTH: 21
<212> TYPE: DNA
<213> ORGANISM: Homo sapiens

<400> SEQUENCE: 271
ctgggcccgg gggtcatggc c 21

<210> SEQ ID NO 272
<211> LENGTH: 30
<212> TYPE: DNA
<213> ORGANISM: Homo sapiens

<400> SEQUENCE: 272
cacgtcgctg tcgaagcgca cgtactcctc 30

<210> SEQ ID NO 273
<211> LENGTH: 30
<212> TYPE: DNA

-continued

<213> ORGANISM: Homo sapiens

<400> SEQUENCE: 273
cacgtcgctg tcgaagcgga cgatctcctt 30

<210> SEQ ID NO 274
<211> LENGTH: 30
<212> TYPE: DNA
<213> ORGANISM: Homo sapiens

<400> SEQUENCE: 274
cacgtcgctg tcgaagcgtg cgtactcctc 30

<210> SEQ ID NO 275
<211> LENGTH: 30
<212> TYPE: DNA
<213> ORGANISM: Homo sapiens

<400> SEQUENCE: 275
cacgtcgctg tcgaagcgcg cgtactcctc 30

<210> SEQ ID NO 276
<211> LENGTH: 30
<212> TYPE: DNA
<213> ORGANISM: Homo sapiens

<400> SEQUENCE: 276
cacgtcgctg tcgaagcgca cgtcctcctc 30

<210> SEQ ID NO 277
<211> LENGTH: 30
<212> TYPE: DNA
<213> ORGANISM: Homo sapiens

<400> SEQUENCE: 277
tggcgtgggc gaggcagggt aacttcttta 30

<210> SEQ ID NO 278
<211> LENGTH: 30
<212> TYPE: DNA
<213> ORGANISM: Artificial Sequence
<220> FEATURE:
<223> OTHER INFORMATION: Description of Artificial Sequence:Capture
Oligonucleotide1

<400> SEQUENCE: 278
accgcacccg ctccgtccca ttgaagaaat 30